US008273561B2

(12) United States Patent
Cleland et al.

(10) Patent No.: US 8,273,561 B2
(45) Date of Patent: Sep. 25, 2012

(54) HIGH PRESSURE TREATMENT OF AGGREGATED INTERFERONS

(75) Inventors: Jeffrey L. Cleland, San Carlos, CA (US); Stephen P. Eisenberg, Boulder, CO (US); Mary S. Rosendahl, Broomfield, CO (US); Matthew B. Seefeldt, Boulder, CO (US)

(73) Assignee: Nuron Biotech, Inc., Exton, PA (US)

( * ) Notice: Subject to any disclaimer, the term of this patent is extended or adjusted under 35 U.S.C. 154(b) by 445 days.

(21) Appl. No.: 12/287,262

(22) Filed: Oct. 6, 2008

(65) Prior Publication Data
US 2009/0208453 A1  Aug. 20, 2009

Related U.S. Application Data

(60) Provisional application No. 60/997,782, filed on Oct. 5, 2007, provisional application No. 61/130,208, filed on May 29, 2008.

(51) Int. Cl.
*C07K 1/02* (2006.01)
*C07K 14/00* (2006.01)
*C12N 9/00* (2006.01)

(52) U.S. Cl. ...... 435/187; 530/427; 530/351; 435/69.51

(58) Field of Classification Search .................. None
See application file for complete search history.

(56) References Cited

U.S. PATENT DOCUMENTS

| | | | |
|---|---|---|---|
| 4,450,103 A | 5/1984 | Konrad et al. |
| 4,462,940 A | 7/1984 | Hanisch et al. |
| 4,518,584 A | 5/1985 | Mark et al. |
| 4,530,787 A | 7/1985 | Shaked et al. |
| 4,569,908 A | 2/1986 | Mark et al. |
| 4,572,798 A | 2/1986 | Koths et al. |
| 4,588,584 A | 5/1986 | Lumsden et al. |
| 4,588,585 A | 5/1986 | Mark et al. |
| 4,631,211 A | 12/1986 | Houghten |
| 4,652,630 A | 3/1987 | Bentle et al. |
| 4,738,844 A | 4/1988 | Bell et al. |
| 4,753,795 A | 6/1988 | Bell et al. |
| 4,769,233 A | 9/1988 | Bell et al. |
| 4,793,995 A | 12/1988 | Bell et al. |
| 4,816,440 A | 3/1989 | Thomson |
| 4,894,330 A | 1/1990 | Hershenson et al. |
| 4,914,033 A | 4/1990 | Bell et al. |
| 4,959,314 A | 9/1990 | Mark et al. |
| 4,966,843 A | 10/1990 | McCormick et al. |
| 5,004,605 A | 4/1991 | Hershenson et al. |
| 5,166,311 A | 11/1992 | Nichols |
| 5,183,746 A | 2/1993 | Shaked et al. |
| 5,326,859 A | 7/1994 | Sugano et al. |
| 5,458,135 A | 10/1995 | Patton et al. |
| 5,522,378 A | 6/1996 | Ritson et al. |
| 5,544,646 A | 8/1996 | Lloyd et al. |
| 5,545,723 A | 8/1996 | Goelz et al. |
| 5,643,566 A | 7/1997 | Hanisch et al. |
| 5,702,699 A | 12/1997 | Hanisch et al. |
| 5,775,320 A | 7/1998 | Patton et al. |
| 5,785,049 A | 7/1998 | Smith et al. |
| 5,814,485 A | 9/1998 | Dorin et al. |
| 5,876,969 A | 3/1999 | Fleer et al. |
| 5,934,272 A | 8/1999 | Lloyd et al. |
| 5,960,792 A | 10/1999 | Lloyd et al. |
| 5,976,574 A | 11/1999 | Gordon |

(Continued)

FOREIGN PATENT DOCUMENTS

EP 0028033 A2 5/1981

(Continued)

OTHER PUBLICATIONS

Yoshihiro Kuroda, et al., "Effects of Detergents on the Secondary Structures of Prion Protein Peptides as Studied by CD Spectroscopy," Sep. 3, 2002, pp. 212-220, Journal of Peptide Science, vol. 9, Publisher—European Peptide Society and John Wiley & Sons, Ltd., Kyoto, JP.

Yu-Chang John Wang and Robert R. Kowal., "Review of Excipients and pH's for Parenteral Products Used in the United States," Aug. 4, 1980, pp. 452-462, PDA Journal of Pharmaceutical Science and Technology., Nov.-Dec. 1980, vol. 34, No. 6, US.

Arakawa, T., "The effects of arginine on refolding of aggregated proteins: not facilitate refolding, but suppress aggregation." *Biochemical and Biophysical Research Communication*, 304:1, pp. 148-152, (2003).

(Continued)

*Primary Examiner* — Christine J Saoud
*Assistant Examiner* — Jegatheesan Seharaseyon
(74) *Attorney, Agent, or Firm* — Fox Rothschild LLP

(57) ABSTRACT

High pressure to treat aggregated interferons, particularly recombinant human interferon-β, to reduce the aggregate content of interferon material. Highly pure, soluble monomeric recombinant interferon-β is prepared in representative embodiments. Multiple strategies may be used in combination that make nonglycosylated IFN-β more amenable to high pressure treatment. It has been found that refolding yields of high pressure treatment can be significantly improved by use of a combination of strategies, including, or example a pre-treatment of the IFN-β that involves solubilizing and then precipitating the protein. This pre-treatment is particularly effective with respect to recombinant IFN-β inclusion bodies recovered from host cells such as *E. coli* cells. According to another strategy, refolding under high pressure is much more effective when the refolding reagent incorporating the IFN-β incorporates a zwitterionic surfactant and/or a cholate salt. When a solubilization and precipitation pre-treatment is used, the effectiveness of the high pressure treatment is further enhanced when the refolding reagent incorporating the protein incorporates a disulfide shuffling chemistry such as cysteine/cystine. According to still yet another strategy, high pressure treatment is more effective when using atypically high treatment pressures. When coupled with purification techniques, these strategies singly or in combination provide a low aggregate or substantially aggregate free, biologically active solution. Biologically active solutions comprising nonglycosylated interferon, said interferon comprising less than about 5 weight percent of protein aggregation has been found to exhibit improved PK/PD characteristics.

7 Claims, 35 Drawing Sheets

U.S. PATENT DOCUMENTS

| | | | |
|---|---|---|---|
| 5,981,474 | A | 11/1999 | Manning et al. |
| 5,985,248 | A | 11/1999 | Gordon et al. |
| 5,993,783 | A | 11/1999 | Eljamal et al. |
| 6,001,336 | A | 12/1999 | Gordon |
| 6,489,450 | B2 | 12/2002 | Randolph et al. |
| 6,887,462 | B2 | 5/2005 | Shirely et al. |
| 7,064,192 | B2 | 6/2006 | Randolph et al. |
| 7,371,373 | B2 | 5/2008 | Shirley et al. |
| 7,399,463 | B2 | 7/2008 | Shirley et al. |
| 7,595,040 | B2 | 9/2009 | Furuya et al. |
| 7,615,617 | B2 | 11/2009 | Robinson et al. |
| 7,892,531 | B2 | 2/2011 | Shirley et al. |
| 2002/0137895 | A1 | 9/2002 | Wolfe et al. |
| 2003/0133979 | A1* | 7/2003 | Burke et al. ............ 424/468 |
| 2004/0038333 | A1* | 2/2004 | Randolph et al. ........ 435/68.1 |
| 2004/0115169 | A1* | 6/2004 | Wolfe et al. ............ 424/85.6 |
| 2005/0008616 | A1 | 1/2005 | Nestaas et al. |
| 2005/0014240 | A1 | 1/2005 | Sherman et al. |
| 2005/0142110 | A1 | 6/2005 | Shirley et al. |
| 2007/0066813 | A1 | 3/2007 | Prior et al. |
| 2009/0214472 | A1 | 8/2009 | Filpula et al. |
| 2009/0215998 | A1 | 8/2009 | Antman et al. |
| 2010/0261275 | A1 | 10/2010 | Durocher et al. |

FOREIGN PATENT DOCUMENTS

| | | |
|---|---|---|
| EP | 0032134 A2 | 7/1981 |
| EP | 0034307 A2 | 8/1981 |
| WO | WO 93/00951 | 1/1993 |
| WO | WO 96/09085 | 3/1996 |
| WO | WO 96/32149 | 10/1996 |
| WO | WO 96/32152 | 10/1996 |
| WO | WO 97/41833 | 11/1997 |
| WO | WO 98/29096 | 7/1998 |
| WO | WO 2005/016311 | 2/2005 |
| WO | 2007062174 A2 | 5/2007 |

OTHER PUBLICATIONS

Lee, S. H., et al., "Effects of solutes on solubilization and refolding of proteins from inclusion bodies with high hydrostatic pressure," *Protein Science*, 15:2, pp. 304-313, (2006).

Seefeldt, M. B., et al., "High-pressure refolding of bikunin: Efficacy and thermodynamics," Protein Science, 13:10, pp. 2639-2650 (2004).

St. John, R. J., et al., "High-pressure refolding of disulfide-cross-linked lysozyme aggregates: Thermodynamics and optimization," *Biotechnology Progress* 18, pp. 565-571 (2002).

Tsumoto, K., et al., "Role of arginine in protein refolding, solubilization, and purification," *Biotech. Progress* 20:5, pp. 1301-1308 (2004).

Schwartz, E., et al., "The effect of molecular chaperones on in vivo and in vitro folding processes," Biological Chemistry 377, pp. 411-416 (1996).

Carpenter, J. F., et al., "Rational design of stable lyophilized protein formulations: Some practical advice," *Pharmaceutical Research* 14:8, pp. 969-975 (1997).

Chi, E. Y., et al., "Roles of conformational stability and colloidal stability in the aggregation of recombinant human granulocyte colony-stimulating factor," *Protein Science*, 12, pp. 903-913 (2003).

Buchner, J., et al., Renaturation, purification and characterization of recombinant fab-fragments produced in *Escherichia-coli, Biotechnology* 9, pp. 157-162 (1991).

Fischer, B., et al., "Isolation, renaturation, and formation of disulfide bonds of eukaryotic proteins expressed in *Escherichia-coli* as inclusion bodies," *Biotechnology and Bioengineering* 41:1, pp. 3-13 (1993).

Hevehan, D. L., et al., "Oxidative renaturation of lysozyme at high concentrations," Biotechnology and Bioengineering, 54:3 pp. 221-230 (1997).

Clark, E. D., et al., "Inhibition of aggregation side reactions during in vitro protein folding," *Methods of Enzymology*, 309, pp. 217-236 (1991).

Gilbert, H. F., "Molecular and cellular aspects of thiol disulfide exchange," *Advance in Enzymology and Related Areas of Molecular Biology*, 63, pp. 69-172 (1990).

Gilbert, H. F., et al., "Thiol/disulfide exchange equilibria and disulfide bond stability," *Methods of Enzymology*, 251, pp. 8-28 (1995).

St. John, R. J., et al., "High pressure fosters protein refolding from aggregates at high concentrations," *Proceedings of the National Academy of Sciences of the United States of America* 96:23, pp. 13029-13033 (1999).

Randolph, T. W., et al., "High hydrostatic pressure as a tool to study protein aggregation and amyloidosis," *Biochimica Et Biophysica Acta*, 1595: pp. 224-234 (2002).

Pestka, S., "Interferon Standards and General Abbreviations," *Methods in Enzymology*, vol. 119 (S. Pestka, ed.), Academic Press, New York, 119, pp. 14-23 (1986).

Runkel, L., et al., "Structural and functional differences between glycosylated and non-glycosylated forms of human Interferon-β (IFN-β)," *Pharmaceutical Research* 15:4, pp. 641-649 (1998).

Kuroda, Y., et al., "Effects of detergents on the secondary structures of prion protein peptides as studied by CD spectroscopy," *Journal of Peptide Science* 9, pp. 212-220 (2003).

Nagata, et al., "Synthesis in *E. coli* of a polypeptide with human leukocyte interferon activity," *Nature*, 284, pp. 316-320 (1980).

Goeddel., et al., "Human leukocyte interferon produced by *E. coli* is biologically active," *Nature*, 287, pp. 411-416 (1980).

Houghten, "General method for the rapid solid-phase synthesis of large numbers of peptides: Specificity of antigen-antibody interaction at the level of individual amino acids," *Proc. Natl. Acad. Sci. USA*, 82 pages 5131-5135 ,(1985).

Stewart and Young, "Solid phase peptide synthesis," (Pierce Chemical Company, Rockford, ILL (book).

Baraney and Merrifield "The peptide: analysis, snythesis," Biology, ed. Gross and Meinhofer, vol. 2 (Academic Press, New York, 1980), pp. 3-255 (1980).

Bodansky, "Principles of peptide synthesis," (Springer-Verlang, Berlin) (1984).

Gross and Meinhoffer, eds., "The peptides: analysis, synthesis," *Biology*, vol. 1 (Academic Press, New York) (1979).

Hannam, C., et al., "Synthesis of a Radiolabeled Zwitterionic Detergent and Its Use in Protein Purification," *Analytical Biochemistry*, 258, pp. 246-250 (1998).

Basu, A., et al., "Structure- Function Engineering of Interferon-β-Ib for improving stability, solubility, potency, immunogenicity, and pharmacokinetic Properties by site-selective mono-PEGylation," *Bioconjugate Chemistry* 17, pp. 618-630 (2006).

Myers and Miller, "Optimal alignments in linear space," *Comput. Appl. Biosci.*, 4: pp. 1-13 (1988).

Meyer J.D., et al., "Hydrophobic ion paring: Altering the solubility properties of Biomolecules," *Pharm. Res.* 15:2, pp. 188-193 (1998)

Levine, et al., "The use of surface tension measuremens in the design of antibody-bases product formulations," *J. Parenteral Sci. Technol.* 45:3, 160-165 (1991).

Williams et al., "The lyophilization of pharmaceuticals: A literature review," *J. Parenteral Sci. Technol.*, 38:2, pp. 48-59 (1984).

Masters, "Applications of Spray Drying," in *Spray-Drying Handbook* (5th ed; Longman Scientific and Technical), pp. 491-676 (1991).

Broadhead, et al., "The Spray Drying of Pharmaceuticals," *Drug Devel. Ind. Pharm.*, vol. 18:11&12, pp. 1169-1206 (1992).

Mummenthaler, et al., "Feasibility study on spray-drying protein pharmaceuticals: recombinant human growth hormone and tissue-type plasminogen activator," *Pharm. Res.*, 11:1, pp. 12-20 (1994).

Carpenter et al., "Modes of stabilization of a protein by organic solutes during desiccation," *Cryobiology*, 25, pp. 459-470 (1988).

Roser, B., "Trehalose drying: A novel replacement for freeze-drying," *Biopharm*, vol. 4, pp. 47-53 (1991).

Seefeldt, M. B., et al., "Specific volume and adiabiatic compressibility measurement of native and aggregated recombinant human interleukin 1-receptor agonist: Density differences enable pressure-modulated refolding," *J. of Biotech and Bioeng in Press*, (2006).

Anderson, et al., Specific Binding of 125I-Human Interferon-γ to High Affinity Receptors on Human Fibroblasts (1982) J. Biol. Chem. 257(19):11301-11304.

Clark, E.D. (2001) "Protein refolding for industrial processes." Current Opinion in Biotechnology 12(2): 202-207.

Karlin and Altschul, Methods for Assessing the statistical Significance of Molecular Sequence Features by Using General Scoring Schemes, Proc. Natl. Acad. Sci. USA vol. 87, pp. 2264-2268, Mar. 1990.

Altschul, S., et al., Gapped BLAST and PSI-BLAST: a new generation of protein database search programs (1997) Nucleic Acids Res. 25. 3389-3402.

Dayhoff, (1978) in Atlas of Protein Sequence and Structure 5.Suppl. 3, National Biomedical Research Foundation, Washington, D.C.—(Voluminous).

Seefeldt, M.B., (2005) High Pressure Refolding of Protein Aggregates: Efficacy and Thermodynamics, Department of Chemical and Biological Engineering, Boulder, Colo., University of Colorado—Boulder: 220—(Thesis)(Voluminous).

A.D. Randolph and M.A. Larson, Theory of particulate Processes (second ed.), Academic Press, Inc., San Diego (1988)—(Voluminous).

Voet and Voet (1990) Biochemistry (John Wiley & Sons, New York)—(Voluminous).

Higuchi, R. (PCR Protocols; M.A. Innis et al., eds. 1990, Academia Press)—(Voluminous).

D'Argenio, D.Z., and Schumitzky, A., ADAPT II User's Guide, Biomedical Simulation Resource, Los Angeles, Calif. 1997—(Voluminous).

Hermeling, Suzanne, et al., Development of a Transgenic Mouse Immune Tolerant for Human Interferon Beta, Pharmaceutical Research, 2005, 22, pp. 847-851.

Hermeling, Suzanne, et al., Structure-Immunogenicity Relationships of Therapeutic Proteins, Pharmaceutical Research, 2004, 21, pp. 897-903.

Gross and Meinhofer, vol. 2 (Academic Press, New York, 1980), pp. 3-254—(Voluminous).

Malucchi, S., Neutralizing Antibodies Reduce the Efficacy of βIFN During Treatment of Multiple Sclerosis, American Academy of Neurology (2004); 62; 2031.

Herberman, Ronald R., Augmentation by Interferon of Human Natural and Antibody-Dependent Cell-Midiated Cytotoxicity, Nature vol. 277, Jan. 18, 1979, pp. 221-223.

Williams, B.R.G., et al., Natural Occurrence of 2-5A in Interferon-treated EMC Virus-Infected L Cells, Nature vol. 282, Dec. 6, 1979, pp. 582-586.

Hermeling, Suzanne, et al., Antibody Response to Aggregate Human Interferon Alpha2b in Wild-type and Transgenic Immune Tolerant Mice Depends on Type and Level of Aggregation, Journal of Pharmaceutical Sciences, vol. 95, No. 5, (May 2006).

Extended European Search Report dated Nov. 17, 2010 for European Patent Appln. No. 08835251.3.

Altschul, S.F., et al., Basic Local Alignment Search Tool, J. Mol. Biol. (1990) 215, 403-410.

Taniguchi, T., et al., Molecular Cloning of Human Interferon cDNA, Proc. Natl. Acad. Sci. USA vol. 77, No. 7, pp. 4003-4006, (Jul. 1980).

Mager, Donald E., et al., Receptor-Mediated Pharmacokinetics and Pharmacodynamics of Interferon-β1 a in Monkeys, The Journal of Pharmacology and Experimental Therpeutics, vol. 306, No. 1. (2003).

PHRMA (2001). The Promise of Biotechnology and Genetic Research <www.phrma.org/publications/documents/backgrounds/2000-12-12.191.phtml>.

Baneyx, F. (1999) "Recombinant protein expression in *Escherichia coli*." Current Opinion in Biotechnology 10(5): 411-421.

Przybycien, T.M., et al. (1994). "Secondary Structure Characterization of Beta-Lactamase Inclusion-Bodies." Protein Engineering 7(1): 131-136.

Schellekens, H., Nephrol. Dial. Transplant. 18:1257 (2003).

Schellekens, H., Nephrol. Dial. Transplant. 20 [Suppl 6]: vi3-vi9 (2005).

Purohit, V., et al. J. Pharm. Sci. 95:358 (2006).

Fellous. M., et al (1982) Proc. Natl. Acad. Sci USA 79:3082-3086.

Mark, D.F., et al. (1984) ) Proc. Natl. Acad. Sci USA 81:5662-5666.

Karlin and Altschul: Applications and statistics for multiple high-scoring segments in molecular sequences, Proc. Natl. Acad. Sci USA vol. 90, pp. 5873-5877 (Jun. 1993).

Ohno, et al. Inducer-responsive Expression of the cloned human interferon β1 Gene Introduced into Cultured Mouse Cells, vol. 10, No. 3, pp. 967-977 (1982) Nucleic Acids Res.

Smith, et al. Production of Human Beta Interferon in Insect Cells Infected with Baculovirus Expression Vector, (1983) Mol Cell. Biol 3:2156.

Yelverton, E., et al. Bacterial Synthesis of a Novel Human Leukocyte Interferon, (1981) Nuc. Acid Res. 9:731.

Streuli, M., et al., Target Cell Specificity of Two Species of Human Interferon-α produced in *Escherichia coli* and of hybrid molecules Derived from them, (1981) Proc. Natl. Acad. Sci. U.S.A. 78:2848.

Li, C.H., et al., Total synthesis of Insulin-like Growth Factor I (somatomedin C), (1983) Proc. Natl. Acad. Sci USA 80:2215-2220.

Czarniecki, Christine W., et al., Synergistic Antiviral and Antiproliferative Activities of *Escherichia coli*-Derived Human Alpha, Beta, and Gamma Interferons, Journal of Virology, Feb. 1934, p. 490-496.

Mantei, Ned & Weissmann, Charles, Controlled Transcription of a Human α-interferon Gene Introduced into Mouse L Cells, Nature vol. 297, May 13, 1982, pp. 128-132.

Innis and McCormick, Procedures for Expression, Modification, and Analysis of Human Fibroblast interferon (IFN-beta) Genes in Heterologous Cells, Methods Enzymol. 1986; 119:397-403.

Schellekens, Huub, Bioequivalence and the Immunogenicity of Biopharmaceuticals, Nature Reviews vol. Jun. 2002, pp. 451-462.

International Search Report dated Jan. 28, 2009 for International Application No. PCT/US08/11559.

Written Opinion issued for PCT/US2008/0115599 dated Jan. 28, 2009.

Sen, Ganes C., et al. The Interferon System, The Journal of Biological Chemistry, vol. 267, No. 8, Issue of Mar. 15, pp. 5017-5020, 1992.

Office Action issued Jun. 18, 2012 re European Patent Application No. 08835251.3.

International Search Report issued Apr. 9, 2012 re International Application No. PCT/US 11/67698.

PCT Written Opinion issued Apr. 9, 2012 re International Application No. PCT/US 11/67698.

* cited by examiner

FIG. 1

(SEQ ID No. 2): Bar 25 protein AA sequence
SYNLLGFLQRSSNFQSQKLLWQLNGRLEYCLKDRMNFDIPEEIKQLQQFQKEDAALTIYEMLQNIFAIF
RQDSSSTGWNETIVENLLANVYHQINHLKTVLEEKLEKEDFTRGKLMSSLHLKRYYGRILHYLKAKEYS
HCAWTIVRVEILRNFYFINRLTGYLRN

FIG. 2

Bar 25 protein Gene Sequence (SEQ ID No. 3)
catATGAGCTACAACTTGCTTGGATTCCTACAAAGAAGCAGCAATTTTCAGTCTCAGAAGCTTCTGTGGC
AATTGAATGGGAGGCTTGAATACTGCCTCAAGGACAGGATGAACTTTGACATCCCTGAGGAGATTAAGCA
GCTGCAGCAGTTCCAGAAGGAGGACGCCGCATTGACCATCTATGAGATGCTCCAGAACATCTTTGCTATT
TTCAGACAAGATTCATCTAGCACTGGCTGGAATGAGACTATTGTTGAGAACCTCCTGGCTAATGTCTATC
ATCAGATAAACCATCTGAAGACAGTCCTGGAAGAAAAACTGGAGAAAGAAGATTTCACCAGGGGAAAACT
CATGAGCAGTCTGCACCTGAAAAGATATTATGGGAGGATTCTGCATTACCTGAAGGCCAAGGAGTACAGT
CACTGTGCCTGGACCATAGTCAGAGTGGAAATCCTAAGGAACTTTTACTTCATTAACAGACTTACAGGTT
ACCTCCGAAACTAAgaattc Construction of the Bar 25 protein Expression Plasmid Fermentation & Primary Recovery Processes Secondary Recovery Process & Formulated Bulk Drug Substance Bar 25 100L fermentation and primary recovery steps
(RT means room temperature herein)

Bar 25 100L fermentation and primary recovery steps

Bar 25 protein secondary recovery process steps

Bar 25 protein secondary recovery process steps

Percentage of aggregates in Sample 19A samples determined by SE-HLPC. Rate of aggregation for samples stored at 40°C is about 1.8%/week.

Percentage of aggregates in Sample 19B samples determined by SE-HLPC. Rate of aggregation for samples stored at 40°C is about 1.1%/week.

Percentage of parent in 19A stability samples analyzed by IEX-HPLC analysis. Rate of degradation is about 0.9%/week at 25°C, and 3.2%/week at 40°C.

Percentage of parent 19A aggregate-free stability samples analyzed by IEX-HPLC analysis. Rate of degradations are about 0.8%/week at 25°C, and 3.2%/week at 40°C.

Percentage of parent in 19A stability samples analyzed by RP-HPLC analysis. Rate of degradation is about 1.0%/week at 25°C, and 1.9%/week at 40°C.

Percentage of parent in 19B aggregate-free stability samples analyzed by RP-HPLC analysis. Rate of degradation is about 0.3%/week at 25°C, and 2.0%/week at 40°C.

*Relative IgG Anti-IFN β Responses Over Time in Individual Transgenic Mice Dosed With Different rh IFNβ protein preparations.*

Pharmacokinetic profile of rhIFN-β1b for the single 0.28mg/kg SC dose after simultaneous fitting the integrated PK/PD model to the naïve pooled PK and PD data. Symbols represent the experimental observations and line represents the predicted profile from the model.

Neopterin concentration-time profiles for three single SC doses of 0.01( ■, dash-dotted), 0.06 (▲, dashed) and, 0.28 mg/kg (●, solid) after simultaneous fitting the integrated PK/PD model to the naïve pooled PK and PD data. Symbols represent the experimental observations and lines represent the predicted profiles from the model.

Concentration-time profiles of IFN-β1b for three SC doses of 0.01(dash-dotted), 0.06 (▲, dashed) and, 0.28 mg/kg (●, solid) during multiple dosing. Symbols represent the experimental observations and lines represent the simulated profile using the integrated PK/PD model and the parameters obtained from the single dose PK/PD fits.

Neopterin concentration-time profiles for three SC doses of 0.01 (■, dash dotted), 0.06 (▲, dashed) and, 0.28 mg/kg (●, solid) during multiple dosing. Symbols represent the experimental observations and lines represent the simulated profile using the integrated PK/PD model and parameters obtained from the single dose PK/PD fits.

HIGH PRESSURE TREATMENT OF AGGREGATED INTERFERONS

This application claims the benefit of U.S. Provisional Application Ser. No. 60/997,782, filed Oct. 5, 2007, entitled "HIGH PRESSURE TREATMENT OF AGGREGATED INTERFERONS", and U.S. Provisional Application Ser. No. 61/130,208, filed May 29, 2008, entitled "HIGH PRESSURE TREATMENT OF AGGREGATED INTERFERONS", which applications are incorporated herein by reference in their entirety.

FIELD OF THE INVENTION

The present invention relates to using high pressure to treat aggregated interferons, particularly recombinant human interferon-β. More particularly, the present invention relates to improved conditions and refolding media for using high pressure to reduce the aggregate content of interferon material, particularly recombinant human interferon-β. Highly pure, soluble monomeric recombinant interferon-β, suitable for pharmaceutical composition is prepared in representative embodiments.

BACKGROUND OF THE INVENTION

Therapeutic proteins provide enormous potential for the treatment of human disease. Dozens of protein therapeutics are currently available, with hundreds more in clinical development. PhRMA (2001). *The Promise of Biotechnology and Genetic Research*. Unfortunately, protein aggregation is a common problem that arises during all phases of recombinant protein production, specifically during fermentation, purification, and long-term storage. Schwarz, E., H. Lilie, et al. (1996). "The effect of molecular chaperones on in vivo and in vitro folding processes." *Biological Chemistry* 377(7-8): 411-416. Carpenter, J. F., M. J. Pikal, et al. (1997). "Rational design of stable lyophilized protein formulations: Some practical advice." *Pharmaceutical Research* 14(8): 969-975. Baneyx, F. (1999). "Recombinant protein expression in *Escherichia coli*." *Current Opinion in Biotechnology* 10(5): 411-421. Clark, E. D. (2001). "Protein refolding for industrial processes." *Current Opinion in Biotechnology* 12(2): 202-207. Chi, E. Y., S. Krishnan, et al. (2003). "Roles of conformational stability and colloidal stability in the aggregation of recombinant human granulocyte colony-stimulating factor." *Protein Science* 12(5): 903-913.

During recombinant protein fermentation, protein instability commonly leads to extensive aggregation. Within prokaryotes such as *E. coli*, the reducing environment within the cytoplasm prevents the proper formation of disulfide bonds and commonly results in the creation of insoluble inclusion bodies of non-native protein. Przybycien, T. M., J. P. Dunn, et al. (1994). "Secondary Structure Characterization of Beta-Lactamase Inclusion-Bodies." *Protein Engineering* 7(1): 131-136. Inclusion body formation is additionally fostered by the overexpression of the recombinant protein of interest.

Chemical denaturants (chaotropes such as urea or guanidine HCl or denaturing surfactants such as sodium dodecyl sulfate ("SDS")) have been traditionally used to refold proteins from inclusion bodies. High concentrations of chaotropes or detergents (up to 6M guanidine HCl, 8M urea, 0.1% SDS) are required to thermodynamically denature the protein. Buchner, J. and R. Rudolph (1991). "Renaturation, purification and characterization of recombinant fab-fragments produced in *escherichia-coli.*" *Biotechnology* 9(2): 157-162. Fischer, B., I. Sumner, et al. (1993). "Isolation, renaturation, and formation of disulfide bonds of eukaryotic proteins expressed in *escherichia-coli* as inclusion bodies." *Biotechnology and Bioengineering* 41(1): 3-13. Clark, E. D. (2001). "Protein refolding for industrial processes." *Current Opinion in Biotechnology* 12(2): 202-207.

Refolding is achieved by removing the chaotrope or detergent after inclusion body and/or aggregate dissociation, commonly via dilution, dialysis, or diafiltration. Dilution is the most common method used. Aggregates are denatured at a concentration of approximately 40 mg/ml. This solution is diluted 50-100 fold in a solution containing low chaotrope concentrations (0.1-1.5 M) and a thiol reducing/oxidizing environment to enable the proper formation of disulfide bonds Hevehan, D. L. and E. D. Clark (1997). "Oxidative renaturation of lysozyme at high concentrations." *Biotechnology and Bioengineering* 54 (3): 221-230. Low protein concentrations are needed to prevent reaggregation since aggregation kinetics are typically second order to concentration. Despite these complicated processing steps, the folding energy landscape can be difficult to navigate and in many cases refolding is not viable due the formation of aggregate-prone intermediates and subsequent reaggregation Clark, E. D., E. Schwarz, et al. (1999). Inhibition of aggregation side reactions during in vitro protein folding. *Amyloid Prions, and Other Protein Aggregates*. Orlando, Fla., Academic Press Inc. 309: 217-236. Clark, E. D. (2001). "Protein refolding for industrial processes." *Current Opinion in Biotechnology* 12(2): 202-207.

Disulfide bond formation is an additional component of a refolding reaction that needs to occur to generate a biologically active, pharmaceutical composition during refolding. Native disulfide bond formation can often be confounded by competing non-native disulfide bonds reactions that can lead to aggregates. Disulfide shuffling agents (reduced/oxidized glutathione, cysteine/cystine, and cysteamine/cystamine) have been used extensively for the refolding of proteins that contain multiple disulfide bonds. Gilbert, H. F. (1990). "Molecular and cellular aspects of thiol disulfide exchange." *Advances in Enzymology and Related Areas of Molecular Biology* 63: 69-172. Gilbert, H. F. (1995). Thiol/disulfide exchange equilibria and disulfide bond stability. *Biothiols, Pt A*. Orlando, Fla., Academic Press. 251: 8-28. Clark, E. D. (2001). "Protein refolding for industrial processes." *Current Opinion in Biotechnology* 12(2): 202-207.

High hydrostatic pressure (c. a. 2000 bar) has also been shown to be an effective refolding tool, enabling refolding at relatively high concentration and with high yield. U.S. Pat. Nos. 7,064,192 and 6,489,450. St. John, R. J., J. F. Carpenter, et al. (1999). "High pressure fosters protein refolding from aggregates at high concentrations." *Proceedings of the National Academy of Sciences of the United States of America* 96(23): 13029-13033. Randolph, T. W., M. Seefeldt, et al. (2002). "High hydrostatic pressure as a tool to study protein aggregation and amyloidosis." *Biochimica Et Biophysica Acta-Protein Structure and Molecular Enzymology* 1595 (1-2): 224-234. St. John, R. J., J. F. Carpenter, et al. (2002). "High-pressure refolding of disulfide-cross-linked lysozyme aggregates: Thermodynamics and optimization." *Biotechnology Progress* 18(3): 565-571. Seefeldt, M. B., J. Ouyang, et al. (2004). "High-pressure refolding of bikunin: Efficacy and thermodynamics." *Protein Science* 13(10): 2639-2650. In contrast to traditional chaotrope-based refolding, high pressure techniques can dissociate aggregates under conditions that favor the protein's native conformation. St. John, R. J., J. F. Carpenter, et al. (2002). "High-pressure refolding of disulfide-cross-linked lysozyme aggregates: Thermodynamics and optimization." *Biotechnology Progress* 18(3): 565-571. Seefeldt, M. B., J. Ouyang, et al. (2004). "High-pressure refolding of bikunin: Efficacy and thermodynamics." *Protein Science* 13(10): 2639-2650. Additionally, high pressure refolding can be conducted in the absence of chaotropes or strong-binding detergents, facilitating downstream purification.

The interferons are a family of glycoproteins whose secretion from cells is induced by a number of signals, including viruses, double-stranded RNAs, other polynucleotides, antigens, and mitogens. Interferons exhibit multiple biological activities, including antiviral, antiproliferative, and immunomodulatory activities. At least three distinct types of human interferons, α, β, and γ, have been identified.

Human interferon-beta (IFN-β) and variants thereof are therapeutic proteins used for the treatment of multiple sclerosis. Human IFN-β is glycosylated when harvested from natural sources, but can be de-glycosylated. Synthetic IFN-β made via recombinant techniques with expression in *E. coli* or chemical synthesis is non-glycosylated.

A commercially important variant of human IFN-β modifies the native amino acid sequence in two ways. First, the cysteine residue at the 17 position is replaced with serine. Second, the methionine at the N-terminus is deleted. The cysteine residue at position 17 has been removed to remove the possibility for non-native disulfide bond formation to occur. This cysteine is typically buried in the glycosylated wild-type IFN-β. The removal of the methionine at the N-terminus is a consequence of expression in *E. coli*.

Glycosylated forms of human IFN-β typically tend to have a much longer plasma half life than non-glycosylated versions, meaning that glycosylated versions are retained in a patient's blood much longer. The half-life of commercially available glycosylated versions of IFN-β can be seven or more times longer than that of commercially available versions of the non-glycosylated IFN-β having an otherwise substantially identical amino acid sequence. Accordingly, there is a strong desire to find a way to improve half-life characteristics of non-glycosylated forms of human IFN-β to make the bioavailability more comparable to that of the glycosylated forms.

Notwithstanding such an advantage, the use of non-glycosylated versions of human IFN-β or variants thereof is still desirable. Expression in *E. coli*, which produces nonglycosylated IFN-β, is significantly easier and less expensive than mammalian cell expression, which produces glycosylated forms. One major obstacle that must be overcome in the use of non-glycosylated human IFN-β or variants thereof from *E. coli* as a therapeutic agent concerns refolding of aggregated inclusion bodies. Inclusion bodies tend to be generally completely aggregated and are desirably are refolded to reduce at least a portion of the aggregation to be therapeutically useful.

One early process for the refolding and production of non-glycosylated IFN-β is described in U.S. Pat. No. 4,462,940. Briefly, inclusion bodies of IFN-β are solubilized in a solution containing 0.1% SDS at a pH in the range of 4-8. The IFN-β is then extracted using 2-butanol or 2-methyl-2-butanol or mixtures thereof by co-current extraction. The pH of the butanol extract is then decreased to pH 5.5, which precipitates the IFN-β. Refolding of this IFN-β precipitate is conducted by re-solubilizing the pellet in SDS at a ratio of 1:3, adjusting the pH to 9.5, and adding a reducing agent such as dithiothreitol (DTT). Air oxidation is allowed to occur for the formation of disulfide bonds, and then the material is filtered and loaded on a sephacryl-200 column for purification by size exclusion. The aggregate peak is removed, and the monomeric material is purified a second time on a larger sephacryl-200 column. The monomer peak is purified further on a $3^{rd}$ column composed of Fractogel TSK™. At this point the pH of the system is increased to pH 11 and the SDS is diafiltered for removal. The IFN-β is then formulated with human serum albumin (HSA).

A variant of non-glycosylated human IFN-β is commercially available under the trade designation BETASERON. The BETASERON product has been reported to have an aggregate content of over 50 weight percent. Laura Runkel et al., "Structural and Functional Differences Between Glycosylated and Non-Glycosylated Forms of Human Interferon-β (IFN-β)" *Pharmaceutical Research* Vol. 15, No. 4, 1998, pages 641-649 (hereinafter referred to as the Runkel reference). Commercial BETASERON is currently formulated in a lyophilized formulation containing large amounts of human serum albumin (HSA).

A significant disadvantage of one conventional refolding method employed for the BETASERON product is that it relies substantially upon SDS throughout the refolding and purification process. SDS has long been known to be a denaturing surfactant, enabling non-native and aggregated proteins to remain in solution. Kuroda, Y., Y. Maeda, et al. (2003). "Effects of detergents on the secondary structures of prion protein peptides as studied by CD spectroscopy." *Journal Of Peptide Science* 9(4): 212-220. Since SDS solubilizes most proteins, the refolding method is prone to having large amount of *E. coli* contaminant proteins present. The denaturing effects of SDS also result in reaggregation once the denaturant is removed, orthogonal to urea or guanidine based refolding methods. Clark, E. D. (2001). "Protein refolding for industrial processes." *Current Opinion in Biotechnology* 12(2): 202-207. This results in the formation of soluble aggregates that are difficult to purify and can contain residual amounts of SDS.

There also are complications associated with the BETASERON product. First, aggregates are often not recognized as "natural" by the immune system (possibly by exposure of a new epitope on the protein in the aggregate which is not exposed in the non-aggregated protein, or possibly by formation in the aggregate of a new, unrecognized epitope), with the result that the immune system is sensitized to the administered recombinant protein aggregate. In many instances, the immune system produces antibodies that bind to the aggregates, which do not neutralize the therapeutic effect of the protein. However, in some cases, antibodies are produced that bind to the recombinant protein and interfere with the therapeutic activity thereby resulting in declining efficacy of the therapy. Furthermore, in some instances, repeated administration of a recombinant protein can cause acute and chronic immunologic reactions (see Schellekens, H., Nephrol. Dial. Transplant. 18:1257 (2003); Schellekens, H., Nephrol. Dial. Transplant. 20 [Suppl 6]:vi3-vi9 (2005); Purohit et al. J. Pharm. Sci. 95:358 (2006)). Neutralizing antibodies have been shown to develop in patients treated with BETASERON, likely due to the presence of aggregates in the pharmaceutical product. Malacchi, S., A. Sala, et al., (2004). "Neutralizing antibodies reduce the efficacy of beta interferon during treatment of multiple sclerosis." Neurology 62: 2031-2037. Soluble aggregates in the BETASERON product could be the source of efficacy and immunogenicity issues. Runkel, L., W. Meier, et al. (1998). "Structural and functional differences between glycosylated and non-glycosylated forms of human interferon-beta (IFN-β)." *Pharmaceutical Research* 15(4): 641-649. Hermeling, S., D. J. A. Crommelin, et al. (2004) "Structure-immunogenicity relationships of therapeutic proteins." Pharmaceutical Research 21(6): 897-903.

Another complication associated with the current BETA-SERON product is that HSA can contain aggregates and poses a risk of viral contamination. HSA is obtained from human donors and purified using Cohn fractionation and thus there is a constant risk of viral contamination with this product. Furthermore, the viral inactivation treatment (heating at 60° C. for 10 hours) used for the protein can cause aggregation of HSA.

An improved, HSA-free formulation of non-glycosylated IFN-β has been described in U.S. Patent Publication No. 2005/0142110 A1. However the aggregate content of this material is no lower than 6% and can be even higher depending upon factors including pH, ionic strength, and co-agents present in the formulation. U.S. Patent Publication No. 2002/0137895 A1 describes a chaotrope-based refolding method that leads to completely monomeric sized, however no mention is made of oxidation methods, and low pHs are used which quench disulfide formation. Human interferon-β SER17 has been disclosed to be purified by a procedure that uses a zwitterion detergent in combination with urea. See *Bioconjugate Chemistry* 17(3): 618-630; Russell-Harde. This process is carried out at ambient pressure. U.S. Pat. No. 4,530,787 discusses the need for oxidation and describes the use of the oxidative agent iodosobenzoic acid for the formation of disulfide bonds. Consequently, it is implied in US Patent Publication No. 2002/0137895 that the method described in this patent application only provides monomeric material, not active material with the appropriate disulfide bond.

There remains a strong need for improved techniques to reduce the aggregate content of interferon material, particularly recombinant human interferon-β. An additional benefit of this material is that it could have improved bioavailability due to its higher purity.

SUMMARY OF THE INVENTION

The present invention relates to using high pressure to treat aggregated interferons, as illustrated by recombinant human interferon-β. More particularly, the present invention relates to improved conditions and refolding media for using high pressure to reduce the aggregate content of interferon material, particularly recombinant human interferon-β. Highly pure, soluble monomeric recombinant interferon-β is prepared in representative embodiments.

It has been found that interferons, particularly nonglycosylated IFN-β, are highly resistant to disaggregation and refolding using high pressure treatment conditions and reagents that have worked quite well with so many other proteins. For example, these conventional high pressure treatment conditions involve the following specifications: 2000 bar for sixteen hours, 25° C., pH 8.0, 4 mM reduced glutathione (GSH), and 2 mM oxidized glutathione (GSSH) (1999 St. John; 2003 Seefeldt et al. Bikunin paper). Significantly, the present invention provides multiple strategies that can be used singly or in combination that make nonglycosylated IFN-β more amenable to high pressure treatment.

According to one strategy, it has been found that the refolding yields of high pressure treatment can be significantly improved by a pre-treatment of the IFN-β that involves solubilizing and then precipitating the protein. This pre-treatment is particularly effective with respect to recombinant IFN-β inclusion bodies recovered from host cells such as *E. coli* cells. According to another strategy, it has been found that refolding under high pressure is much more effective when the refolding reagent incorporating the IFN-β incorporates a zwitterionic surfactant and/or a cholate salt. When a solubilization and precipitation pre-treatment is used, the effectiveness of the high pressure treatment is further enhanced when the refolding reagent incorporating the protein incorporates a disulfide shuffling chemistry such as cysteine/cystine, which is a chemistry normally not used in connection with IFN-β refolding. According to still yet another strategy, high pressure treatment is more effective when using atypically high treatment pressures.

Implementing these strategies, particularly in combination, allows highly pure, monomeric, nonglycosylated IFN-β to be prepared. Quite remarkably, the aggregate level of the IFN-β produced after high pressure refolding and purification has low levels of aggregates relative to the current BETASERON product (at least 50% per the Runkel reference cited supra) and HSA-free formulations of IFN-β that have been reduced to practice after SDS-based refolding (Shirley, US 2005/0142110 A1), which at best-case contain 94% monomer.

A second benefit of employing the high pressure refolding technology is that the generated material has been found in primate trials to exhibit half-life characteristics that far surpass comparable properties of the commercially available nonglycosylated BETASERON™ product and even approach those of the commercially available glycosylated AVONEX® product. In experiments, a preferred mode of practice produced a monomeric, nonglycosylated IFN-β that had a half-life about seven times greater than the BETASERON product. The ability of a non-glycosylated IFN-β to so closely approach the half life performance of a glycosylated IFN-β is a remarkable and unforeseen achievement.

Thus, in an aspect of the present invention, a pharmaceutical composition is provided that comprises a therapeutically effective amount of a nonglycosylated interferon, said interferon comprising less than about 5 weight percent of protein aggregation. In other embodiments, the composition comprises less than about 2 or 1 weight percent of protein aggregation.

In another aspect of the present invention, a method of preparing a composition comprising nonglycosylated interferon to minimize the presence of inclusion bodies and aggregated nonglycosylated interferon, which method comprises the steps as detailed herein, wherein the resulting composition comprises less than about 5 weight percent of protein aggregation. In other embodiments, the composition resulting from this method comprises less than about 2 or 1 weight percent of protein aggregation.

The following definitions are used in this specification:

"Aggregated" with respect to a protein refers to protein material composed of a multiplicity of protein molecules wherein noncovalent interactions and/or intermolecular covalent bonds such as disulfide bonds hold the protein molecules together. Often, but not always, an aggregate contains sufficient molecules so that it is insoluble in aqueous medium at physiological pH. Inclusion bodies are a type of aggregate of particular interest, to which the present invention is applicable.

"Atmospheric pressure" (ambient) is approximately 15 pounds per square inch (psi) or 1 bar.

"Biologically active" means a protein or variant thereof has at least 10% of maximal known specific activity as measured in an assay that is generally accepted in the art to be correlated with the known or intended utility of the protein. For proteins intended for therapeutic use, the assay of choice is one accepted by a regulatory agency to which data on safety and efficacy of the protein must be submitted. A protein having greater than 10% of maximal known specific activity is "biologically active" for the purposes of the invention.

"Chaotropic agent" is a compound, including, without limitation, guanidine hydrochloride (guanidinium hydrochloride, GdmHCl), sodium thiocyanate, and/or urea) which disrupts the noncovalent intermolecular bonding within the protein, permitting the amino acid chain to assume a substantially random conformation.

"Denatured" as applied to a protein in the present context, means that the protein molecule's native secondary and/or tertiary structure is disrupted to an extent that the protein does not have biological activity.

"Denaturing surfactants" are surfactants that bind to the protein, but may not modulate or disrupt the hydrogen bonding of water and therefore are not generally considered to be a chaotrope. An example of a commonly used denaturing surfactant is SDS.

"Glycosylated" describes the process or result of addition of saccharides to proteins. Two types of glycosylation can exist: N-linked glycosylation to the amide nitrogen of asparagine side chains and O-linked glycosylation to the hydroxy oxygen of serine and threonine side chains.

"Heterologous proteins" are proteins which are normally not produced by a particular host cell. Recombinant DNA technology has permitted the expression of relatively large amounts of heterologous proteins (for example, growth hormone) from transformed host cells such as $E. coli$. These proteins are often sequestered in insoluble inclusion bodies in the cytoplasm and/or periplasm of the host cell. The inclusion bodies or cytoplasmic aggregates contain, at least in part, the heterologous protein to be recovered. These aggregates often appear as bright spots under a phase contrast microscope.

"Host cell" a microbial cell such as bacteria and yeast or other suitable cell including animal or a plant cell which has been transformed to express the heterologous protein of interest. Host cells which are contemplated by the present invention are those in which the heterologous protein expressed by the cell is sequestered in refractile bodies. An exemplary host cell is $E. coli$ K12, strain W3110G [pBGHI], which has been transformed to effect expression of the desired heterologous protein.

"IFN or IFNs" refers to the family of secreted proteins known as interferons, which are cytokines with pleiotropic effects, including, for example, antiviral, anti-protozoal, immunomodulatory, and cell growth regulatory activities. IFNs were originally classified by their sources: leukocytes (IFN-α-1 and IFN-α-2), fibroblasts (IFN-β), and immune cells (IFN-γ). See, for example, Peskta, S. (1986) supra; Sen, G. C. and Lengyel, P. (1992) supra; and Pestka, S., ed., Interferons Part C in Meth. Enzymol. Vol. 119, Academic Press, Inc., New York, N.Y. (1986).

"IFN-β" refers to fibroblast IFN, which in man is a single gene lacking introns. The DNA or polynucleotide sequence of human IFN-β is described in Taniguchi, T. et al. (1980a) supra and U.S. Pat. No. 5,326,859. The human IFN-β cDNA encodes a pro-polypeptide 187 amino acids in length. A 21 amino acid signal sequence is cleaved off to form the mature, secreted IFN-β, polypeptide, which is 166 amino acids in length.

"IFN-β-1a" refers to recombinant human IFN-β, expressed in Chinese hamster ovary ("CHO") cells. As shown in FIG. 1, mature secreted IFN-β-1a is 166 amino acids in length, corresponding to native IFN-β. IFN-β-1a is N-linked glycosylated at the asparagine residue at position 80 (Asp80). See, for example, Innis, M. A. and McCormick, F. et al. (1986) supra and U.S. Pat. No. 4,966,843.

"IFN-β-1b" refers to recombinant human IFN-β expressed in $E. coli$ host cells and having a cysteine to serine amino acid substitution at position 17 (Ser17). When IFN-β-1b is processed in $E. coli$ and the N-terminal methionine is removed, it is 165 amino acids in length with Ser2 at the N-terminus. IFN-β-1b is not glycosylated. See, for example, Mark, D. F. et al. (1984) supra and U.S. Pat. No. 4,588,585.

"Inclusion bodies" are insoluble, aggregated proteins that form within host cells during overexpression of recombinant proteins in $E. coli$.

"Native conformation" of a protein, in the present context, refers to the secondary, tertiary and quaternary structures of a protein as it occurs in nature in a biologically active state.

"Native" or "naturally occurring" proteins or polypeptides refer to proteins or polypeptides recovered from a source occurring in nature. The term "native IFN-β" or "naturally occurring IFN-β" would include native or naturally occurring IFN-β and fragments thereof, and would include post-translational modifications of IFN-β and fragments thereof, including, but not limited to, acetylation, carboxylation, glycosylation, phosphorylation, lipidation, acylation, and cleavage.

"Non-glycosylated" means a protein that does not contain any saccharides.

"Recombinant proteins or polypeptides" refer to proteins or polypeptides produced by recombinant DNA techniques, i.e., produced from cells, microbial or mammalian, transformed by an exogenous recombinant DNA expression construct encoding the desired protein or polypeptide. Proteins or polypeptides expressed in most bacterial cultures will typically be free of glycan. Proteins or polypeptides expressed in yeast may have a glycosylation pattern different from that expressed in mammalian cells.

"Refolding" (renaturing, naturing), in the present context, means that a fully or partially denatured protein adopts secondary, tertiary and quaternary structure like that of the cognate native molecule. A (properly) refolded protein has biological activity which is substantially that of the non-denatured molecule. Where the native protein has disulfide bonds, oxidation to form native intramolecular disulfide bonds is a desired component of the refolding process.

"Treating" or "treatment" as used herein covers the treatment of disease-state in a mammal, preferably a human. In a preferred embodiment, the disease-state to be treated is characterized by symptoms associated with MS, such as weakness, numbness, tremor, loss of vision, pain, paralysis, loss of balance, bladder and bowel dysfunction, and cognitive changes (primary symptoms); repeated urinary tract infections, disuse weakness, poor postural alignment and trunk control, muscle imbalance, decreased bone density, shallow, inefficient breathing, and bedsores (secondary symptoms); and depression (tertiary symptoms), and includes:

(i) inhibiting the condition, i.e., arresting its development; or (ii) relieving the condition, i.e., causing regression of the condition.

Treatment of additional disease-states by the compositions described herein, such as myocarditis and cardiac dysfunction, arthritis, disorders or diseases of the central nervous system (CNS), brain, and/or spinal cord, including Alzheimer's disease, Parkinson's disease, Lewy body dementia, epilepsy, cerebellar ataxia, progressive supranuclear palsy, amyotrophic lateral sclerosis, affective disorders, anxiety disorders, obsessive compulsive disorders, personality disorders, attention deficit disorder, attention deficit hyperactivity disorder, Tourette Syndrome, Tay Sachs, Nieman Pick, and schizophrenia; nerve damage from cerebrovascular disorders such as stroke in the brain or spinal cord, from CNS infections including meningitis and HIV, from tumors of the brain and spinal cord, or from a prion disease; autoimmune diseases, including acquired immune deficiency, rheumatoid arthritis, psoriasis, Crohn's disease, Sjogren's syndrome, amyotropic lateral sclerosis, and lupus; and cancers, including breast, prostate, bladder, kidney and colon cancers, and diseases responsive to treatment by an anti-viral composition, is also specifically contemplated.

"Zwitterionic" refers to a compound that is electrically neutral but carries formal positive and negative charges on different atoms. Zwitterions are polar and usually have a high solubility in water.

BRIEF DESCRIPTION OF THE DRAWINGS

The accompanying drawings, which are incorporated in and constitute a part of this application, illustrate several aspects of the invention and together with a description of the embodiments serve to explain the principles of the invention. A brief description of the drawings is as follows:

FIG. 1 shows the sequence for SEQ ID No. 2.

FIG. 2 shows the sequence for SEQ ID No. 3.

DETAILED DESCRIPTION

Figure 3:
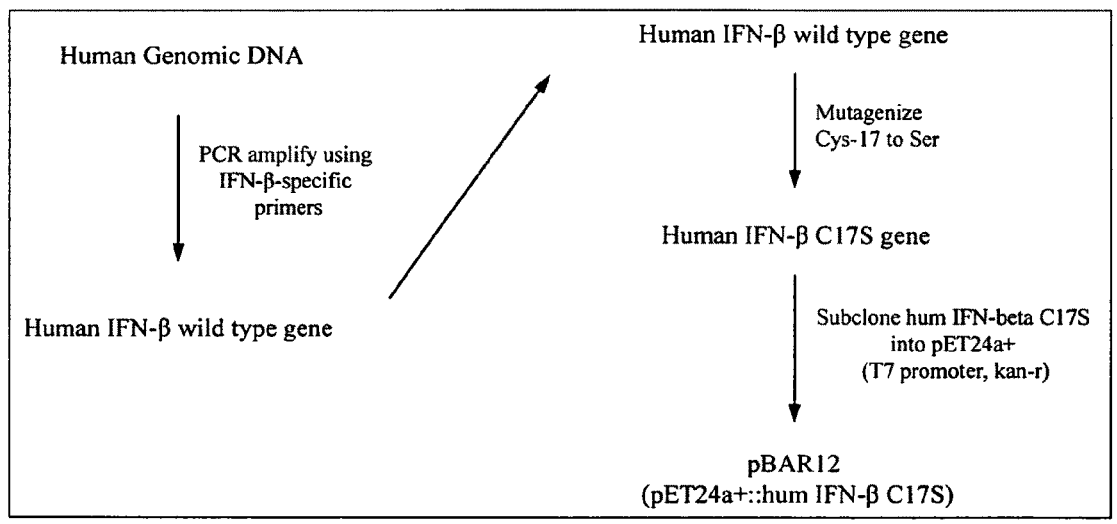
FIG. 3 is a schematic diagram of construction of a protein expression plasmid.

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention.

The present invention provides a method for preparing highly soluble and essentially monomeric, biologically active, non-glycosylated, interferon proteins from a protein mixture comprising an aggregated, non-glycosylated, interferon material. Building upon the high pressure deaggregation and refolding technology introduced in U.S. Pat. Nos. 6,489,450; and 7,064,192, the present invention teaches improved strategies and media to accomplish high pressure disaggregation and refolding beneficially applied to non-glycosylated interferons and variants thereof.

Desirably, non-glycosylated, interferon proteins of the present invention are non-glycosylated versions of the α, β, and/or γ human interferons or variants thereof. Most desirably, the interferon proteins of the present invention are non-glycosylated versions of human interferon-β ("nongly-IFN-β") or variants thereof. IFN-β polypeptides may be glycosylated or nonglycosylated. It has been reported in the literature that both the glycosylated and nonglycosylated IFN-β's show qualitatively similar specific activities and that, therefore, the glycosyl moieties are not involved in and do not contribute to the biological activity of IFN-β. Therefore, the nonglycosylated IFN-β's have substantially similar biological activity as otherwise identical IFN-β's that are naturally glycosylated.

The principles of the present invention preferably are applicable to human, nonglycosylated IFN-β and variants thereof such as the protein according to SEQ ID No. 1

MSYNLLGFLQRSSNFQSQKLLWQLNGRLEYCLKDRMNFDIPEEIKQLQQF

QKEDAALTIYEMLQNIFAIFRQDSSSTGWNETIVENLLANVYHQINHLKT

VLEEKLEKEDFTRGKLMSSLHLKRYYGRILHYLKAKEYSHCAWTIVRVEI

LRNFYFINRLTGYLRN

Biologically active with respect to variants of IFN-β according to the invention preferably means that the variants retain IFN-β activities, particularly the ability to bind to IFN-β receptors. In preferred embodiments the IFN-β variant retains at least about 25%, about 50%, about 75%, about 85%, about 90%, about 95%, about 98%, about 99% or more of the biological activity of the polypeptides whose amino acid sequences are given in SEQ ID NO: 1 or 2 with respect to the cytopathic effect (CPE) assay (Peska, *Methods in Enzymology*, v119, pg. 14-23, 1986). IFN-β variants whose activity is increased in comparison with the activity of the polypeptides shown in SEQ ID NO: 1 or 2 are also encompassed. The biological activity of IFN-β variants can be measured by any method known in the art. Examples of such assays can be found in Fellous et al. (1982) *Proc. Natl. Acad. Sci USA* 79:3082-3086; Czerniecki et al. (1984) *J. Virol.* 49(2):490-496; Mark et al. (1984) *Proc. Natl Acad. Sci. USA* 81:5662-5666; Branca et al. (981) *Nature* 277:221-223; Williams et al. (1979) *Nature* 282:582-586; Herberman et al. (1979) *Nature* 277:221-223; Anderson et al. (1982) *J. Biol. Chem.* 257(19):11301-11304; and the IFN-β potency assay described herein (see Example 11).

Variants include biologically active fragments of the peptide shown in SEQ ID No. 1 or biologically active fragments of variants of the peptide shown in SEQ ID No. 1. These biologically active fragments or truncated forms of IFN-β or variants thereof are generated in any convenient manner such as by scission of the peptide itself or such as by removing amino acid residues from the full-length IFN-β amino acid sequence using recombinant DNA techniques well known in the art.

Variants also include biologically active embodiments in which one or more amino acid residues not essential to biological activity are deleted, replaced, or added, including when such deletions, replacements, and additions enhance biological activity. One such variant includes a modification of the human IFN-β sequence shown in SEQ ID NO: 1, wherein one or more cysteine residues that are not essential to biological activity have been deliberately deleted or replaced with other amino acids to eliminate sites for either intermolecular crosslinking or incorrect intramolecular disulfide bond formation. IFN-β variants of this type include those containing a glycine, valine, alanine, leucine, isoleucine, tyrosine, phenylalanine, histidine, tryptophan, serine, threonine, or methionine substituted for the cysteine found at amino acid 17 of the mature native amino acid sequence. Serine and threonine are the more preferred replacements because of their chemical analogy to cysteine. Serine substitutions are most preferred.

Another such variant includes a modification of the human IFN-β sequence shown in SEQ ID NO: 1, wherein the amino-terminal methionine is removed. In recombinant synthesis, this is accomplished using widely known techniques by which the terminal methionine is removed by the *E. coli* enzyme methionine aminopeptidase so that the amino-terminal sequence is Ser-Tyr-Asn . . . .

A particularly preferred variant is the variant according to SEQ ID No. 2:

SYNLLGFLQRSSNFQSQKLLWQLNGRLEYCLKDRMNFDIPEEIKQLQQFQ

KEDAALTIYEMLQNIFAIFRQDSSSTGWNETIVENLLANVYHQINHLKTV

LEEKLEKEDFTRGKLMSSLHLKRYYGRILHYLKAKEYSHCAWTIVRVEIL

RNFYFINRLTGYLRN wherein the amino acid residue at position 17 is changed from cysteine to serine, and the terminal methionine in the native sequence is deleted. The calculated molecular weight of this variant is about 19880 and the theoretical pI is 9.02.

The skilled artisan will appreciate that other biologically active variants can be derived by introducing additional additions, deletions, replacements or modifications to amino acids of the native human IFN-β sequence according to SEQ ID No. 1 or variants thereof. For example, in addition to position 17, other conservative amino acid substitutions may be made at one or more predicted, preferably nonessential amino acid residues. A "nonessential" amino acid residue is a residue that can be altered from the wild-type sequence of IFN-β without unduly altering its biological activity, whereas an "essential" amino acid residue is required for biological activity. A "conservative amino acid substitution" often is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

Alternatively, variant IFN-β sequences can be made by introducing amino acid modifications, replacements, deletions, or additions randomly along all or part of the entire IFN-β chain. These mutants could be used to generate fusion proteins, PEGylated proteins or others as known by one skilled in the art. The resultant mutants can be screened for IFN-β biological activity to identify mutants that retain activity. Following mutagenesis, the encoded protein can be expressed recombinantly, and the activity of the protein can be determined using standard assay techniques described herein. Biologically active variants of IFN-β will generally have at least 80%, more preferably about 90% to about 95% or more, and most preferably about 96% to about 99% or more amino acid sequence identity to the amino acid sequence of mature native IFN-β, of SEQ ID No. 1, which serves as the basis for comparison. By "sequence identity" is intended the same amino acid residues are found within the variant polypeptide and the polypeptide molecule that serves as a reference when a specified, contiguous segment of the amino acid sequence of the variant is aligned and compared to the amino acid sequence of the reference molecule.

For purposes of optimal alignment of the two sequences for the purposes of sequence identity determination, the contiguous segment of the amino acid sequence of the variant may have additional amino acid residues or deleted amino acid residues with respect to the amino acid sequence of the reference molecule. The contiguous segment used for comparison to the reference amino acid sequence will comprise at least 20 contiguous amino acid residues. Corrections for increased sequence identity associated with inclusion of gaps in the variant's amino acid sequence can be made by assigning gap penalties. Methods of sequence alignment are well known in the art.

Thus, the determination of percent identity between any two sequences can be accomplished using a mathematical algorithm. One preferred non-limiting example of a mathematical algorithm utilized for the comparison of sequences is the algorithm of Myers and Miller (1988) *Comput. Appl. Biosci.* 4:11-7. Such an algorithm is utilized in the ALIGN program (version 2.0), which is part of the GCG alignment software package. A PAM120 weight residue table, a gap length penalty of 12, and a gap penalty of 4 can be used with the ALIGN program when comparing amino acid sequences. Another preferred, non-limiting example of a mathematical algorithm for use in comparing two sequences is the algorithm of Karlin and Altschul (1990) *Proc. Natl. Acad. Sci. USA* 90:5 873-5877, modified as in Karlin and Altschul 7 (1993) *Proc. Natl. Acad. Sci USA* 90:5873-5877. Such an algorithm is incorporated into the NBLAST and XBLAST programs of Altschul et al. (1990) *J. Mol. Biol.* 215:403-410. BLAST amino acid sequence searches can be performed with the XBLAST program, score=50, wordlength=3, to obtain amino acid sequence similar to the polypeptide of interest. To obtain gapped alignments for comparison purposes, gapped BLAST an be utilized as described in Altschul et al. (1997) *Nucleic Acids Res.* 25:3389-3402. Alternatively, PSI-BLAST can be used to perform an integrated search that detects distant relationships between molecules. See Altschul et al. (1997) supra. When utilizing BLAST, gapped BLAST, or PSI-BLAST programs, the default parameters can be used. See www.ncbi.nlm.nih.gov. Also see the ALIGN program (Dayhoff (1978) in *Atlas of Protein Sequence and Structure* 5:Suppl. 3, National Biomedical Research Foundation, Washington, D.C.) and programs in the Wisconsin Sequence Analysis Package, Version 8 (available from Genetics Computer Group, Madison, Wis.), for example, the GAP program, where default parameters of the programs are utilized.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Myers and Miller (1988) *Comput. Appl. Biosci.* 4:11-17.

The nonglycosylated interferon used in the practice of the present invention can be obtained from natural or nonnatural sources. Natural interferon can be sourced from humans, other primates, dogs, cats, rabbits, goats, sheep, bovines, equines, porcines, avians, and the like. Glycosylated forms of natural interferon proteins such as IFN-β harvested from natural sources can be de-glycosylated to form non-glycosylated interferons. Laura Runkel et al., "Structural and Functional Differences Between Glycosylated and Non-Glycosylated Forms of Human Interferon-β (IFN-β)" *Pharmaceutical Research* Vol. 15, No. 4, 1998, pages 641-649.

In preferred embodiments of the present invention, the IFN-β is recombinantly produced. By "recombinantly produced IFN-β" is intended IFN-β that has comparable biological activity to mature native IFN-β and that has been prepared by recombinant DNA techniques. IFN-β can be produced by culturing a host cell transformed with an expression vector comprising a nucleotide sequence that encodes an IFN-β polypeptide. The host cell is one that can transcribe the nucleotide sequence and produce the desired protein, and can be prokaryotic (for example, *E. coli*) or eukaryotic (for example a yeast, insect, or mammalian cell). Examples of recombinant production of IFN-β are given in Mantei et al. (1982) *Nature* 297:128; Ohno et al. (1982) *Nucleic Acids Res.* 10:967; Smith et al. (1983) *Mol. Cell. Biol.* 3:2156, and U.S. Pat. Nos. 4,462,940, 5,702,699, and 5,814,485; herein incorporated by reference. Human interferon genes have been cloned using recombinant DNA ("rDNA") technology and have been expressed in *E. coli* (Nagola et al. (1980) *Nature* 284:316; Goeddel et al. (1980) *Nature* 287:411; Yelverton et al. (1981) *Nuc. Acid Res.* 9:731; Streuli et al. (1981) *Proc. Natl. Acad. Sci. U.S.A.* 78:2848). Alternatively, IFN-β can be produced by a transgenic animal or plant that has been genetically engineered to express the IFN-β protein of interest in accordance with methods known in the art.

Proteins or polypeptides that exhibit native interferon-beta-like properties may also be produced with rDNA technology by extracting poly-A-rich 12S messenger RNA from virally induced human cells, synthesizing double-stranded cDNA using the mRNA as a template, introducing the cDNA into an appropriate cloning vector, transforming suitable microorganisms with the vector, harvesting the microorganisms, and extracting the interferon-beta therefrom. See, for example, European Pat. Application Nos. 28033 (published May 6, 1981); 32134 (published Jul. 15, 1981); and 34307 (published Aug. 26, 1981), which describe various methods for the production of interferon-beta employing rDNA techniques.

Alternatively, IFN-β can be synthesized chemically or in a non-cell expression system, by any of several techniques that are known to those skilled in the peptide art. See, for example, Li et al. (1983) *Proc. Natl. Acad. Sci. USA* 80:2216-2220, Steward and Young (1984) *Solid Phase Peptide Synthesis* (Pierce Chemical Company, Rockford, Ill.), and Baraney and Merrifield (1980) *The Peptides: Analysis, Synthesis, Biology*, ed. Gross and Meinhofer, Vol. 2 (Academic Press, New York, 1980), pp. 3-254, discussing solid-phase peptide synthesis techniques; and Bodansky (1984) *Principles of Peptide Synthesis* (Springer-Verlag, Berlin) and Gross and Meinhofer, eds. (1980) *The Peptides: Analysis, Synthesis, Biology*, Vol. 1 (Academic Press, New York), discussing classical solution synthesis. IFN-β can also be chemically prepared by the method of simultaneous multiple peptide synthesis. See, for example, Houghten (1984) *Proc. Natl. Acad. Sci. USA* 82:5131-5135; and U.S. Pat. No. 4,631,211.

Note that recombinant IFN-β tends to be produced in non-glycosylated form. Thus, inclusion bodies of IFN-β are non-glycosylated as synthesized. Similarly, chemically synthesized IFN-β tends to be produced in non-glycosylated form unless affirmative reaction steps are carried out to accomplish glycosylation. These glycosylation steps need not be carried out inasmuch as the present invention beneficially is applicable to nonglycosylated forms of interferons.

In a representative mode of practice, an aggregated mixture of nonglycosylated-IFN-β ("nongly-IFN-β") beneficially processed in the practice of the present invention is obtained by recovering inclusion bodies from *E. coli* pellets derived from *E. coli* host cells in which the nongly-IFN-β had been recombinantly synthesized. Inclusion bodies tend to be completely aggregated, with high levels of non-native intermolecular beta-sheet, secondary structures.

The inclusion bodies (also referred to as refractile bodies) can be recovered from these pellets by any suitable technique such as those described, for example, in U.S. Pat. No. 4,652, 630. High pressure homogenizers are commercially marketed to carry out cell lysis to recover inclusion bodies for this purpose. For example, the host cell can be disrupted by mechanical means such as a Manton-Gaulin homogenizer or French press. It is preferred that the disruption process be conducted so that cellular debris from the host organism is so disrupted that it fails to sediment from the homogenate solution under low speed centrifugation sufficient to sediment the refractile bodies. The refractile bodies are preferably resuspended, washed and centrifuged again. The supernatant is discarded yielding a substantially pure preparation of refractile bodies. Although not critical to the practice of the present invention, it is preferred that the refractile body preparation be homogenized again to ensure a freely dispersed preparation devoid of agglomerated refractile bodies. The preparation may be homogenized in a Manton-Gaulin homogenizer at 3000-5000 psig. When using a high pressure homogenizer for cell lysis, the whole cells can be suspended in a 20 mM Tris, 2 mM EDTA buffer prior to processing. Chemical methods can also be used to disrupt the cells and recover the inclusion bodies. The Examples below include a representative chemical methodology for carrying out this kind of recovery.

In preferred modes of practice, the aggregated interferon mixture is solubilized and precipitated before disaggregating and refolding under pressure. Several advantages result. First, following this protocol allows the aggregated interferon mixture to be refolded under high pressure to provide processed protein material with reduced aggregate content much more effectively. In preferred modes of practice described below, nongly-IFN-β containing less than 10 weight %, even less than 5 weight percent, and even less than 1 weight percent aggregated content at yields of at least about 30% or at least about 40%, or over 40% are achieved. These are stunningly low aggregate content numbers at such high yields. In contrast, a commercially available form of non-glycosylated IFN-β available under the trade designation BETASERON has been evaluated to have aggregate content over 50 weight percent, even over 60 weight percent. See the Runkel reference, supra.

If the solubilization and precipitation protocol is not practiced with respect to the interferon material, much less disaggregation and/or refolding occurs under high pressure. For example, in one set of experiments, IFN-β inclusion bodies were washed and then subjected to high pressure treatment using conditions and refolding media in accordance with U.S. Pat. No. 6,489,450 without being solubilized and precipitated before the high pressure treatment. A refolding yield of less than about 1% was obtained for the refolding of IFN-β from inclusion bodies under refolding conditions of pH 8, 2000 bar, 25° C., 16 hours, using glutathione as a disulfide forming reagent. Example 2, below, describes this experiment in the Examples below. The same result was obtained even after repeating the experiment in the presence of arginine, a commonly used refolding agent. In sharp contrast, when the aggregated material is first solubilized and precipitated prior to high pressure treatment using improved refolding conditions and refolding media as taught herein, higher yields of disaggregated and refolded interferon can be obtained.

In Example 2 mentioned above, the comparison example used high-pressure conditions and refolding media described in the prior U.S. Pat. No. 6,489,450. The use of solubilization and precipitation methods in combination with improved refolding conditions and media as described herein clearly provided improved yields relative to Example 2. However, the solubilization and precipitation protocol also provides significant yield advantages when used in combination with the improved refolding conditions and media described herein. In an embodiment of the present invention in which solubilization and precipitation was not used, inclusion bodies of IFN-β were washed and then subjected to high pressure refolding in the Preferred Refolding Reagent A (described below). A yield of refolded IFN-β of about 19% was obtained. This is dramatically better than the yield obtained in Example 2 described above, and yet this yield improves dramatically when practiced in combination with solubilization and precipitation. When refolding in the same Preferred Refolding Reagent A followed sec-butanol extraction/methanol precipitation, the yield jumps markedly to about 41%. While not being bound by theory, it is believed that the solubilization and extraction protocol provides more pure aggregates and/or different aggregate structures that are more amenable to high pressure refolding.

In short, the use of solubilization and precipitation protocols improves high pressure refolding yields of interferon proteins. The yields can be enhanced by selection of one or more additional high pressure, refolding conditions and/or refolding media characteristics, described further below. Significantly, these methods, coupled with purification, result in substantially aggregate-free, biologically active, nonglycosylated IFN-β material. Substantially aggregate-free means that the non-glycosylated interferon has an aggregate content of less than 5 percent by weight, desirably less than 2 weight percent, more desirably less then 0.8 weight percent.

The amount of aggregated protein in the protein composition is measured by any one method selected from the group consisting of analytical ultracentrifugation, size exclusion chromatography, field flow fractionation, light scattering, light obscuration, fluorescence spectroscopy, gel electrophoresis, GEMMA analysis, and nuclear magnetic resonance spectroscopy (that is, the percentage can be based on any one method of analysis, to the exclusion of other methods of analysis). Alternatively, the amount of aggregated protein in the protein composition measured by at least one method selected from the group consisting of analytical ultracentrifugation, size exclusion chromatography, field flow fractionation, light scattering, light obscuration, fluorescence spectroscopy, gel electrophoresis, GEMMA analysis, and nuclear magnetic resonance spectroscopy (that is, the percentage can be based on any one method of analysis, without necessarily excluding other methods of analysis).

According to a preferred methodology, aggregate content is determined by Size-Exclusion Chromatography (SE-HPLC). SEC-HPLC analysis of protein fractions may be conducted on a Agilent 1100 equipped with a TSK G2000 SWXL size exclusion column (Tosohaas). The HPLC parameters are as follows: Solvent of 10 mM HCL in water, flow rate of 0.5 ml/min (isocratic), room temperature, an injection of 50 ml with absorbance measured at both 215 and 280 nm. Aggregate content is determined by calculating the percentage of monomeric material relative to higher order species. The equation used is as follows:

Aggregate Content %=Peak Area of Aggregate/(Peak Area of Monomer+Peak Area of Aggregate)*100

According to a preferred mode of practice to carry out the solubilization and precipitation protocol, the aggregated interferon mixture is solubilized in aqueous media. Then the solubilized interferon is extracted into an organic solvent. A sufficient amount of a nonsolvent is then added to the organic phase to cause the interferon to precipitate. A nonsolvent refers to a chemical that is unable to completely solubilize substantially all or causes substantially all the interferon to precipitate from a solution upon contact at 25° C. The precipitate can then be carried forward into the high pressure treatment to be described below.

Using the context of IFN-β inclusion bodies as an illustrative context, solubilization, extraction, and precipitation may be carried out as follows. Pellets comprising the inclusion bodies are added to a buffered, aqueous medium that is at a pH and/or includes a chaotrope in a manner effective to solubilize the inclusion bodies after a suitable incubation period, desirably with mixing. The pH often is alkaline to facilitate solubilization, but desirably is less than 11, often less than about 10.5, desirably less than 10 to avoid degradation of the protein material. A preferred pH may be in the range from about 7.5 to 9.5. The solubilization may occur at any suitable temperature. The temperature should not be so hot as to risk thermal degradation of the protein material. The solubilization may proceed too slowly if the solubilization medium is too cool. Using room temperature is suitable and convenient. The period required for solubilization can vary such as from about 30 seconds to about 8 hours, desirably from about two minutes to about on hour.

One suitable solubilization buffer includes 2 to 3 grams of inclusion bodies per 5 to 100 ml of an aqueous solubilization buffer made from 2 weight percent sodium dodecyl sulfate (SDS), 20 mM Tris, pH 8.0, 2 mM EDTA, 10 mM DTT. In some representative embodiments, using about 1 g of inclusion bodies per 5 ml, 10 ml, or 20 ml of the solubilization buffer, respectively is used. EDTA refers to ethylenediamine tetraacetic acid and is a strong chelator. DTT (dithiothrietol) is a reducing agent useful for disrupting disulfide bonds. Solubilization of IFN-β inclusion bodies in this buffer occurred in about 30 minutes at room temperature.

In an embodiment of the present invention, SDS is not used in the process for preparing a composition comprising nonglycosylated interferon to minimize the presence of inclusion bodies and aggregated nonglycosylated interferon. In another embodiment, the final pharmaceutical composition is substantially free of SDS. In another embodiment, the final pharmaceutical composition is substantially free of HSA.

After the IFN-β material is solubilized, it is extracted into an organic solvent. This may be accomplished in some embodiments by adding from about one to about 10, desirably from one to about four volumes of the organic solvent per volume of the solubilization buffer. The resulting admixture is thoroughly mixed. The admixture is then allowed and/or caused to settle into two phases. For instance, centrifugation may be used to assist the formation of separate aqueous and organic layers. The organic layer containing the IFN-β material can then be carefully separated from the aqueous phase. A precipitate may form at the interface between the two layers and/or at the bottom of the settling vessel. This precipitate may be discarded. Optionally, the organic phase may be washed one or more additional times with water to further upgrade the purity of the organic phase. In washing the organic phase, care should be practiced to avoid using so much aqueous material so as to risk causing precipitation of the solubilized IFN-β. Similarly, the aqueous phase may be extracted one or more additional times with organic solvent to recover additional amounts of the solubilized interferon, if desired.

The extraction helps to upgrade the purity of the interferon material. In the case of IFN-β inclusion bodies obtained from E. coli host cells, for instance, these tend to include an impurity load including a significant amount of water-soluble and other proteins, e.g., E. coli contaminant proteins. When the IFN-β is extracted into the organic solvent, these water-soluble proteins tend to remain in the aqueous phase and/or appear as the precipitate mentioned above that appears between the two phases and/or at the bottom of the settling vessel. Water soluble constituents of the aqueous buffer system also tend to stay in the aqueous phase.

A wide variety of organic solvents may be used to carry out the extraction. These include aliphatic alcohols, including butanol and sec-butanol, combinations of these, and the like. The use of sec-butanol for IFN-β inclusion bodies is preferred.

The extracted IFN-β is next precipitated from the organic phase to separate it from the butanol phase and increase the purity of the IFN-β preparation. Precipitation is readily carried out by adding a sufficient amount of a nonsolvent to the organic phase to cause the precipitation to occur. In some embodiments, this may involve adding from about one to about ten, desirably from about one to about four volumes of the nonsolvent per volume of the organic phase.

The resulting admixture is thoroughly mixed and allowed to sit for a suitable incubation period such as from about 30 seconds to 48 hours, desirably at least about ten minutes to about 8 hours. The admixture may be chilled to assist precipitation, such as at a temperature in the range from just above the freezing temperature of the admixture to about 15° C., desirably 2° C. to 5° C. The resulting precipitate may be recovered using any suitable technique or combination of techniques, such as centrifugation, filtration, and the like. If the precipitated IFN-β is not used immediately, it may be stored. Storage may occur by suspending the precipitate in a minimal amount of ultrapure (water for injection standard and endotoxin free) water, e.g., 2 to 3 mg/ml and then storing at a temperature below about 0° C., such as −10° C. or less, even −15° C. or less. By storing the precipitated interferon material in water, the entire stored admixture can be added to the refolding admixture described below in those embodiments of the invention in which high pressure refolding is practiced with aqueous media, avoiding the need to isolate the interferon from the storage water.

A wide range of such nonsolvents may be used to cause precipitation. Examples include methanol, ethanol, isopropanol, acetonitrile, organic acid such as acetic acid, acetone, MEK, combinations of these, and the like. Methanol is preferred. It has been found that the nature of the nonsolvent used for precipitation can have a significant impact upon the yield of disaggregated and refolded protein obtained from high pressure treatment. Specifically, it has been found that less hydrophobic perturbants of the organic phase tend to yield interferon that is more amenable to high pressure refolding. For instance, in a series of experiments in which identical high pressure refolding followed precipitation by methanol, ethanol, isopropanol, acetonitrile, and acetic acid (pH 5.0), refolding yields of about 42%, 34%, 31%, 38%, and 7% were obtained, respectively.

The reason for these differences in yield as a function of precipitating solvent are unknown, but a rationale can be suggested. Without wishing to be bound, the advantage of the more polar nonsolvents could be that these produce aggregated structures that have a higher propensity of hydrophobic contacts. Accordingly, the use of nonsolvents that are sufficiently polar so as to be fully water soluble at room temperature when equal volumes of the nonsolvent and water are mixed together is preferred. Methanol is preferred. As used in this specification, the term "methanol IFN-β precipitate" shall refer to IFN-β inclusion bodies solubilized in aqueous media, extracted into sec-butanol, and precipitated via addition of methanol as described herein.

The first step of solubilizing the interferon into an extraction solvent such as sec-butanol may be viewed as a hydrophobic ion-pairing step (Meyer J D, Manning M C *Hydrophobic ion pairing: Altering the solubility properties of*

*Biomolecules*, PHARMACEUTICAL RESEARCH 15 (2): 188-193 FEB 1998). This step in one illustrative embodiment uses sodium dodecyl sulfate as a hydrophobic ion-paring agent. See U.S. Pat. No. 5,981,474.

This ion-pairing couple in preferred embodiments later is exchanged for a zwitterionic ion in the high pressure refolding step. In view of this relationship between the extraction and the refolding steps, the yield of interferon beta solubilization may be increased in some embodiments by one or more of: a) more carefully controlling the concentration of the sodium dodecyl sulfate or similar agent so as to match stoichiometrically the number of positive charges found on interferon beta at the relevant pH conditions for the solubilization step when the interferon is first solubilized in aqueous media prior to extraction; b) modulating the pH of the solution from which the interferon is extracted so as to control the number of these positive charges on interferon beta; c) using other ion-pairing agents (e.g., sodium hexyl sulfate, sodium octyl sulfate, sodium bis(2-ethylhexyl)succinate), and/or d) changing the strength of the solvent itself, (e.g., by substituting iso-octane, DMSO etc. for sec-butanol).

The precipitation step involves adding a miscible antisolvent such as methanol to the solution of hydrophobic, ion-paired interferon dissolved in the extraction solvent such as sec-butanol. Without wishing to be bound by theory, it is believed that the resulting change in polarity of the admixture causes the solubility of the hydrophobic ion pair to decrease until a supersaturated solution results and the complex precipitates. From classical nucleation and growth kinetics (A. D. Randolph and M. A. Larson, Theory of Particulate Processes (second ed.), Academic Press, Inc., San Diego (1988)), the resulting particle size distribution of precipitated interferon-beta/SDS ion pairs will be determined by the degree of supersaturation, which in turn controls both nucleation and growth kinetics. In preferred embodiments, the precipitation step may be improved by optimizing the precipitation yield and particle size distribution through one or more of a) using other agents besides SDS (e.g., sodium hexyl sulfate, sodium octyl sulfate, sodium bis(2-etheylhexyl)succinate) which will alter the equilibrium solubility of the respective ion-paired complexes in the extraction solvent and hence modify the resulting equilibrium solubility, supersaturation, particle size distribution, and final yield; and/or b) modifying and controlling the rate of addition of antisolvent to the solution containing the ion pair. This will determine the supersaturation-time profile, and thus the particle size distribution.

The final particle size distribution impacts suitability for commercial scale embodiments. The sedimentation rate of a particle is proportional to the square of the particle size. Thus, large particles settle much faster than small ones. Large particles that settle to the bottom of a pressure vessel may in turn reduce refolding yields (in practical effect, this would involve trying to refold at a higher local concentration of protein). Large particles are produced when growth kinetics are faster than nucleation kinetics, and are favored by poor mixing of solvent and antisolvent. This is a problem that happens in larger scale processes. Better control of mixing and higher intensity mixing during antisolvent precipitation is likely to result in a shift of the particle size distribution to smaller sizes that are easier to resuspend, stay suspended longer, and that will result in higher refolding yields.

The present invention uses one or more improved high pressure techniques to accomplish interferon disaggregation and refolding. These improved techniques may be advantageously used singly or in combination to obtain improved refolding yields of interferon. These techniques, singly or in combination, are particularly advantageously used after carrying out the solubilization and precipitation protocol described above. Glycosylated forms of IFN-β (IM administration) have tended to have a significant half life advantage over non-glycosylated versions of IFN-β (subcutaneous (SQ) or sometimes SC) administration). Surprisingly, use of a solubilization and precipitation protocol allows refolded, non-gly-IFN-β to be prepared that has a half-life nearly comparable to that of glycosylated IFN-β and about seven times longer than a non-gly-IFN-β commercially available under the trade designation BETASERON (SQ administration). In an embodiment of the present invention, a composition of non-glycosylated IFN-β is provided that is sufficiently free of aggregates and/or inclusion bodies so that the non-glycosylated IFN-β has a terminal half-life in non-naïve rhesus monkeys that is greater than about 10 hours, preferably greater than about 15 hours, and more preferably greater than about 22 hours. In an embodiment of the present invention, a composition of non-glycosylated IFN-β is provided that is sufficiently free of aggregates and/or inclusion bodies so that the non-glycosylated IFN-β has a terminal half-life in all primates that is greater than about 10 hours, preferably greater than about 15 hours, and more preferably greater than about 22 hours. In an embodiment of the present invention, a composition of non-glycosylated IFN-β is provided that is sufficiently free of aggregates and/or inclusion bodies so that the non-glycosylated IFN-β has a terminal half-life humans that is greater than about 10 hours, preferably greater than about 15 hours, and more preferably greater than about 22 hours.

Additionally, glycosylated forms of IFN-β have also tended to have a peak plasma concentration advantage over nongly-IFN-β. Surprisingly use of a solubilization and precipitation protocol allows nongly-IFN-β to be prepared that has a peak plasma concentration comparable to that of glycosylated material and about ten times greater than commercially available non-gly-IFN-β commercially available under the trade designation BETASERON. In short, use of the solubilizing and precipitating protocol prior to a high pressure refolding treatment helps to provide nongly-IFN-β that has performance characteristics generally associated only with the glycosylated versions.

In an embodiment of the present invention, a composition of non-glycosylated IFN-β is provided that is sufficiently free of aggregates and/or inclusion bodies so that the non-glycosylated IFN-β has greater than about 50% of maximal known specific activity, more preferably greater than about 70% of maximal known specific activity, and most preferably greater than about 80% of maximal known specific activity.

In an embodiment of the present invention, a composition of non-glycosylated IFN-β is provided that is sufficiently free of aggregates and/or inclusion bodies so that the non-glycosylated IFN-β has a biological activity of greater than 40 MIU/mg, more preferably greater than about 50 MIU/mg and most preferably greater than about 60 MIU/mg. For purposes of the present invention, biological activity is determined by conducting a bioassay using A549 cells and EMC viral challenge.

In an embodiment of the present invention, a composition of non-glycosylated IFN-β, is provided that is sufficiently free of aggregates and/or inclusion bodies so that the composition is not immunogenic, whereby no antibodies against the IFN-β preparation are developed.

In an embodiment of the present invention, a composition of non-glycosylated IFN-β is sufficiently free of aggregates and/or inclusion bodies so that the composition is stable at 4° C. and having less than or equal to about 0.5% aggregates at 4 weeks. In other embodiments, the composition is stable at 4° C. and having less than or equal to about 0.5% aggregates at 2 months, 4 months, 6 months, 8, months, 10 months or 12 months. In another embodiment, the composition is sufficiently free of aggregates and/or inclusion bodies so that the composition is stable at 40° C. at 4 weeks.

As a first step for carrying out high pressure refolding, the aggregated interferon is suspended in a liquid carrier to provide a suitable refolding admixture. Most desirably the liquid carrier is aqueous and is obtained from ingredients comprising ultrapure water. The concentration of the interferon in the liquid material may vary over a wide range. If the concentration is too low, then the equipment used for high pressure refolding is being underutilized and throughput for the given resources used to process the concentration at issue may be less than would be desired. On the other hand, if the concentration of the interferon is too high, then re-aggregation may tend to occur to an undue degree or refolding yields may be too low due to solubility limits. Balancing such concerns, using from about 0.05 mg/ml to about 2 mg/ml, more desirably 0.1 to about 3 mg/ml, most desirably 0.5 g/ml of interferon is suitable.

The refolding admixture desirably includes one or more additional ingredients and/or characteristics. Firstly, the admixture desirably has an alkaline pH. However, if the pH is too high, the risk of degradation of the interferon may be too high. Accordingly, it is preferred that the pH of the admixture be in the range from about 7.5 to 10, desirably about 8 to about 9.5. A pH of 9 is most preferred at present. It has been observed that the yield of refolded protein tends to increase with increasing pH. A pH value of about 9 strikes a good balance between achieving such higher yields and minimizing undue risk of protein degradation.

Buffering agents can be used in the admixture to help maintain a desired pH value or range. A wide range of inorganic and/or organic buffer systems may be used in accordance with conventional practices. Examples include phosphate, carbonate, citrate, Tris, MOPS, MES, HEPES, CAPS, CHES, and the like. The use of CAPS at pH 10 and CHES for pH 9 are preferred. The use of CHES is more preferred.

The refolding of non-glycosylated interferon proteins such as nongly-IFN-β generally involves the formation of one or more disulfide bonds. Accordingly, the refolding admixture desirably includes oxidizing/reducing agents (e.g. disulfide chemistry) that help promote the formation of the disulfide bonds. These can include agents that work mainly through an oxidation/reduction mechanism, such as when using the combination of iodosobenzoic acid oxidizing agent (40 uM) and DTT reducing agent (2 mM). These can also include suitable pairs of disulfide shuffling agents such as the cysteine/cystine pair, the reduced glutathione (GSH)/oxidized glutathione (GSSH) pair, the cysteamine/cyamine pair, combinations of these, and the like. The disulfide shuffling agents may be used at any suitable concentration such as 0.3 mM oxidized to 1.3 mM reduced.

The type of disulfide chemistry used in the refolding admixture can impact the refolding yield significantly, although the impact depends upon whether solubilization and precipitation are used prior to high pressure treatment. For example, when using high pressure to disaggregate and refold nongly-IFN-β inclusion bodies without solubilization and precipitation, the use of oxidative agents such as iodosobenzoic acid and DTT provided higher refolding yields than did using disulfide shuffling agents, holding all other conditions constant. For example, under one illustrative set of test conditions described in the Examples below, the use of iodosobenzoic acid and DTT provided refolding yield of nearly 25%, whereas the next best performing disulfide shuffling reagent provided a yield under 20%. Of the disulfide shuffling agents, the use of cysteine/cystine provided the highest yields (nearly 20%), which was more than double the yields provided by GSH/GSSH and cysteamine and cystamine, the other pairs tested.

In contrast, when high pressure refolding follows solubilization and precipitation, the use of disulfide shuffling agents tend to provide better yields. The effect appears to be relatively insensitive over the concentration range of these agents useful for promoting disulfide bond formation. In particular, the cysteine/cystine pair provides dramatically better yields than the other disulfide shuffling pairs, providing yields as high as about 51%. In contrast, the second best performing shuffling agent pair was GSH/GSSH, providing yields of about 37%, or nearly 20% less. The use of iodosobenzoic acid and DTT provided yields of only about 4% in this environment, which is surprising since this pair performed best in the absence of solubilization and precipitation. The reasons for this shift in performance are unknown, but the shift provides further evidence that the solubilization and precipitation protocol yields aggregates with dramatically different properties and perhaps different structures as well.

The refolding admixture may also include one or more surfactants used in conventional amounts. A surfactant is a compound that reduces the surface tension of the aqueous liquid carrier. Surfactants may be anionic, cationic, nonionic, zwitterionic, or mixtures of these. Representative examples include t-octylphenoxypolyethoxy-ethanol; polyoxyethylene sorbitan; sodium dodecyl sulfate; cetylpyridinium chloride; deoxycholate; sodium octyl sulfate; sodium tetradecyl sulfate; polyoxyethylene ether; sodium cholate; octylthioglucopyranoside; n-octylglucopyranoside; alkyltrimethylammonium bromides; alkyltrimethyl ammonium chlorides; sodium bis(2-ethylhexyl)sulfosuccinate; beta-oxtyl-glucopyraniside (BOG, a nonionic surfactant), is 3-[(3-Cholamidopropyl)dimethylammonio]-1-propanesulfonate (CHAPS, a zwitterionic surfactant), combinations of these, and the like. Representative examples of suitable surfactants are also commercially available under trade designations including Zwittergent SB 3-14; Brij-35; Tween-20; Pluronic F-68; Triton X-100; and NDSB-201.

In the context of the present invention, it has been found that using zwitterionic surfactants helps to provide the highest refolding yields, particularly when used with respect to solubilized and precipitated, nongly-IFN-β. The use of a zwitterionic surfactant was the most effective surfactant for refolding non-glyIFN-β from inclusion bodies including those embodiments in which solubilization and precipitation occurred prior to high pressure refolding and those embodiments where it did not. In one preferred refolding admixture, refolding yields of over 45% were obtained using a zwitterionic surfactant. The closest performing surfactant was a cholate salt, which provided yields of about 38%. All other surfactants tested provided yields of about 20% or less. A particularly preferred zwitterionic surfactant is commercially available under the trade designation Zwittergent SB 3-14 which is a zwitterion detergent that has been shown to have a strong binding affinity and prevent aggregation in proteins in some applications, including the purification of IFN-β. Hannam, C., G. L. Lange, et al. (1998). *Analytical Biochemistry* 258(2): 246-250. Kuroda, Y., Y. Maeda, et al. (2003). *Journal Of Peptide Science* 9(4): 212-220. Basu, A., K. Yang, et al. (2006). "*Bioconjugate Chemistry* 17(3): 618-630; Russell-Harde.

It is also preferred to use a cholate salt as a surfactant, as use of such cholate salts provided substantially higher refolding yields than other classes of surfactants. Sodium cholate is preferred. The refolding admixture optionally may include one or more additional ingredients such as preferential excluders or chaotropes.

In a representative methodology for making supplies of refolding admixture, the disulfide chemistry materials are usually prepared fresh. One illustrative reagent pair is a 100 mM cysteine aqueous solution containing 0.018 g/ml and a 100 mM cystine solution containing 0.024 g/1.0 ml in 200 mM NaOH. Next, all the ingredients to be included in the reagent are loaded into a suitable vessel, such as a 50 ml bottle or the like. The bottle can be topped off with water, buffer, and surfactant at concentrations to match the admixture to ensure that no air is present. See Assignee's co-pending U.S. Provisional Application titled DEVICES AND METHODS FOR HIGH PRESSURE REFOLDING OF PROTEINS, having Ser. No. 60/739,094 filed Nov. 21, 2005 in the name of one or more inventors including Matthew B. Seefeldt. The preparation optionally may occur under the protection of an inert atmosphere, such as nitrogen, argon, or the like, to help protect the ingredients from the ambient oxygen.

One illustrative refolding admixture includes 0.5 mg/ml of interferon in an aqueous liquid carrier including 50 mM CAPS (pH 0), 1.3 mM cysteine, 0.3 mM cystine, and 0.05 weight percent Zwittergent SB 3-14 surfactant. Another illustrative admixture includes 50 mM CHES (pH 9), 1.3 mM cysteine, 0.3 mM cystine, and 0.05 weight percent Zwittergent SB 3-14 surfactant. Another illustrative refolding admixture includes 50 mM CHES (pH 9), 1.3 mM cysteine, 0.3 mM cystine, and 1.3% NaCholate. In all of these solutions, the refolding time and refolding temperature can all be varied such as from 0.5 to 24 hours, desirably 2 hours and 0° C. to 25° C., respectively, in illustrative embodiment.

The stock solutions of refolding admixture may be subjected to high pressure refolding treatment directly to accomplish disaggregation and refolding or may be used to prepare samples to be subjected to such high pressure treatment. For instance, the stock solutions can be used to create a suitable refolding sample in a suitable vessel, such 500 μL samples mixed in common polypropylene microcentrifuge centrifuge tubes. The mixed samples are then placed into sealed syringes and pressure treated using techniques as described in Seefeldt, M. B., J. Ouyang, et al. (2004). "High-pressure refolding of bikunin: Efficacy and thermodynamics." *Protein Science* 13(10): 2639-2650; and Seefeldt, M. B., J. Ouyang, et al. (2004). "High-pressure refolding of bikunin: Efficacy and thermodynamics." *Protein Science* 13: 2639-2650. Care is taken to help ensure that insoluble protein aggregate in the sample is pipetted correctly without undue filtering or other loss from the Eppendorf brand tubes. The concentration of protein present in the inclusion body precipitate is obtained by a reduced RP-HPLC method. The RP-HPLC conditions for analyzing refolds are as follows:

| HPLC: | Agilent HP 1100 |
|---|---|
| Column: | C3 Zorbax with guard column 300SB3.5 um 4.6 × 150 mm |
| Solvents: | A: Water, 0.1% TFA |
| | B: Acetonitrile, 0.1% TFA |
| Flow Rate: | 1 ml/min |
| Temp: | 30° C. |
| Injection: | 20 μl |
| Absorbance: | 215 nm, 280 nm |

| Time (min) | % B |
|---|---|
| 0 | 27 |
| 1 | 45 |
| 36 | 56 |
| 37 | 100 |
| 40 | 27 |

The protein concentration of a precipitate following solubilization and precipitation is obtained by taking an absorbance reading at 280 nm prior to precipitation and calculating the protein concentration using an extinction coefficient of 1.5.

Reducing and non-reducing SDS-PAGE (Sodium dodecyl sulfate-polyacrylamide gel electrophoresis) is used to examine the purity and disulfide content of pressure solubilized IFN-β. Approximately 5 μg of protein from the processed supernatant is added to an appropriate volume of 2× SDS-PAGE sample buffer (Invitrogen, Carlsbad, Calif.). The SDS-protein mixture is heated for five minutes at 100° C. 4-20% Novex Tris-glycine precast gels are used (Invitrogen, Carlsbad, Calif.), with 400 ml of diluted 10× Tris-glycine running buffer (BioRad, Hercules, Calif.). Gels are run for fifty minutes, and staining is conducted with methanol/acetic acid-free Coomassie blue for total protein analysis (BioRad, Hercules, Calif.).

Generally, the refolding sample is subjected to a pressure that is sufficiently high to cause at least a portion of an aggregated interferon mixture to undergo disaggregation and refolding. Although refolding samples may include a chaotrope, the present invention is distinguished from conventional methods that rely mainly upon relatively high concentrations of a strong chaotrope to accomplish disaggregation and refolding. In representative embodiments, the pressure used may be in the range from about 1000 bars to about 10,000 bars, or from about 1000 bars to about 5000 bars. Refolding yields tend to be greater with increasing pressure up to an optimum pressure range beyond which increasing pressure will increasingly tend to inhibit refolding. Selecting a suitable pressure within this range will depend upon factors including the formulation of the refolding sample, whether the aggregated protein mixture or aggregated protein being treated was subjected to a solubilization and precipitation treatment, the pressure stability of the native, monomeric protein of interest, the temperature, and the like.

When solubilization and precipitation is not used and the formulation does not include a zwitterionic surfactant and/or a cholate salt surfactant, higher pressures greater than 2500 bars, even above 2800 bars, and even above about 3000 bars and up to about 5000 bars, preferably up to about 4500 bars would be more suitable. In these embodiments, using a pressure in the range from 3000 bars to 3500 bars, e.g., 3200 bars, is most desirable.

When solubilization and precipitation is not used, but the formulation includes a zwitterionic surfactant and/or a cholate salt, a wider range of pressures can accomplish at least some degree of disaggregation and refolding. In these embodiments, using a pressure in the range of from about 1200 to about 5000 bars, preferably 2000 bars to 4500 bars, more preferably 2800 to 3800 bars, e.g., 3200 or 3500 bars, is desirable.

When solubilization and precipitation is used, particularly in combination with a zwitterionic surfactant and/or a cholate salt, a much wider range of high pressures leads to at least some disaggregation and refolding, although higher pressures are still preferred. In these embodiments, the pressure may be in the full range from 1000 bars to 10,000 bars, or in another embodiment from 1000 bars to 5000 bars, but desirably is in the range from 2000 bars to 4500 bars, more desirably 2800 to 3800 bars, e.g., 3200 or 3500 bars.

The level of refolding pressure impacts refolding yields. Using the Preferred Refolding Reagent A to carry out refolding of IFN-β inclusion bodies without pre-treating via solubilization and precipitation, yields were nearly 20% at 3500 bars, but only about 6% at 2000 bars. Note from Example 2, that yields at 2000 bars were 0% without solubilization and precipitation and without a zwitterionic or cholate salt surfactant. Thus, using a zwitterionic and/or cholate salt surfactant allows refolding to occur in the first instance at 2000 bars in this representative embodiment, and then increasing the pressure to 3500 bars almost quadruples the yield. The impact of solubilization and precipitation in combination with high pressure is also dramatic. By first solubilizing and precipitating IFN-β inclusion bodies and then refolding in Preferred Refolding Reagent A at 3500 bars, the yield more than doubles to nearly 45%.

In the course of a treatment it is desirable to ramp the pressure up to the desired incubation pressure(s) over a period of time to avoid undue generation of thermal energy and/or otherwise degrade the interferon if the pressure change were to be too quick, allow the sample to incubate at the elevated pressure(s) for a period of time, and then ramp the pressure down over a suitable time period also to avoid undue aggregation or other degradation if the pressure were to be too quick. For instance, the pressure may be increased from ambient to the desired incubation pressure in one or more stages occurring over a period ranging from 3 minutes to 48 hours, desirably ten minutes to 8 hours. In one mode of practice, linearly increasing the pressure up to 3500 bars in a period of 32 minutes is suitable. In another mode of practice, linearly increasing the pressure up to 3200 bars in a period of 32 minutes is suitable.

A wide range of incubation periods may be used to accomplish at least some degree of disaggregation and refolding. Representative time periods range from 0.5 seconds to 48 hours, desirably 2 minutes to 24 hours, more desirably ten minutes to 24 hours, most preferably 2 to 4 hours. It is believed that shorter periods lead to lower yields due to the kinetics of aggregate dissociation. It is also believed that a maximum yield is reached due to thermodynamic equilibrium effects, inasmuch as thermodynamic equilibrium has been shown to be a factor in protein refolding. Seefeldt MB, Crouch C, Kendrick B, Carpenter, J F, and Randolph, T W (2007) "Specific volume and adiabatic compressibility measurements of native and aggregated recombinant human interleukin-1 receptor antagonist: Density differences enable pressure-modulated refolding" BIOTECHNOLOGY AND BIOENGINEERING 98 (2): 476-485 Oct. 1 2007. In one embodiment, a 2 hour incubation period is used to treat IFN-β inclusion bodies that, prior to high pressure treatment, were solubilized in aqueous buffer, extracted into butanol or sec-butanol, and precipitated using methanol.

The pressure treatment may occur at a wide range of temperatures. If the temperature is too low, then the kinetics of aggregate dissociation and refolding can be slowed as well as the disruption of hydrogen bonds. Thermal degradation of the interferon may occur if the temperature is too high. Balancing such concerns, representative modes of practice may carry out high pressure treatment at a temperature in the range from about 0 to about 50° C., more desirably 0 to about 30° C. In many embodiments, a temperature of 25° C. is suitable. Carrying out the pressure treatment at cooler temperatures, e.g., 4° C., has been observed to increase yield and purity in some embodiments. The temperature is the water bath temperature in which the pressure vessel is held during the high pressure treatment.

Thus, in an embodiment of the present invention, a method of preparing a composition comprising nonglycosylated interferon to minimize the presence of inclusion bodies and aggregated nonglycosylated interferon, comprising the steps of:
a) solubilizing the aggregated interferon;
b) precipitating the solubilized interferon;
c) incorporating the precipitated interferon into a refolding admixture; and
d) applying an amount of pressure to the refolding admixture incorporating the interferon effective to refold at least a portion of the interferon to form a composition comprising nonglycosylated interferon;
wherein the resulting composition comprises less than about 5 weight percent of protein aggregation.

Another embodiment comprises the steps of:
a) incorporating the aggregated interferon into a refolding admixture, said admixture comprising a zwitterionic surfactant; and
b) applying an amount of pressure to the refolding admixture incorporating the interferon effective to refold at least a portion of the interferon;
wherein the resulting composition comprises less than about 5 weight percent of protein aggregation.

Another embodiment comprises the steps of:
a) incorporating the aggregated interferon into a refolding admixture, said admixture comprising a disulfide shuffling reagent; and
b) applying an amount of pressure to the refolding admixture incorporating the interferon effective to refold at least a portion of the interferon;
wherein the resulting composition comprises less than about 5 weight percent of protein aggregation.

Another embodiment comprises the steps of:
a) solubilizing the aggregated interferon;
b) precipitating the solubilized interferon;
c) incorporating the precipitated interferon into a refolding admixture comprising a zwitterionic surfactant and a disulfide shuffling reagent; and
d) applying an amount of pressure to the refolding admixture incorporating the interferon effective to refold at least a portion of the interferon;
wherein the resulting composition comprises less than about 5 weight percent of protein aggregation.

Another embodiment comprises the steps of:
a) incorporating the aggregated interferon into a refolding admixture; and
b) applying over 3000 bars of pressure to the refolding admixture incorporating the interferon in a manner effective to refold at least a portion of the interferon;
wherein the resulting composition comprises less than about 5 weight percent of protein aggregation.

Another embodiment comprises the steps of:
a) solubilizing the aggregated interferon in an aqueous medium;
b) extracting the solubilized interferon into an organic solvent;
c) precipitating the solubilized interferon;
d) incorporating the precipitated interferon into a refolding admixture; and
e) applying an amount of pressure to the refolding admixture incorporating the interferon effective to refold at least a portion of the interferon;
wherein the resulting composition comprises less than about 5 weight percent of protein aggregation.

It will be appreciated that all combinations of these various methods are specifically contemplated, including, for example, the use of specific surfactants and/or shuffling agents optionally in combination with specific pressure conditions as described herein. Further, pharmaceutical compositions comprising a therapeutically effective amount of an interferon, said interferon composition being made according to each of these possible methods as described herein are specifically contemplated.

After high pressure treatment, the interferon product mixture is desirably purified to remove various impurities. These impurities include E. coli proteins where the interferon is recombinant and obtained from E. coli host cells, aggregated interferon, a higher molecular weight IFN-β species that appears to lack a desired disulfide bond as observed by SDS-PAGE and RP-HPLC analyses, endotoxins, and the like.

Chromatography using a series of three columns is an example of one illustrative purification technique. According to such a technique, so-called Blue Sepharose, Cu Imac, and S- or CM-Sepharose columns. These can be used in any order. The Blue column captures the interferon out of the refolding solution. The interferon is then eluted from the column. The other two columns help to upgrade the impurity of the interferon. The Cu-IMAC column functions in one regard as a metal binding column to help remove metal impurities bound to the interferon by chelation or the like. The S- or CM-Sepharose column functions via cationic exchange to separate the interferon from impurities such as endotoxins based upon charge. The Cu IMAC column helps remove chelated metal impurities as well as residual endotoxins. Additionally, aggregates and E. coli proteins elute prior to the main IFN-β peak. Other columns such as Zinc IMAC columns could also be used. CM- and S-Sepharose columns seem to offer similar performance. Higher salt concentration may be required when the column is run at lower pH values. A surfactant additive also proved helpful to enhance performance. Examples include the surfactants identified above. Polysorbate 20 (available under the trade designation TWEEN 20) or Polysorbate 80 (available under the trade designation TWEEN 80) are presently preferred. The S-Sepharose column offers an opportunity to add a final polishing step to upgrade the purity of the interferon. Endotoxins and E. coli proteins can be further removed. Representative conditions for carrying out purification using these columns are described in the Examples, below.

The Blue Sepharose and the Cu-IMAC columns have the potential of leaching column components into the final protein pool. Also, it would be convenient to use buffers during chromatographic purification that use FDA-approved buffer components such as the Tween-20 ingredient. Accordingly, alternative modes of practice of purification involve a tertiary column purification that avoids the use of Blue Sepharose and IMAC-$Cu^{2+}$ columns. The Examples below show how this procedure is carried out with respect to this column.

Following chromatography, the purified interferon can be incorporated into any one or more desired pharmaceutical compositions. The pharmaceutical compositions may be sterilized such as by membrane filtration and may be stored in unit-dose or multi-dose containers such as sealed vials or ampoules. The pharmaceutical compositions are used to administer the interferon in pharmaceutically effective amounts. By "pharmaceutically effective amount" is intended an amount that is useful in the treatment, prevention, or diagnosis of a disease or condition, or symptoms thereof. Typical routes of administration include, but are not limited to, oral administration, nasal delivery, pulmonary delivery, and parenteral administration, including transdermal, intravenous, intramuscular, subcutaneous, intraarterial, and intraperitoneal injection or infusion. In one such embodiment, the administration is by injection, preferably subcutaneous injection. Injectable forms of the compositions of the invention include, but are not limited to, solutions, suspensions, and emulsions. Typically, a therapeutically effective amount of IFN-β comprises about 0.01 µg/kg to about 5 mg/kg of the composition, preferably about 0.05 µg/kg to about 1000 µg/kg, more preferably about 0.1 µg/kg to about 500 µg/kg, even more preferably still about 0.5 µg/kg to about 30 µg/kg per dose and/or on a daily basis.

The pharmaceutical compositions of the present invention, particularly those including nongly-IFN-β or variants thereof, are useful in the diagnosis, prevention, and treatment (local or systemic) of clinical indications responsive to therapy with this polypeptide. Such clinical indications include, for example, disorders or diseases of the central nervous system (CNS), brain, and/or spinal cord, including Alzheimer's disease, Parkinson's disease, Lewy body dementia, multiple sclerosis, epilepsy, cerebellar ataxia, progressive supranuclear palsy, amyotrophic lateral sclerosis, affective disorders, anxiety disorders, obsessive compulsive disorders, personality disorders, attention deficit disorder, attention deficit hyperactivity disorder, Tourette Syndrome, Tay Sachs, Nieman Pick, and schizophrenia; nerve damage from cerebrovascular disorders such as stroke in the brain or spinal cord, from CNS infections including meningitis and HIV, from tumors of the brain and spinal cord, or from a prion disease; autoimmune diseases, including acquired immune deficiency, rheumatoid arthritis, psoriasis, Crohn's disease, Sjogren's syndrome, amyotropic lateral sclerosis, and lupus; and cancers, including breast, prostate, bladder, kidney and colon cancers. Administration of IFN-β or its muteins to humans or animals may be delivered orally, intraperitoneally, intramuscularly, subcutaneously, intravenously, intranasally, or by pulmonary delivery as deemed appropriate by the physician.

According to one formulation option, the purified interferon is incorporated into pharmaceutical compositions suitable for subcutaneous injection such as a solution, suspension, or emulsion. Such formulations generally comprise a pharmaceutically acceptable liquid carrier. By "pharmaceutically acceptable liquid carrier" is intended a carrier that is conventionally used in the art to facilitate the storage, administration, and/or the healing effect of the therapeutic ingredients. A carrier may also reduce any undesirable side effects of the IFN-β with low or no toxicity to the patient. A suitable carrier should be stable, i.e., substantially incapable of reacting with other ingredients in the formulation. It should not produce significant local or systemic adverse effects in recipients at the dosages and concentrations employed for treatment. Such carriers are generally known in the art. Ultrapure water (WFI, endotoxin free) is an exemplary liquid carrier.

The formulations for subcutaneous injection desirably have a pH of about 3.0 to about 5.0, preferably about 3.0 to about 4.5, more preferably about 3.0 to about 4.0, still more preferably about 3.5 to about 4.0, most preferably about 4.0. At this pH, the IFN-β is soluble, stable, and resistant to aggregate formation.

The composition also desirably comprises a buffer in an amount that is sufficient to maintain the pH of the pharmaceutical composition within plus or minus 0.5 units of a specified pH, and which desirably is present at a concentration no greater than about 60 mM, preferably 15 mM to about 50 mM. Suitable buffers that can be used to prepare the in which the IFN-β is solubilized include, but are not limited to, glycine, aspartic acid, succinate salt, citrate salt, formate salt, acetate salt, glutamic acid, histidine, imidazole, and phosphate. Sodium salts of succinate, citrate, formate, and acetate are preferred.

The formulations may also comprise a tonicity modifying agent in an amount sufficient to render the compositions isotonic with body fluids. Tonicity is a measure of effective osmolarity or effective osmolality. Tonicity is a property of a solution in reference to a particular membrane, and is equal to the sum of the concentrations of the solutes which have the capacity to exert an osmotic force across that membrane. Tonicity, also, depends on solute permeability. Permeant solutes generally do not affect tonicity; impermeant solutes generally do affect tonicity. If a cell is placed in a hypotonic solution (one of lower tonicity than the cell contents), the water concentration is greater outside the cell and so osmosis produces a net movement of water into the cell. If the medium is isotonic, the water concentration is the same on either side of the cell membrane, and there is no net movement of water. If the medium is hypertonic, the water concentration inside the cell is greater. This leads to net movement of water out of the cell. Animal cells shrivel up; plant cells become plasmolysed (the cell membrane pulls away from the cell wall in places as the cytoplasm shrinks).

Nonionic tonicity modifying agents are preferred. The compositions can be made isotonic with a number of tonicity modifying agents ordinarily known to those in the art. These are typically carbohydrates of various classifications (see, for example, Voet and Voet (1990) *Biochemistry* (John Wiley & Sons, New York). Monosaccharides classified as aldoses such as glucose, mannose, arabinose, and ribose, as well as those classified as ketoses such as fructose, sorbose, and xylulose can be used as non-ionic tonicifying agents in the present invention. Disaccharides such a sucrose, maltose, trehalose, and lactose can also be used. In addition, alditols (acyclic polyhydroxy alcohols) such as glycerol, mannitol, xylitol, and sorbitol are non-ionic tonicifying agents useful in the present invention. The most preferred non-ionic tonicifying agents are trehalose, sucrose, and mannitol, or a combination thereof. The non-ionic tonicifying agent is added in an amount sufficient to render the formulation isotonic with body fluids. When incorporated into the pharmaceutical compositions, the non-ionic tonicifying agent is present at a concentration of about 1% to about 10%, depending upon the agent used. Thus, in one embodiment, the non-ionic tonicifying agent is trehalose or sucrose at a concentration of about 8% to about 10%, preferably about 9% by weight per volume, and preferably is trehalose at this concentration. In another embodiment, the non-ionic tonicifying agent is sorbitol at a concentration of about 4% to about 6%, preferably about 5% by weight per volume.

Compositions encompassed by the invention may have as little as about 0.01 mg/ml IFN-β and as much as about 20.0 mg/ml IFN-β (weight/volume). In various embodiments, the IFN-β is present at a concentration of about 0.01 mg/ml to about 20.0 mg/ml, about 0.015 mg/ml to about 12.5 mg/ml, about 0.025 mg/ml to about 10.0 mg/ml, about 0.05 mg/ml to about 8.0 mg/ml, about 0.075 mg/ml to about 6.0 mg/ml, about 0.1 mg/ml to about 4.0 mg/ml, about 0.125 mg/ml to about 2.0 mg/ml, about 0.175 mg/ml to about 1.0 mg/ml, about 0.2 mg/ml to about 0.5 mg/ml, about 0.225 mg/ml to about 0.3 mg/ml, and about 0.25 mg/ml.

The pharmaceutical composition may additionally comprise a solubilizing agent or solubility enhancer that contributes to the protein's solubility. Compounds containing a guanidinium group, most preferably arginine, are suitable solubility enhancers for IFN-β. Examples of such solubility enhancers include the amino acid arginine, as well as amino acid analogues of arginine that retain the ability to enhance solubility of IFN-β. Such analogues include, without limitation, dipeptides and tripeptides that contain arginine. Additional suitable solubilizing agents are discussed in U.S. Pat. Nos. 4,816,440; 4,894,330; 5,004,605; 5,183,746; 5,643,566; and in Wang et al. (1980) *J. Parenteral Drug Assoc.* 34:452-462; herein incorporated by reference.

In addition to those agents disclosed above, other stabilizing agents, such as ethylenediaminetetracetic acid (EDTA) or one of its salts such as disodium EDTA, can be added to further enhance the stability of the liquid pharmaceutical compositions. The EDTA acts as a scavenger of metal ions known to catalyze many oxidation reactions, thus providing an additional stabilizing agent. Other suitable stabilizing agents include non-ionic surfactants, including polyoxyethylene sorbitol esters such as polysorbate 80 (Tween 80) and polysorbate 20 (Tween 20); polyoxypropylene-polyoxyethylene esters such as Pluronic F68 and Pluronic F127; polyoxyethylene alcohols such as Brij 35; simethicone; polyethylene glycol such as PEG400; lysophosphatidylcholine; and polyoxyethylene-p-t-octylphenol such as Triton X-100. Classic stabilization of pharmaceuticals by surfactants is described, for example, in Levine et al. (1991) *J. Parenteral Sci. Technol.* 45(3):160-165, herein incorporated by reference.

Representative formulations for subcutaneous injection include purified nongly-IFN-β of the present invention are shown in Table 1 as follows:

TABLE 1

| Sample | Buffer (25 mM) | Tonicity pH Modifier* | Surfactant (0.01%)** | Protein Concentration (mg/ml) | Fill Volume (ml) |
|---|---|---|---|---|---|
| A | Na acetate | 4.0 5% Sorbitol | PS20*** | 0.25 | 1 |
| B | Na acetate | 4.0 9% Trehalose | PS20 | 0.25 | 1 |
| C | Na acetate | 4.0 9% Trehalose | PS80 | 0.25 | 1 |
| D | Na acetate | 4.0 9% Trehalose | PS20 | 1.00 | 0.25 |
| E | Na acetate | 4.0 9% Trehalose | PS20 | 0.25 | 1 |

*Percents are percent by weight based upon the total weight of the formulation.
**Percents are percent by weight based upon the total weight of the formulation.
***PS20 is Polysorbate 20 (Tween 20);
PS80 is Polysorbate 80 (Tween 80).

For subcutaneous formulation, it is desirable that the pooled fractions from chromatographic purification are dialyzed into the formulation buffer. However, attempts to dialyze non-glycosylated-IFN-β directly into formulation buffers tend to cause significant precipitation of the protein. To avoid this, dialysis of the interferon into 10 mM HCl containing 9 weight percent trehalose has successfully provided soluble protein. A concentrated stock of buffer is added to yield the desired final formulation. In other embodiments of the invention, the pharmaceutical compositions of the invention can be prepared in a form that is suitable for pulmonary delivery and administering the preparation to the subject via pulmonary inhalation. By "pulmonary inhalation" is intended that the pharmaceutical composition is directly administered to the lung by delivering the composition in an aerosol or other suitable preparation from a delivery device into the oral or nasal cavity of the subject as the subject inhales through the oral or nasal cavity. By "aerosol" is intended a suspension of solid or liquid particles in flowing air or other physiologically acceptable gas stream. Other suitable preparations include, but are not limited to, mist, vapor, or spray preparations. Pulmonary inhalation could also be accomplished by other suitable methods known to those skilled in the art. These may include liquid instillation using a suitable device or other such methods. Pulmonary inhalation results in deposition of the inhaled protein composition in the alveoli of the subject's lungs. Once deposited, the protein may be absorbed, passively or actively, across the alveoli epithelium and capillary epithelium layers into the bloodstream for subsequent systemic distribution.

Pulmonary administration of a polypeptide or protein such as IFN-β requires dispensing of the biologically active substance from a delivery device into a subject's oral or nasal cavity during inhalation. For purposes of the present invention, pharmaceutical compositions comprising IFN-β or variants thereof are administered via inhalation of an aerosol or other suitable preparation that is obtained from an aqueous or nonaqueous solution or suspension form, or a solid or dry powder form of the pharmaceutical composition, depending upon the delivery device used. Such delivery devices are well known in the art and include, but are not limited to, nebulizers, metered-dose inhalers, and dry powder inhalers, or any other appropriate delivery mechanisms that allow for dispensing of a pharmaceutical composition as an aqueous or nonaqueous solution or suspension or as a solid or dry powder form.

Thus, the compositions of the invention for pulmonary delivery encompass liquid compositions and dried forms thereof. For purposes of the present invention, the term "liquid" with regard to pharmaceutical compositions or formulations is intended to include the term "aqueous", and includes liquid formulations that are frozen. By "dried form" is intended the liquid pharmaceutical composition or formulation is dried by techniques including freeze drying (i.e., lyophilization; see, for example, Williams and Polli (1984) *J. Parenteral Sci. Technol.* 38:48-59), spray drying (see Masters (1991) in *Spray-Drying Handbook* (5th ed; Longman Scientific and Technical, Essez, U.K.), pp. 491-676; Broadhead et al. (1992) *Drug Devel. Ind. Pharm.* 18:1169-1206; and Mumenthaler et al. (1994) *Pharm. Res.* 11:12-20), or air drying (Carpenter and Crowe (1988) *Cryobiology* 25:459-470; and Roser (1991) *Biopharm.* 4:47-53). The term "lyophilize" with regard to IFN-β pharmaceutical formulations is intended to refer to freeze drying under reduced pressure of a plurality of vials, each containing a unit dose of the interferon formulation of the present invention therein. Lyophilizers, which perform the above described lyophilization, are commercially available and readily operable by those skilled in the art. In one embodiment of the present invention, the liquid composition is prepared as a lyophilized composition.

For purposes of the present invention, the terms "solid" and "dry powder" are used interchangeably with reference to the pharmaceutical compositions suitable for pulmonary delivery. By "solid" or "dry powder" form of a pharmaceutical composition is intended the composition has been dried to a finely divided powder having a moisture content below about 10% by weight, usually below about 5% by weight, and preferably below about 3% by weight. Preferred particle sizes are less than about 10.0 µm mean diameter, more preferably less than about 7.0 µm, even more preferably about less than about 6.0 µm, even more preferably in the range of 0.1 to 5.0 µm, most preferably in the range of about 1.0 to about 5.0 µm mean diameter.

Where the liquid pharmaceutical composition is lyophilized prior to use in pulmonary delivery, the lyophilized composition desirably is milled to obtain the finely divided dry powder of particles within the desired size range noted above. Where spray-drying is used to obtain a dry powder form of the liquid pharmaceutical composition, the process is carried out under conditions that result in a finely divided dry powder of particles within the desired size range noted above. Optionally, the powders may be substantially amorphous. Similarly, if the starting pharmaceutical composition is already in a lyophilized form, the composition can be milled to obtain the dry powder form for subsequent preparation as an aerosol or other preparation suitable for pulmonary inhalation. Where the starting pharmaceutical composition is in its spray-dried form, the composition has preferably been prepared such that it is already in a dry powder form having the appropriate particle size for dispensing as an aqueous or nonaqueous solution or suspension or dry powder form in accordance pulmonary administration. For methods of preparing dry powder forms of pharmaceutical compositions, see, for example, WO 96/32149, WO 97/41833, WO 98/29096, and U.S. Pat. Nos. 5,976,574, 5,985,248, and 6,001,336.

The resulting dry powder form of the composition is then placed within an appropriate delivery device for subsequent preparation as an aerosol or other suitable preparation that is delivered to the subject via pulmonary inhalation. Where the dry powder form of the pharmaceutical composition is to be prepared and dispensed as an aqueous or nonaqueous solution or suspension, a metered-dose inhaler, or other appropriate delivery device is used. A pharmaceutically effective amount of the dry powder form of the composition is administered in an aerosol or other preparation suitable for pulmonary inhalation. The amount of dry powder form of the composition placed within the delivery device is sufficient to allow for delivery of a pharmaceutically effective amount of the composition to the subject by inhalation. Thus, the amount of dry powder form to be placed in the delivery device will compensate for possible losses to the device during storage and delivery of the dry powder form of the composition.

Following placement of the dry powder form within a delivery device, the properly sized particles as noted above are suspended in an aerosol propellant. The pressurized nonaqueous suspension is then released from the delivery device into the air passage of the subject while inhaling. The delivery device delivers, in a single or multiple fractional dose, by pulmonary inhalation a pharmaceutically effective amount of the composition to the subject's lungs. The aerosol propellant may be any conventional material employed for this purpose, such as a chlorofluorocarbon, a hydrochloro-fluorocarbon, a hydrofluorocarbon, or a hydrocarbon, including trichlorofluoromethane, dichlorodifluro-methane, dichlorotetrafluoromethane, dichlorodifluoro-methane, dichlorotetrafluoroethanol, and 1,1,1,2-tetra-fluoroethane, or combinations thereof. A surfactant may be added to the pharmaceutical composition to reduce adhesion of the protein-containing dry powder to the walls of the delivery device from which the aerosol is dispensed. Suitable surfactants for this intended use include, but are not limited to, sorbitan trioleate, soya lecithin, and oleic acid. Devices suitable for pulmonary delivery of a dry powder form of a protein composition as a nonaqueous suspension are commercially available. Examples of such devices include the Ventolin metered-dose inhaler (Glaxo Inc., Research Triangle Park, N.C.) and the Intal Inhaler (Fisons, Corp., Bedford, Mass.). See also the aerosol delivery devices described in U.S. Pat. Nos. 5,522,378, 5,775,320, 5,934,272 and 5,960,792.

Where the solid or dry powder form of the HSA-free IFN-β pharmaceutical composition is to be delivered as a dry powder form, a dry powder inhaler or other appropriate delivery device is preferably used. The dry powder form of the pharmaceutical composition is preferably prepared as a dry powder aerosol by dispersion in a flowing air or other physiologically acceptable gas stream in a conventional manner. Examples of commercially available dry powder inhalers suitable for use in accordance with the methods herein include the Spinhaler powder inhaler (Fisons Corp., Bedford, Mass.) and the Ventolin Rotahaler (Glaxo, Inc., Research Triangle Park, N.C.). See also the dry powder delivery devices described in WO 93/00951, WO 96/09085, WO 96/32152, and U.S. Pat. Nos. 5,458,135, 5,785,049, and 5,993,783, herein incorporated by reference.

The dry powder form of the HSA-free pharmaceutical composition comprising IFN-β or biologically active variant thereof can be reconstituted to an aqueous solution for subsequent delivery as an aqueous solution aerosol using a nebulizer, a metered dose inhaler, or other suitable delivery device. In the case of a nebulizer, the aqueous solution held within a fluid reservoir is converted into an aqueous spray, only a small portion of which leaves the nebulizer for delivery to the subject at any given time. The remaining spray drains back into a fluid reservoir within the nebulizer, where it is aerosolized again into an aqueous spray. This process is repeated until the fluid reservoir is completely dispensed or until administration of the aerosolized spray is terminated. Such nebulizers are commercially available and include, for example, the Ultravent nebulizer (Mallinckrodt Inc., St. Louis, Mo.) and the ACORN II™ nebulizer (Marquest Medical Products, Englewood, Colo.). See also the nebulizer described in WO 93/00951, and the device for delivering aerosolized aqueous formulations described in U.S. Pat. No. 5,544,646.

All patents, patent applications, internet citations, and technical articles cited herein are incorporated herein by reference in their respective entireties for all purposes.

The present invention will now be further described in the context of the following illustrative examples. Note that full cites to articles cited throughout the Examples appear in a list at the end of the Examples.

EXAMPLE 1

Experiments were conducted to express C17S IFN-beta-1b in *E. coli.*

Construction of C17S IFN-Beta Gene Sequence

The C17S protein sequence for IFN-beta (according to SEQ ID No. 2 and shown in FIG. 1) was expressed in *E. coli.*

The gene for Interferon-beta (IFN-β) was isolated by PCR amplification of human genomic DNA (Cat. # 636401, Clontech, Calif.), using primers BARO 1 (5'CACGTGCATATGAGCTACAACTTGCTTGGATTC) (SEQ ID No. 4) and BARO 4 (5'CGGAATTCTTAGTTTCGGAGGTAACCTGTAAG) (SEQ ID No. 5). The resulting fragment was digested with restriction enzymes NdeI (recognition sequence CATATG) and EcoRI (recognition sequence GAATTC), and cloned into similarly digested and calf intestine alkaline phosphatase (CIP)-treated pUC19. Several clones were isolated and sequenced, and one clone with the correct sequence was subjected to PCR-based mutagenesis using forward primer BARO 8 (5'AGCAGCAATTTTCAGTCTCAGAAGCTTCTGTGGCAATTG) (SEQ ID No. 6) and reverse primer BARO 9 (5'CAATTGCCACAGAAGCTTCTGAGACTGAAAATTGCTGCT) (SEQ ID No. 7) as described in Higuchi R. (PCR Protocols; M.A. Innis et al., eds.1990, Academic Press), which changed the codon TGT for Cysteine at position 17 (C17) to Serine (TCT, C17S). After mutagenesis, the gene was cloned into pUC 19, and sequenced to confirm the presence of the C17S mutation. The final sequence of the IFN-β C17S gene is according to SEQ ID No. 3 as shown in FIG. 2. In this Figure, IFN-β C17S is encoded by DNA sequence shown in uppercase. The codon TCT for Ser-17 is underlined, as are recognition sites for NdeI (CATATG), HindIII (AAGCTT), and EcoRI (GAATTC).

Construction of the Preliminary Expression Plasmid and Expression in recA+Strains The IFN-β C17S gene was isolated as an NdeI-EcoRI fragment and cloned into similarly digested and CIP-treated pET21a+ (Novagen, WI). The vector pET21a+ carries the phage T7 promoter and lac operator for regulated expression, and confers ampicillin resistance. The resulting plasmid was transformed into BL21 (DE3) and Rosetta2 (DE3), two strains that express the T7 RNA polymerase under the control to the lac promoter. The two strains were the same except for that Rosetta2 (DE3) contains the plasmid pRARE2 which expresses tRNAs for the rare *E. coli* codons AUA (Ile), AGG, AGA, CGG (Arg), CUA (Leu), CCC (Pro), and GGA (Gly), and confers chloramphenicol (Cam) resistance. Strain A [IFN-β C17S/pET21a+/BL21 (DE3)] and Strain B [IFN-β C17S/pET21a+/Rosetta (DE3)] were grown at 37° C. in LB medium containing the appropriate antibiotics (Strain A, ampicillin; Strain B, ampicillin+chloramphenicol) to an optical density at 600 nm (OD-600) of 0.5. Expression of IFN-β C17S was induced by addition of 0.75 mM IPTG. Samples were taken for analysis by SDS-PAGE shortly before induction, and one, two, three and four hours after induction. We found that Strain A expressed no observable IFN-β C17S whereas Strain B expressed ~20% of total cell protein at two and three hours after induction.

Construction of the Final Expression Plasmid

The IFN-β C17S gene was then transferred to pET24a+, a T7 promoter vector that carries the kanamycin resistance gene. FIG. 3 shows the construction of this plasmid, termed pBAR12, starting with human genomic DNA. pBar12 was used to transform BL21 (DE3) and Rosetta2 (DE3), and the resulting strains, Strain C and Bar23, were subjected to growth (with LB medium containing the appropriate antibiotics), IPTG induction and expression analysis as described above. We found that Strain C expressed no detectable IFN-β C17S whereas Bar23 expressed between 10% and 15% of total cell protein. We assume that both Strain B (above) and Bar23 express IFN-β C17S because these strains contain pRARE2, which carries tRNA genes for rare *E. coli* codons. Such codons are present in the IFN-β C17S gene.

Development of the Final Expression Strain

Strains BLR (DE3) and HMS174 (DE3) (Novagen) were transformed with pRARE2 to produce strains D and E. These strains, in addition to containing the pRARE2 plasmid, are recA−. Strains D and E were transformed with pBAR12 to give Bar24 and Bar25, respectively, which were evaluated for IFN-β C17S expression as described above, except that the 4 hour time point after induction was eliminated. These strains produced substantial levels of IFN-β C17S, with the HMS174-based strain (a K12 strain) expressing approximately twice as much of the protein as the BLR-based (B) strain. This result and the data from additional experiments comparing the two strains using other media (not shown) led us to choose Bar 25 as the final IFN-β strain, which is designated as the Bar 25 protein herein. We then confirmed the sequence of the IFN-β C17S gene in Bar25 using the T7 primer (5'TAATACGACTCACTATAGGG) (SEQ ID No. 8) and the T7 terminator primer (5'GCTAGTTATTGCTCAGCGG) (SEQ ID No. 9).

Media Development

Table 2 shows results of experiments comparing a variety of media, which were conducted to look for improved growth characteristics and IFN-β C17S expression in shake flasks, relative to LB medium. Based on these data, our optimal medium for expression is 4% yeast extract, 0.1M MES, pH 6.5, 1% NaCl. Additionally, the presence of glycerol into the fermentation improved cell density.

Although the expression method provided in this example differs from what has been published previously (U.S. Pat. No. 4,450,103), the expression system has been shown to provide the proper amino acid sequence according to SEQ ID No. 2 and FIG. 1.

coli suspension was centrifuged in a JA-14 rotor, 8000 rpm for 10 min. The supernatant is decanted. The resulting pellet of insoluble material was suspended in 200 mL of distilled water and recentrifuged. The pellet was frozen at −20° C. or subjected to organic extraction as described below.

TABLE 2

| No. | YE | Tryptone | Buffer pH | NaCl | Glycerol | O.D. Ind | O.D. Harvest | Young Units g/OD.L |
|---|---|---|---|---|---|---|---|---|
| 1 | 3% D | 1% T | 0.1M MES 6.5 | 1% | 0 | 1.5 | 2.75 | 0.10 |
| 2 | 4% D | 0 | 0.1M MES 6.5 | 1% | 0 | 1.52 | 2.97 | 0.10 |
| 3 | 2.4% D | 1.2% T | 0.09M PO$_4$ 7.5 | 0 | 0.50% | 5.23 | 7.29 | 0.05 |
| 4 | 2% D | 3.5% T | 0.09M PO$_4$ 7.5 | 0.50% | 0 | 3.77 | 5.5 | 0.05 |
| 5 | 4% D | 0 | 0.1 M MES 6.5 | 1% | 0 | 1.83 | 2.29 | 0.10 |
| 6 | 4% D | 0 | 0.1 M MES 6.5 | 1% | 1% | 2.85 | 4.45 | 0.05 |
| 7 | 4% D | 0 | 0.1 M MES 6.5 | 1% | 0 | 2.97 | 3.72 | 0.03 |
| 8 | 4% D | 0 | 0.09M PO$_4$ 7.5 | 1% | 0 | 2.48 | 3.39 | 0.05 |
| 9 | 4% D | 0 | 0.1M MES 6.5 | 1% | 0 | 1.58 | 3.22 | 0.10 |
| 10 | 4% D | 0 | 0.1M MES 6.5 | 1% | 1% | 3.33 | 5.78 | 0.08 |
| 11 | 4% D | 0 | 0.1M MES 6.5 | 1% | 0 | 3.03 | 4.76 | 0.10 |
| 12 | 4% M | 0 | 0.1M MES 6.5 | 1% | 0 | 2.59 | 4.32 | 0.08 |
| 13 | 4% M | 1% T | 0.1M MES 6.5 | 1% | 0 | 2.72 | 4.4 | 0.10 |
| 14 | 4% M | 1% S | 0.1M MES 6.5 | 1% | 0 | 2.92 | 4.7 | 0.08 |
| 15 | 4% M | 0 | 0.1M MES 6.5 | 1% | 0 | 3.01 | 4.65 | 0.08 |

Cells were grown at 37° C. and induced with 0.75 mM IPTG. Media are as shown except No. 7 contains 0.3 mM ZnCl$_2$ at the time of induction.
YE = yeast extract;
D = Difco YE;
M = Marcor YE;
T = Tryptone;
S = Soytone.

EXAMPLE 2

The effect of "traditional" refolding conditions on the refolding of IFN-beta from inclusion bodies were examined.

Washed inclusion bodies of IFN-beta were obtained as described below. U.S. Pat. Nos. 7,064,192 and 6,489,450 teach the skilled artisan the general methods for refolding protein aggregates using high pressure (Randolph, Carpenter et al. 1999). Of these methods, 2000 bar treatment at a temperature of 25° C., for sixteen hours, at a refolding pH of 8.0, in the presence of 4 mM reduced glutathione (GSH) and 2 mM oxidized glutathione (GSSG) has been used for the refolding of proteins that contain disulfide bonds such as hen egg white lysozyme, placental bikunin, and malaria pfs48 (St. John, Carpenter et al. 2002; Seefeldt, Ouyang et al. 2004; Seefeldt 2005; Lee, Carpenter et al. 2006). In line with those earlier experiments, inclusion bodies of IFN-beta were pressure treated at 2000 bar for sixteen hours at 25° C. in aqueous solutions conditions containing 50 mM Tris, pH 8.0, 4 mM GSH, 2 mM GSSG. After depressurization, the samples were tested for refolding by RP-HPLC and found to have a refolding yield of 0% as analyzed by RP-HPLC. The addition of arginine, a commonly used refolding agent that has been taught extensively in the prior art, also did not improve refolding yields (data not shown). (Arakawa and Tsumoto 2003; Tsumoto, Umetsu et al. 2004; Seefeldt 2005).

Generation of Washed Inclusion Bodies

An E. coli whole cell pellet (~5 g) was thawed and suspended in 100 mL BPER Reagent (Pierce Chemical). The suspension was stirred for 20 minutes at room temperature. One mL of lysozyme stock solution (10 mg/2 mL H2O, made fresh) was added. The mixture was stirred an additional 10 min at room temperature. 150 µl of DNAse solution (2 mg/mL, frozen stock) was added to decrease the viscosity of the mixture. After an additional 1 hour of stirring, the lysed E.

High Pressure Refolding Experiments

High pressure refolding experiments were conducted by creating stock solutions of IFN-beta inclusion bodies, IFN-beta methanol precipitate (see Example 4), 500 mM CAPS buffer (pH 10), 5% Zwittergent 3-14 surfactant, and 100 mM redox components. The stock solutions were used to create 500 uL of refolding solution, mixed in Eppendorf tubes. The mixed samples were than placed in sealed syringes and pressure treated as described previously (Seefeldt, Ouyang et al. 2004). Care was taken to ensure that insoluble protein aggregate was pipetted correctly without filtering or loss in the Eppendorf tubes. The concentration of protein present in the inclusion body precipitate was obtained by a reduced RP-HPLC method. The protein concentration of methanol precipitate of the butanol extraction was obtained by taking an absorbance reading at 280 nm prior to methanol precipitation and calculating the protein concentration using an extinction coefficient of 1.5 Abs/(mg/ml protein).

Reverse-Phase High Performance Liquid Chromatography (RP-HPLC)

The conditions for analyzing refolds were as follows: HPLC: Agilent HP 1100, Column: C3 Zorbax with guard column 300SB3.5 um 4.6×150 mm Solvents: A: Water, 0.1% TFA B: Acetonitrile, 0.1% TFA Flow Rate: 1 ml/min Temp: 30° C. Injection: 20 µl Absorbance: 215 nm, 280 nm

| Gradient: | Time (min) | % B |
|---|---|---|
| | | 27 |
| | | 45 |
| | | 56 |
| | | 100 |
| | | 27 |

Sodium Dodecyl Sulfate-Polyacrylamide Gel Electrophoresis (SDS-PAGE)

Reducing and non-reducing SDS-PAGE was used to examine the purity and disulfide content of pressure solubilized IFN-beta. Approximately 5 ug of protein from the processed supernatent was added to the appropriate volume of 2×SDS-PAGE sample buffer (Invitrogen, Carlsbad, Calif.). The SDS-protein mixture was heated for five minutes at 100° C. 4-20% Novex Tris-glycine precast gels were used (Invitrogen, Carlsbad, Calif.), with 400 ml of diluted 10× Tris-glycine running buffer (BioRad, Hercules, Calif.). Gels were run for fifty minutes, and staining was conducted with methanol/acetic acid-free Coomassie blue for total protein analysis (BioRad, Hercules, Calif.).

EXAMPLE 3

This example provided improved refolding of IFN-beta from inclusion bodies.

A series of experiments were conducted to examine the effect of pH, redox chemistry, refolding pressure, and detergent effects on the refolding if IFN-beta. After screening studies were conducted, the preferred refolding conditions were found to be incubation at 3500 bar, 50 mM CAPS (pH 10), 1.3 mM cysteine, 0.3 mM cystine, 0.05% Zwittergent 3-14 surfactant for 16 hours at 25° C. Depressurization was conducted at a rate of 250 bar/five minutes. Refolding yields of 44%+/−2% were obtained, as based on RP-HPLC (see the methods described in Example 2).

Refolding in "preferred conditions" was compared to "typical" conditions that are taught in the prior art (2000 bar, pH 8, 4 mM GSH and 2 mM GSSG, 16 hours, 25° C., 250 bar/5 minute depressurization) and were found to significantly improve the refolding of IFN-beta in comparison to prior methods, with yields of 44%+/2% and 0% respectively as analyzed by RP-HPLC. This example demonstrates novelty and non-obviousness, as these refolding conditions would not be initially predicted based on either protein characteristics and/or previous refolding strategies.

EXAMPLE 4

The effect of solubilization and precipitation methods on the high pressure refolding yield was determined.

Figure 4:
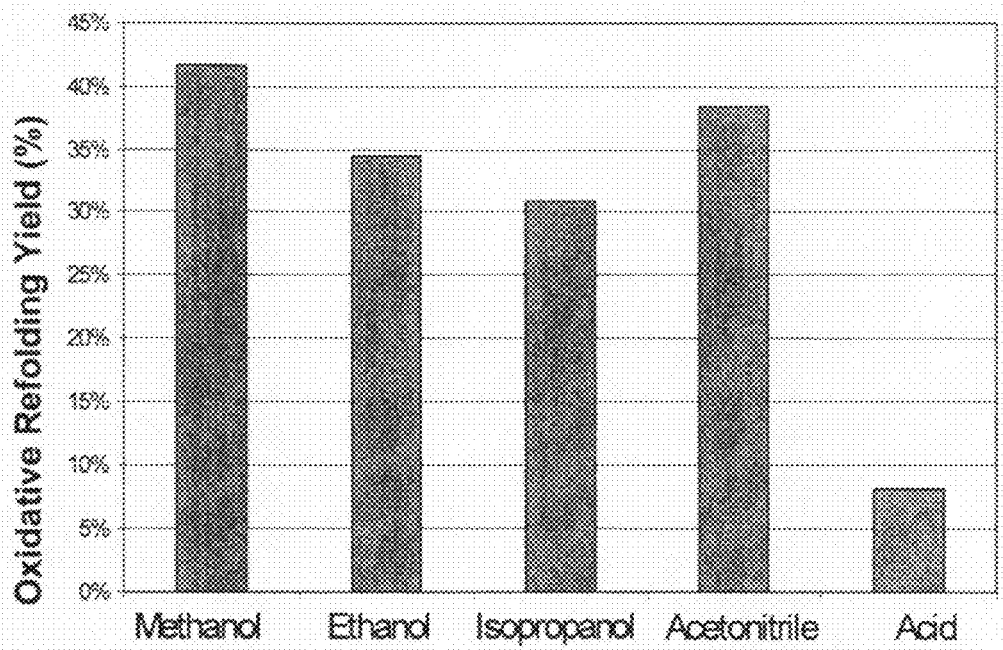
FIG. 4 is a chart showing the oxidative refolding yield as a function of the butanol precipitation method used.

Refolding of Butanol-Extracted IFN-Beta from Inclusion Bodies Using High Hydrostatic Pressure as a Function of Precipitation Method Precipitation of the butanol-extracted material by the methods discussed below was carried out by the addition of 66% v/v percent of methanol, ethanol, isopropanol or acetonitrile, respectively. For acid precipitation, IFN beta was precipitated out of the butanol by dilution (1:1 v/v) with phosphate buffered saline (PBS) containing 0.1% SDS followed by the adjustment of the pH to 5.5 using acetic acid. The precipitated material was washed and incubated under solution conditions identified to be effective for refolding of IFN-beta from inclusion bodies, specifically 50 mM CAPS, pH 10, 0.05% Zwittergent 3-14, 1.3 mM cysteine, 0.3 mM cystine, 0.5 mg/ml protein at a pressure of 3500 bar for 16 hours at 25° C. (hereinafter the "control" conditions). The refolding yield as a function of precipitation method is shown in FIG. 4.

Inclusion Body Extraction into Butanol

The pellet from 2-3 g inclusion bodies was suspended in 100 mL solubilization buffer (2% SDS, 20 mM Tris, pH 8.0, 2 mM EDTA, 10 mM DTT). The mixture was stirred for 30 min at room temperature. Next 200 mL of sec-butanol was added followed by 10 minutes of mixing to allow extraction of IFN beta into the organic-rich phase. The cloudy solution was centrifuged in a Beckman JA-10 at 6000 rpm for 10 min. The top organic layer is carefully removed from the small aqueous layer. A precipitate usually was present at the interface of the two liquids and at the bottom of the bottle. Next, approximately 550 mL of methanol (2×the volume of the organic layer) is added to the decanted organic-rich phase. The liquids ware thoroughly mixed and allowed to sit at 4° C. for 2-3 hrs. A white fluffy precipitate formed. This precipitate (insoluble IFN material, likely IFN-beta and/or an IFN-beta-SDS complex) was separated from the mixture by centrifugation using a Beckman JA-10, 6000 rpm, 10 minutes. The protein precipitate was stored as a suspension in a minimal amount of WFI (endotoxin free) water as it has a tendency to desiccate when frozen as a pellet for extended periods of time. The pellet was resuspended in a sufficient amount of water such that the final mixture was approximately 2-3 mg IFN-beta/mL. The methanol precipitate suspension was stored at −20° C.

The final concentration of IFN beta was determined by dissolving a small aliquot of the suspension in 6 M guanidine and measuring the absorbance at 280 nM.

High Pressure Refolding Experiments

High pressure experiments were conducted as described in Example 2. RP-HPLC was conducted in an identical manner to quantify refolding yields.

The experiment demonstrated that the precipitation method altered the high pressure refolding efficiency of the IFN-beta butanol precipitate. Less hydrophobic perturbants of the butanol phase (e.g. MeOH and acetonitrile) resulted in the formation of precipitated IFN-beta that was more amenable to high pressure refolding. Surprisingly, it was determined that the methanol- and acetonitrile-precipitated IFN-beta refolded better than acid-induced precipitation. Throughout the present specification, IFN-beta extracted in butanol and precipitated by the addition of methanol is termed "butanol precipitate" or "methanol-precipitate."

While not being bound by theory, it is believed that the difference in refolding between the two methods is the result of differences in aggregate structure. Conducting the butanol extraction step has the added advantage of removing protein impurities, further improving the refold step.

EXAMPLE 5

This experiments describes the determination of the "preferred" conditions for the refolding of IFN-beta from methanol-precipitated IFN-beta.

The Effect of Detergents on the Refolding of IFN-Beta from Methanol Precipitate

Figure 6:
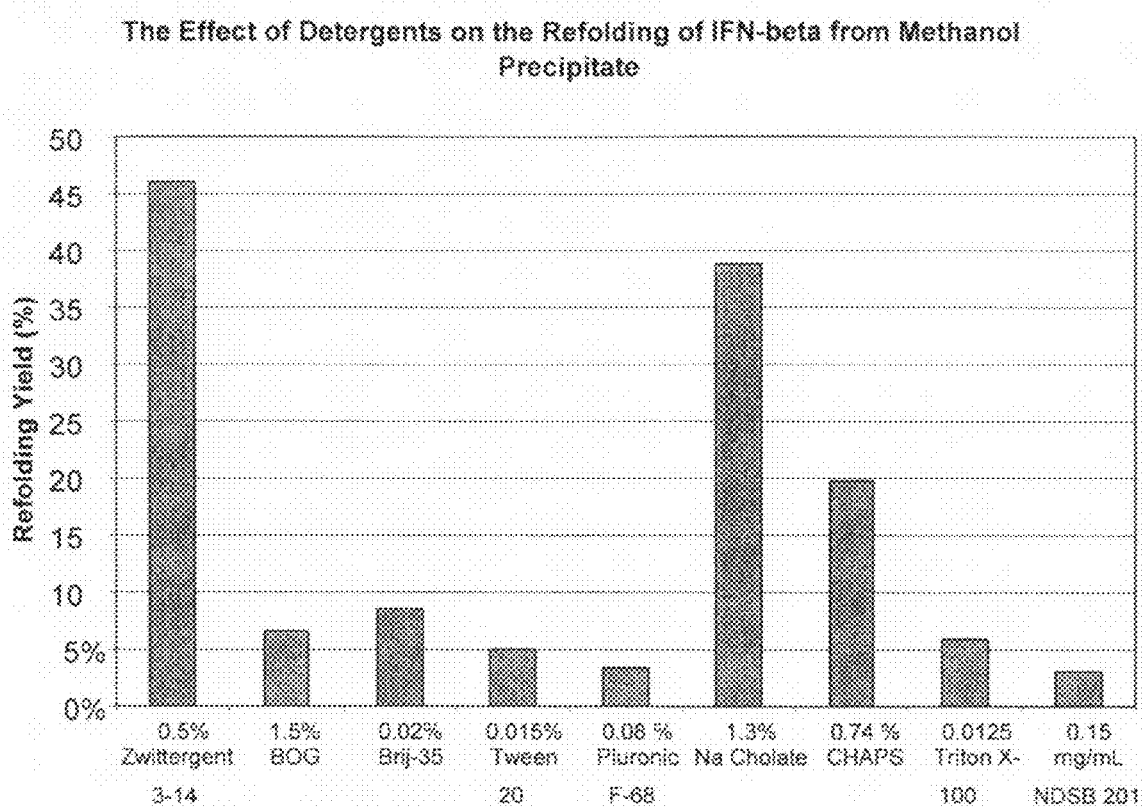
FIG. 6 is a chart showing the refolding yield as a function of detergent used.

Detergents were screened for the refolding of IFN-beta from methanol-precipitate in buffer containing 50 mM CAPS (pH 10), 1.3 mM cysteine, 0.3 mM cystine. Pressures of 3500 bar were used at 25 C with a depressurization rate of 250 bar/five minutes. A comparison of yields of various detergents is shown in FIG. 6. The Zwittergent SB 3-14 surfactant was the most effective detergent for the refolding of IFN-beta and matched results obtained during the refolding of IFN-beta from inclusion bodies. Substantial refolding yields were observed using sodium cholate (38%), however the yield was still lower relative to the control using the Zwittergent SB 3-14 surfactant. The use of all other surfactants in the refolding buffer resulted in low yields (<20%).

The Effect of pH on the Refolding of IFN-Beta from Methanol Precipitate

Figure 7:
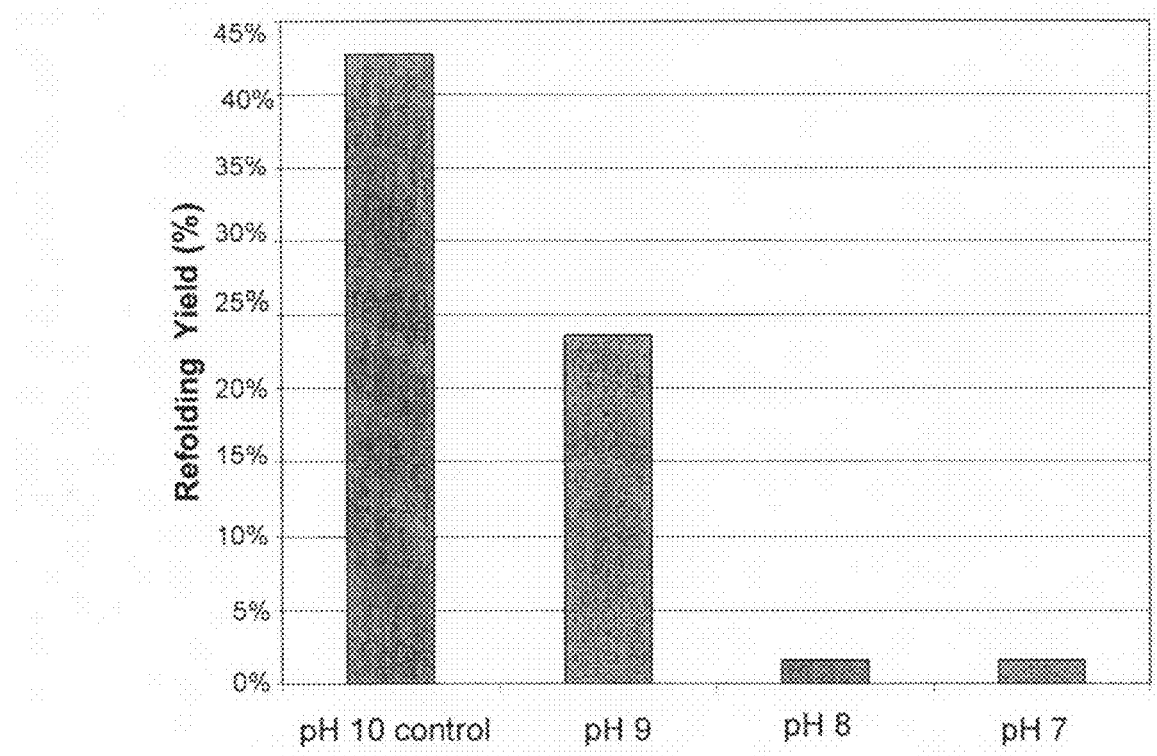
FIG. 7 is a chart showing the refolding yield as a function of pH.

The effect of pH on the high pressure refolding yield of IFN-beta extracted from butanol and precipitated by addition of methanol was measured during incubation at 3500 bar with 1.3 mM cysteine, 0.3 mM cystine, 0.05% Zwittergent 3-14 surfactant, 50 mM buffer at 25° C. for 16 hours. The refolding yield as function of pH is shown in FIG. 7. pH 10 Proved to be an effective pH for the refolding of IFN-beta relative to lower pH's, and is counterintuitive to previous results that show that pH 8.0 provided optimum refolding yields for proteins that contained disulfide bonds (St. John, Carpenter et al. 2002; Seefeldt, Ouyang et al. 2004). A similar result was observed for the refolding of IFN-beta from inclusion bodies.

Figure 8:
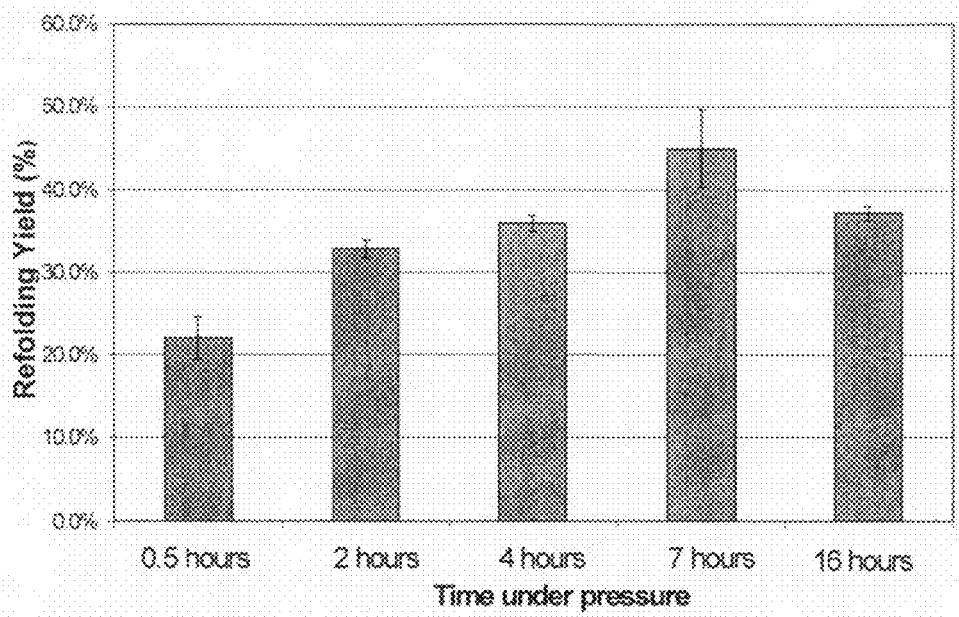
FIG. 8 is a chart showing the refolding yield as a function of time under pressure.

The Kinetics of the Refolding of IFN-Beta from Methanol Precipitate Under "Control" Conditions The effect of refolding time on the high pressure refolding yield of IFN-beta extracted from butanol and precipitated through methanol precipitation was measured following incubation at 3500 bar with 1.3 mM cysteine, 0.3 mM cystine, 0.05% Zwittergent 3-14 surfactant, 50 mM buffer at 25° C. for various periods of time. The refolding yields are shown in FIG. 8.

Refolding yield reached its maximum at seven hours under these conditions. Shorter times decreased yields, likely due to the kinetics of aggregate dissociation. Longer times did not improve the refolding yield.

Figure 9:
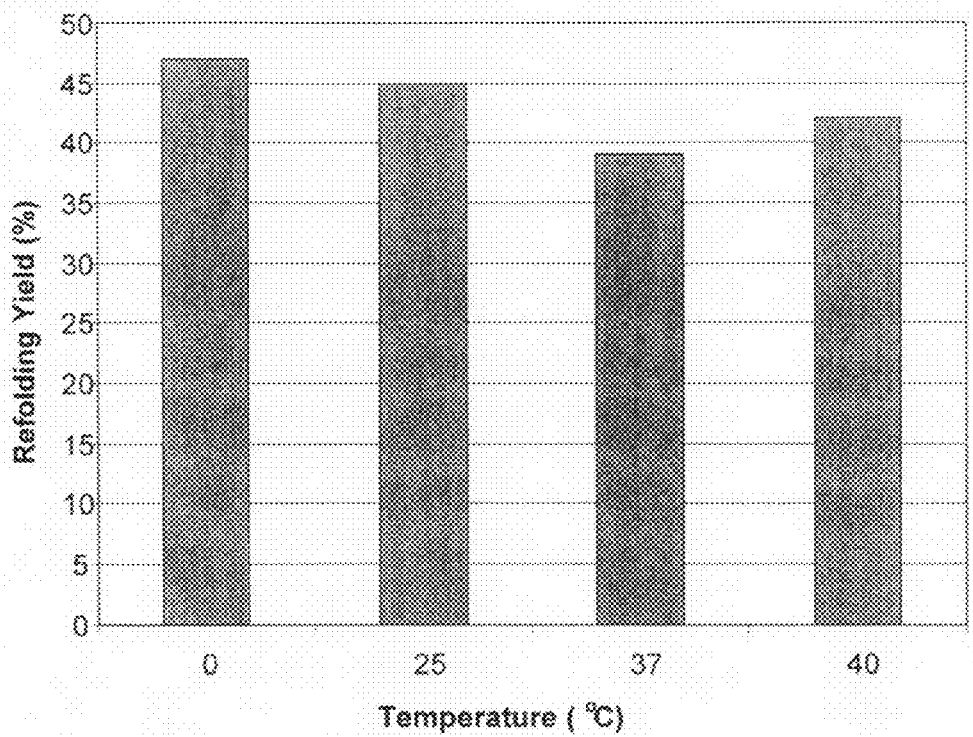
FIG. 9 is a chart showing the refolding yield as a function of temperature.

The Effect of Temperature on the Refolding of IFN-Beta from Methanol-Precipitate Under "Control" Conditions The effect of temperature on the refolding of IFN-beta from methanol precipitate under "control" conditions was examined. Lower refolding temperatures were found to result in a slight increase in refolding yield. However the effect was small, as shown in FIG. 9.

Figure 10:
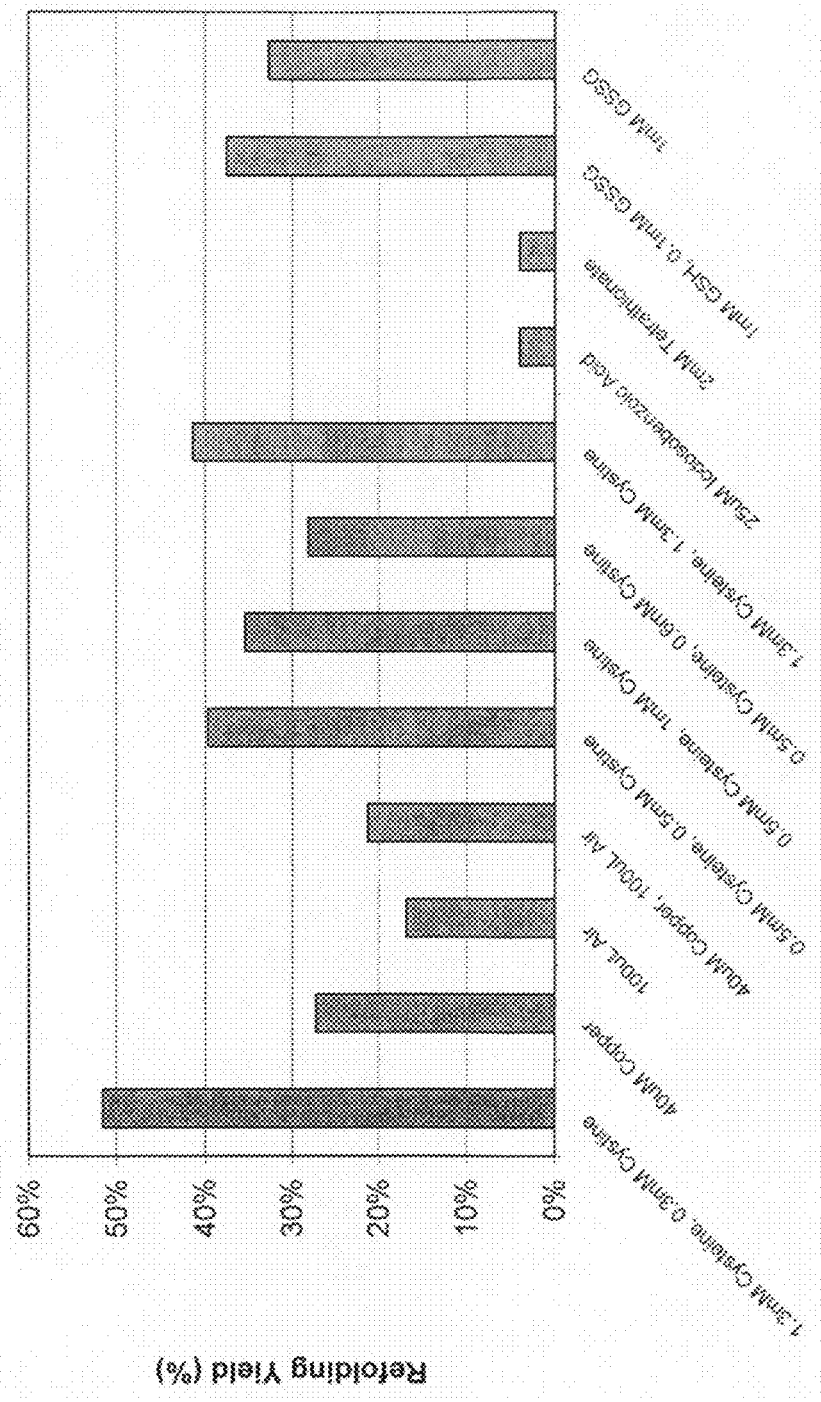
FIG. 10 is a chart showing the refolding yield as a function of redox chemistry used.

The Effect of Disulfide Chemistries on the Refolding of IFN-Beta from Methanol Precipitate Under "Control" Conditions The effect of disulfide chemistries on the refolding of IFN-beta from methanol precipitate when all other variables (pressure, pH etc.) were maintained under "control" conditions was examined, and the results are shown in FIG. 10. 1.3 mM cysteine, 0.3 mM cystine was found to be the best disulfide shuffling reagent. Altering the total cysteine/cystine thiol concentration or the ratio cysteine to cystine did not increase refolding yields. Oxidizing agents such as air, air catalyzed with trace amounts of copper, air oxidation after thiolate reduction, and the addition of iodosobenzoic acid failed to improve the refolding yield in comparison to the cystine/cysteine redox pair.

Figure 11:
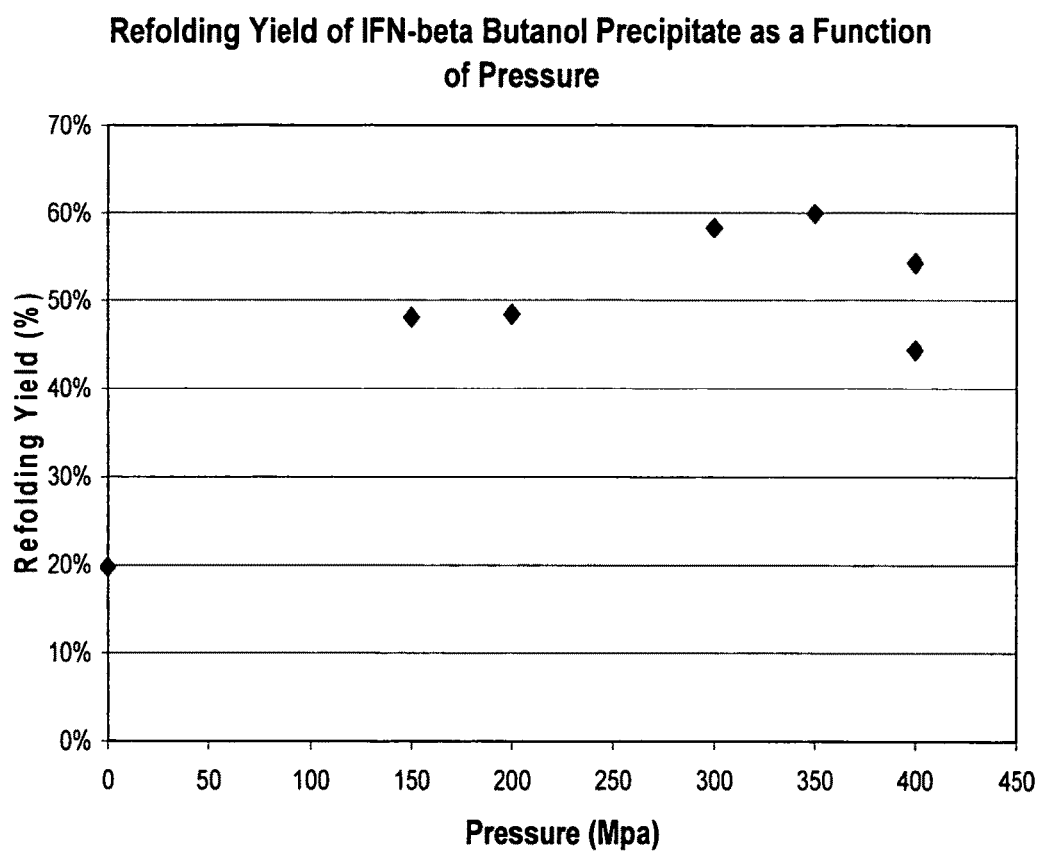
FIG. 11 is a chart showing the refolding yield as a function of pressure.

The Effect of High Pressure on the Refolding of IFN-Beta from Methanol Precipitate The effect of high pressure treatment (0-4000 bar) was tested on the refolding of methanol precipitated IFN-beta in solutions containing 0.5 mg/ml IFN-beta, in the "control" refolding condition. Results are shown in FIG. 11. High pressure treatment (3500 bar) resulted in significant improvement in the amount of oxidized and soluble IFN-beta over atmospheric samples, resulting in refolding yields of 60% vs. 20% respectively. A refolding pressure of 3500 bar proved to be the optimum refolding pressure. The result was also observed for the refolding of IFN-beta from inclusion bodies.

Refolding methods were conducted as described in earlier examples. RP-HPLC analysis was used to quantify refolding yields (See Example 2).

It is impossible to predict the best-case conditions for the refolding of a specific column, consequently all conditions (e.g. pH, temperature, disulfide chemistries etc.) must be screened for each individual protein.

Zwittergent SB 3-14 surfactant and Na cholate were found to be preferred for the refolding of IFN-beta, at high yields, a result that was unknown prior to the experiments. Low temperature (0 C), high pH (10) and longer refolding times (up to 16 hours) were all found to improve yields. The results of the experiments demonstrate that high pressure can refold methanol precipitated aggregates of IFN-beta and that refolding yields were higher at 3500 bar relative to those obtained at the more typical pressures near 2000 bar that have been used to refold proteins in previous work. Cysteine/cystine was found to be a preferred redox reagent. This is a significant result considering the prior art that discusses the use of air oxidation and iodosobenzoic acid for the refolding of IFN-beta (Shaked, Stewart et al. 1993). This result appears to be a function of the starting material since the use of iodosobenzoic acid improved the refolding yield after high pressure treatment of inclusion bodies. Reduced (GSH) and oxidized (GSSG) glutathione disulfide shuffling agents unexpectedly failed to improve the refolding and disulfide bond formation of IFN-beta refolded from methanol precipitate. The reasons for this are unknown and thus non-obvious.

EXAMPLE 6

Conditions were developed to minimize the possibility of deamidation, which is a well characterized chemical modification of proteins that is accelerated by extreme pH (both high and low), elevated temperature, and structural fluctuations, pressure, and protein age.

Refolding of IFN-beta with yields greater than 26% were obtained by refolding methanol precipitate at pressures of 3200 bar, for 2 hr at 25° C., using a pressurization rate of 100 bar/min and linear depressurization of 3200 bar/10 min. Solution conditions were 50M CHES (pH 9.0), 0.05% Zwittergent 3-14 surfactant, 1.3 mM cysteine, 0.3 mM cystine.

Refolding methods are described in previous examples. The above identified experimental conditions related to pH, temperature, and pressure were selected in accordance with the described principles to minimize deamidation of the IFN-beta sample material.

By altering conditions well-known to accelerate chemical modifications such as deamidation, the extent of deamidation that occurs during the refold can be controlled.

EXAMPLE 7

Methods for the purification of IFN-beta to generate material containing low-levels of aggregate were determined.

Figure 12:
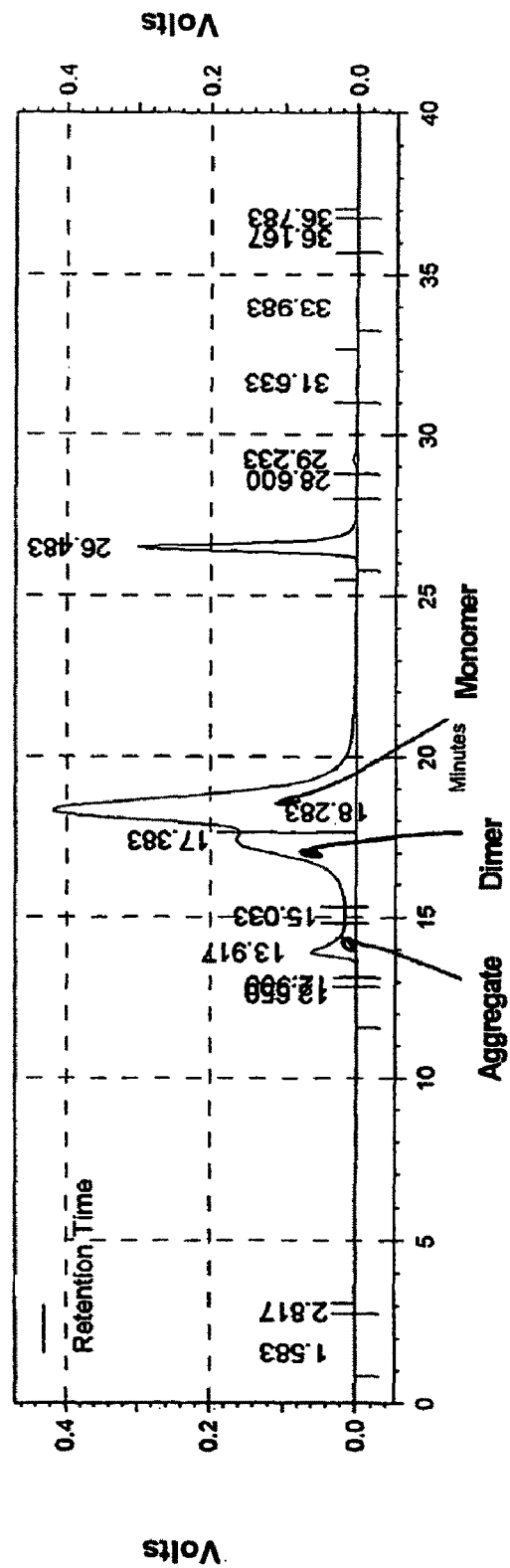
FIG. 12 is a chromatogram showing aggregate content of a sample measured by SE-HPLC.

After refolding using methods described for methanol-precipitate described in Example 4, the aggregate content was measured by using SE-HPLC, the chromatogram being shown in FIG. 12. Aggregate exists in the material after high pressure refolding. Aggregate exists as exhibited by material eluting at X (~10').

Figure 13:
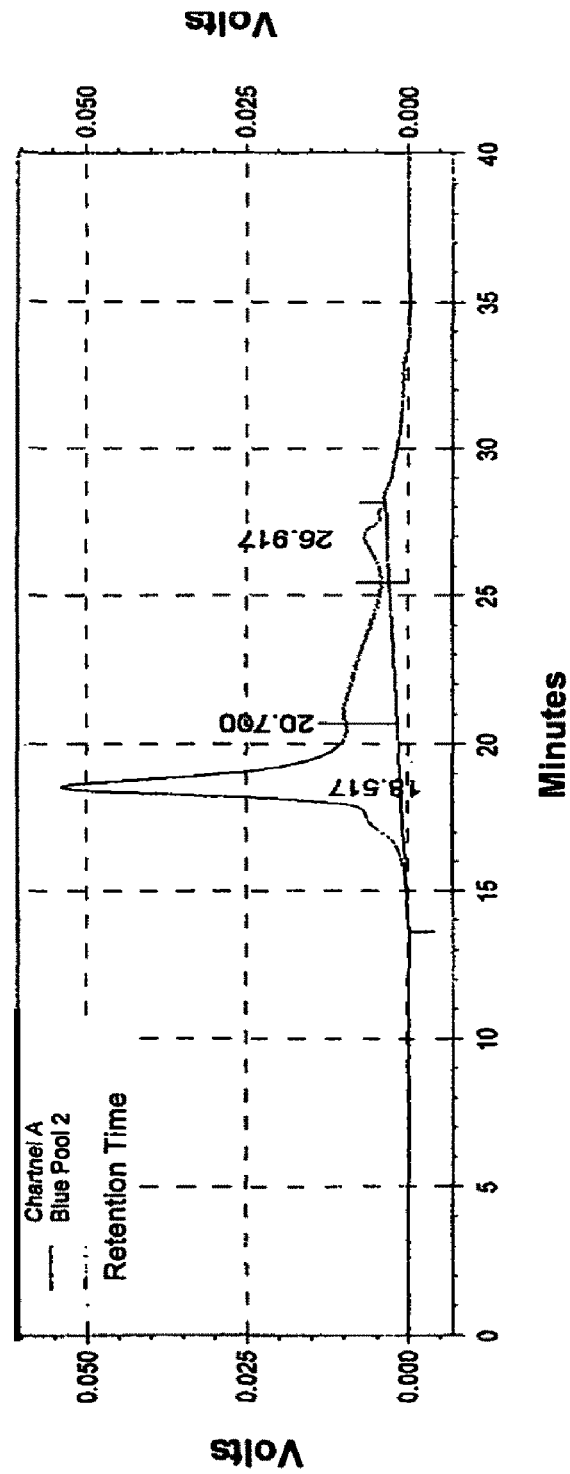
FIG. 13 is a chromatogram showing aggregate content of a sample measured by SE-HPLC.

The refolded material was purified using three column steps, followed by tangential flow filtration, described in order as a Blue-Sepharose column, Cu-IMAC column, and a S-Sepharose column (in the order described). The 1$^{st}$ column step used a Blue-Sepharose column, resulting in material that had decreased levels of aggregate as demonstrated by SE-HPLC chromatography as shown in FIG. 13.

Figure 14:
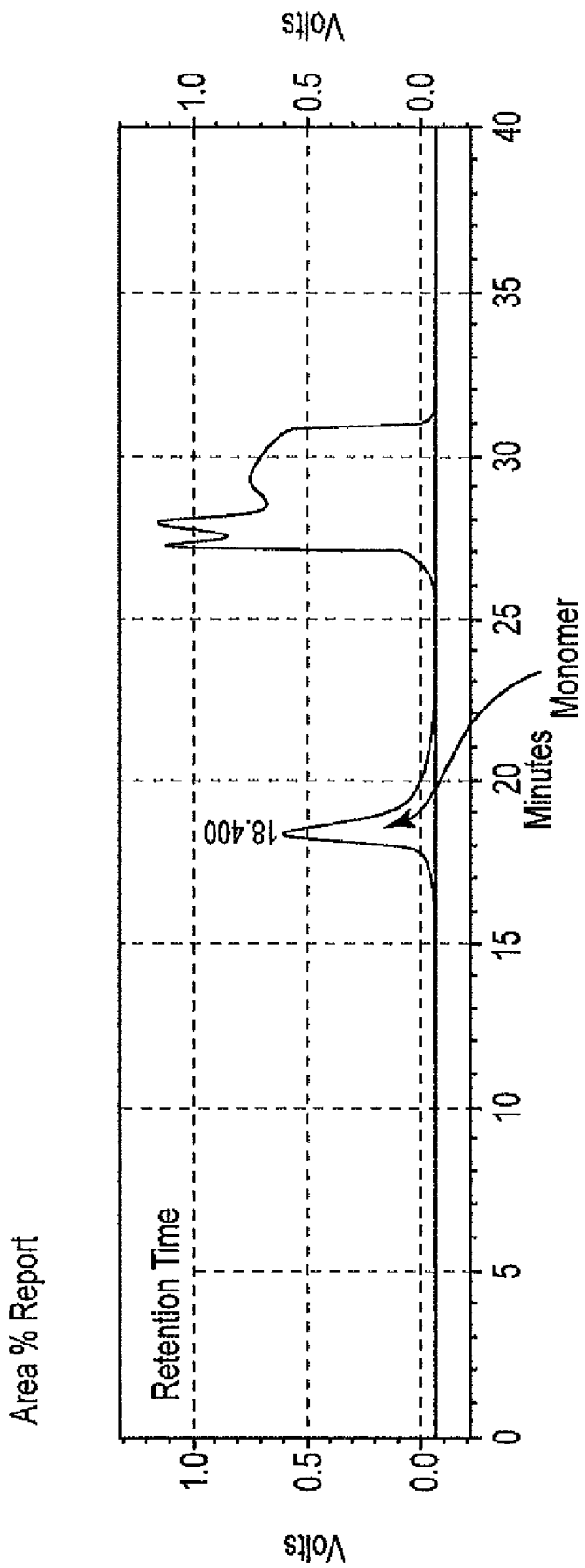
FIG. 14 is a chromatogram showing aggregate content of a sample measured by SE-HPLC.

The material pooled after the Blue-Sepharose column step was loaded onto a Cu-IMAC column and further purified. The resulting aggregate level was measure by SE-HPLC analysis, and the sample was shown to be essentially aggregate-free as may be seen in FIG. 14.

Figure 15:
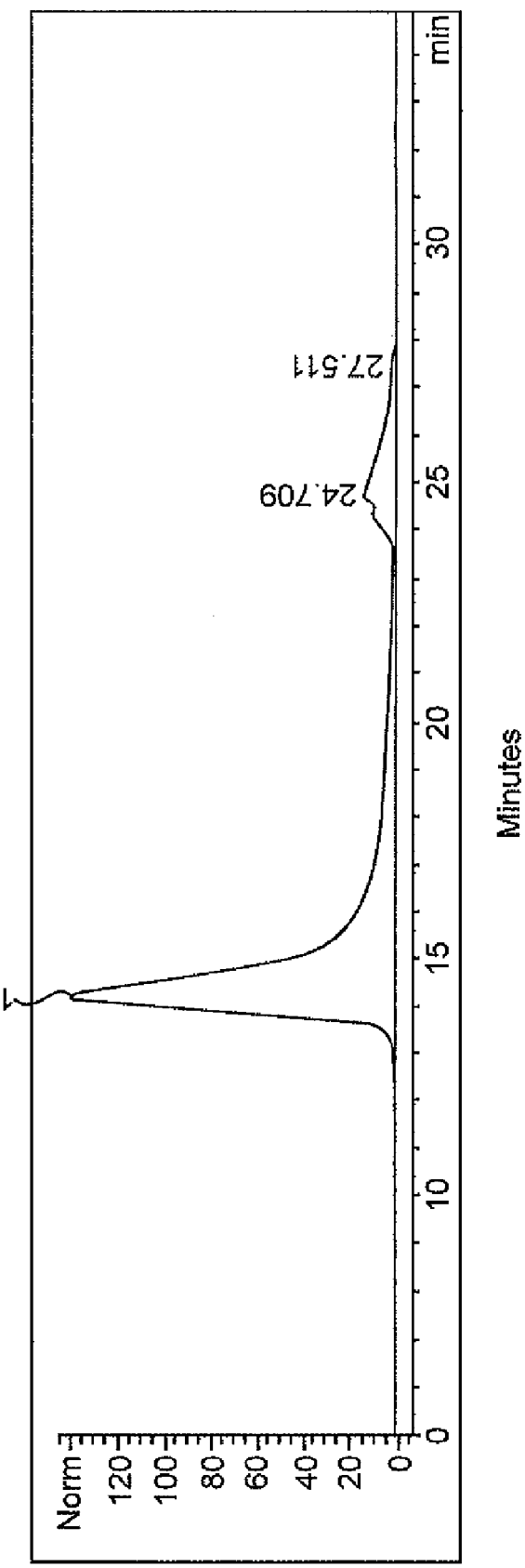
FIG. 15 is a chromatogram showing aggregate content of a sample measured by SE-HPLC.

After this step, the protein was loaded onto a S-Sepharose column to enable further purification and remove the Zwittergent 3-14 from the solution. The SE-HPLC chromatogram after this column step is shown in FIG. 15.

Blue-Sepharose Purification

Materials: Toyopearl AF-Blue HC-650M blue affinity resin was used for purification of IFN-beta. For this column, "Equilibration buffer" containing 50 mM NaPO4 pH 7.2 and 1 M NaCl was used, with an "Elution buffer" containing 20 mM NaPO4 pH 7.2, 1 M NaCl, 50% ethylene or propylene glycol.

Methods: The column was equilibrated by washing (at room temperature) a 50 mL Toyo blue column (Part # 19689) with 3 column volumes (CV) of distilled water, followed by 3 CVs of elution buffer, and 3 CVs of equilibration buffer. The volume of the column is a function of the scale of the process. The column was loaded by diluting the clarified refold 5× in equilibration buffer and load onto the column at a flowrate of 5 ml/min. The column was washed after loading with 3 CV of equilibration buffer. 3-5 mg IFN-beta were loaded per mL resin. For column elution, the column was washed with 1 CV of elution buffer at rate of 5 ml/min, followed by 3 CVs of 25% elution buffer (with the remainder equilibration buffer), followed by 6 CVs of 100% elution buffer. Fractions containing purified IFN beta were pooled and stored at 4 C.

Cu-IMAC Purification

Materials: A copper IMAC column (GE Hi-Trap column PN# 17-0921-08) was used to remove endotoxin, and *E. coli* contaminant proteins. An "Equilibration Buffer" containing 20 mM NaPO4 pH 7.2, 0.2 M NaCl, 10% Ethylene Glycol, and 0.05% Zwittergent SB 3-14 surfactant. An "Elution buffer" containing the equilibration buffer with the addition of 50 mM imidizole was also used. Two columns (5 ml and 1 ml) were used in series to minimize copper contamination.

Methods: A 5 mL IMAC column was charged with 2 CVs of a solution containing 10 mM CuSO4. The column was then extensively washed with water until no copper ions were detected visually. The column was then equilibrated with 3 CVs of equilibration buffer. The 1 mL IMAC column was then added to the end of the 5 mL column and washed with an additional 2 CVs of equilibration buffer. For column loading, the blue pool (column #1) was diluted 5× in equilibration buffer and loaded onto the columns at a flowrate of 1 ml/min. The column was washed after loading with 2 CVs of equilibration buffer and 2-3 mg IFN beta was loaded per mL of resin. For column elution, at a flow rate of 1 mL/min, the column was washed with 1 CV of equilibration buffer, followed by 25 CV linear gradient from 0-60% Elution buffer, with the remainder being equilibration buffer, followed by 3 CVs of 100% elution buffer. Fractions containing purified IFN beta and no visible ECPs or aggregates (based on SDS-PAGE and sizing) were pooled and stored at −20° C.

S-Sepharose Purification

Materials: A 1 ml GE HiTrap SP FF (PN# 17505401) was used to further purify IFN-beta and remove Zwittergent 3-14 from the process. An "Equilibration Buffer A" containing 20 mM NaPO4 (pH 6.7), 50% propylene glycol, and 0.01 or 0.05% Tween-20 was used as well as "Equilibration Buffer B" which contains the same reagents at a pH of 8.0. An 'Elution buffer" containing 20 mM Tris (pH 8.0), 50% propylene glycol, 0.01% or 0.05% Tween 20, 2M NaCl, pH 8.0 was generated.

Methods: The column was then equilibrated with 3 CVs of equilibration buffer A. For column loading, the Cu pool (column #2) was diluted 10× into dilution buffer and loaded onto the columns at a flowrate of 1 ml/min. The column was washed after loading with 4 CVs of Equilibration buffer A, followed by 6 CVs of Equilibration buffer B. For column elution, at a flow rate of 1 mL/min, the column was washed with a step elution of Elution buffer.

Size-Exclusion Chromatography (SE-HPLC)

SEC-HPLC analysis of protein fractions was conducted on a Agilent 1100 equipped with a TSK G2000 SW$_{XL}$ size exclusion column (Tosohaas). The HPLC parameters were as follows: Solvent of 10 mM HCL in water, flow rate of 0.5 ml/min (isocratic), room temperature, an injection of 50 µl with absorbance measured at both 215 and 280 nm.

Three column steps can be used to extensively purify high pressure refolded IFN-beta to generate a pharmaceutical compound that was essentially aggregate free.

EXAMPLE 8

Studies were conducted to determine if IFN-beta refolded using the methods described in Example 6 could also be purified to be aggregate free.

SE-HPLC results after the $3^{rd}$ purification step (S-sepharose) demonstrated that an IFN-beta sample can be generated that is essentially aggregate free, as shown in FIG. 15.

Refolding was conducted per Example 6, with purification and analytical conducted per Example 7.

Refolding methods described in Example 6 can be used to make a pharmaceutical compound that is essentially aggregate free.

EXAMPLE 9

Studies were conducted to determine the stability of IFN-beta purified by the methods described in Examples 7 and 8. Purified IFN-beta was placed in various liquid formulations and tested for aggregate formation.

Samples purified using the $1^{st}$ two column steps described in Example 7 were dialfiltrated into five liquid formulations listed in Table 3.

TABLE 3

| Form Code | Buffer | pH | Tonicity Modifier | Surfactant (0.01%) | Concentration (mg/mL) | Lot # | Fill Volume |
|---|---|---|---|---|---|---|---|
| 0.25A4SP20 | 25 mM Sodium Acetate | 4.0 | 5% Sorbitol | PS20 | 0.25 | B039-40 | 1 mL |
| 0.25A4TP80 | 25 mM Sodium Acetate | 4.0 | 9% Trehalose | PS80 | 0.25 | B039-40 | 1 mL |
| 0.25A4TP20 | 25 mM Sodium Acetate | 4.0 | 9% Trehalose | PS20 | 0.25 | B039-40 | 1 mL |
| 1.0A4TP20 | 25 mM Sodium Acetate | 4.0 | 9% Trehalose | PS20 | 1.00 | B039-40 | 0.25 mL |
| 0.25A4TP20* | 25 mM Sodium Acetate | 4.0 | 9% Trehalose | PS20 | 0.25 | B039-70 | 1 mL |

After dialysis, the samples were tested by SE-HPLC to determine the aggregate content (Table 4). All formulations resulted in aggregate levels of less than 0.32%. Total peak area remained relatively constant throughout all of the samples demonstrating that protein adsorption onto the SE-HPLC column was not occurring.

TABLE 4

| Formulation | % Pre-peak | % Main Peak | Total Area |
| --- | --- | --- | --- |
| Ref. Std. | 0.20 | 99.80 | 22134.2 |
| 0.25A4SP20 (1 of 3) | 0.13 | 99.87 | 22492.4 |
| 0.25A4SP20 (2 of 3) | 0.14 | 99.86 | 22476.3 |
| 0.25A4SP20 (3 of 3) | 0.15 | 99.85 | 22627.4 |
| 0.25A4TP80 (1 of 3) | 0.14 | 99.86 | 23084.7 |
| 0.25A4TP80 (2 of 3) | 0.19 | 99.81 | 23131 |
| 0.25A4TP80 (3 of 3) | 0.18 | 99.82 | 23100.3 |
| 0.25A4TP20 (1 of 3) | 0.22 | 99.78 | 22704.7 |
| 0.25A4TP20 (2 of 3) | 0.16 | 99.84 | 22519.3 |
| 0.25A4TP20 (3 of 3) | 0.14 | 99.86 | 22548.7 |
| 1.0A4TP20 (1 of 3) | 0.07 | 99.93 | 23769.2 |
| 1.0A4TP20 (2 of 3) | 0.06 | 99.94 | 23696.5 |
| 1.0A4TP20 (3 of 3) | 0.12 | 99.88 | 23832.1 |
| 0.25A4TP20* (1 of 3) | 0.36 | 99.64 | 22504.9 |
| 0.25A4TP20* (2 of 3) | 0.32 | 99.68 | 22359.1 |
| 0.25A4TP20* (3 of 3) | 0.32 | 99.68 | 22492.8 |

Samples were incubated at 4° C. for four weeks and then retested for aggregate content (Table 5).

TABLE 5

| Formulation | % Pre-peak | % Main Peak | % Post-peak | Total Area |
| --- | --- | --- | --- | --- |
| Ref. Std. | 0.64 | 99.36 | 0.00 | 21332.8 |
| 0.25A4SP20 (1 of 3) | 0.21 | 99.79 | 0.00 | 21897.5 |
| 0.25A4SP20 (2 of 3) | 0.12 | 99.88 | 0.00 | 21922 |
| 0.25A4SP20 (3 of 3) | 0.15 | 99.85 | 0.00 | 21957.8 |
| 0.25A4TP80 (1 of 3) | 0.26 | 99.74 | 0.00 | 22887.8 |
| 0.25A4TP80 (2 of 3) | 0.31 | 99.69 | 0.00 | 22777.8 |
| 0.25A4TP80 (3 of 3) | 0.27 | 99.73 | 0.00 | 22946.7 |
| 0.25A4TP20 (1 of 3) | 0.13 | 99.87 | 0.00 | 22221 |
| 0.25A4TP20 (2 of 3) | 0.16 | 99.84 | 0.00 | 22395 |
| 0.25A4TP20 (3 of 3) | 0.15 | 99.85 | 0.00 | 22454.5 |
| 1.0A4TP20 (1 of 3) | 0.10 | 99.90 | 0.00 | 22997.3 |
| 1.0A4TP20 (2 of 3) | 0.09 | 99.91 | 0.00 | 23848.9 |
| 1.0A4TP20 (3 of 3) | 0.05 | 99.95 | 0.00 | 17866.2 |
| 0.25A4TP20* (1 of 3) | 0.31 | 99.69 | 0.00 | 22013.5 |
| 0.25A4TP20* (2 of 3) | 0.26 | 99.74 | 0.00 | 22049.4 |
| 0.25A4TP20* (3 of 3) | 0.27 | 99.73 | 0.00 | 22127.2 |

The S-Sepharose column was eluted with a salt gradient and the purified rhIFN beta-1b peak was pooled and analyzed by absorbance at 280 nm to determine the rhIFN beta-1b concentration. The pooled solution was adjusted to pH 4 and exchanged into 25 mM sodium acetate, pH 4, 9% w/v trehalose using tangential flow filtration. The polysorbate 20 content of the solution was assayed and adjusted as needed to 0.01-0.05% w/v by addition of a concentrated stock solution of polysorbate 20 (1% w/v) in 25 mM sodium acetate, pH 4, 9% w/v trehalose. The resulting solution was diluted with formulation buffer to yield 0.25 mg/mL rhIFN beta-1b, 25 mM sodium acetate, pH 4, 9% w/v trehalose, 0.01-0.05% polysorbate 20 (bulk drug substance) and sterile filtered (0.22 μm).

Purified, high-pressure refolded IFN-beta placed in liquid formulation maintained low aggregate levels, having an aggregate concentration of less than 0.5%, even after 4 weeks of incubation at 4° C. The aggregate concentration of the material produced after purification of high pressure refolding was significantly lower than what is available commercially as BETASERON (as reported in the Runkel reference, supra), which also contains HSA. Additionally, the aggregate content reported here was significantly less than the aggregate level of 6% published for a HSA-free liquid formulation (Shirley et al. 2002 patent application).

EXAMPLE 10

Data was developed that demonstrated that monomeric Bar 25 protein contains rhIFN beta-1b that is physicochemically and biologically comparable to monomeric rhIFN-beta 1b in the BETASERON product.

To demonstrate the comparability between rhIFN beta-1b in the BETASERON product and Bar 25 protein, an initial analytical comparability assessment (Table 6) was performed. Research grade Bar 25 protein was used in this study and was purified using only the first two column steps (blue affinity and IMAC). The Bar 25 protein was obtained by solubilizing in aqueous media, extracting into sec-butanol, precipitating with methanol, and then refolding using the best case refolding conditions. Because BETASERON contains 15 mg of human serum albumin and 0.30 mg rhIFN beta-1b, rhIFN beta-1b was isolated from the BETASERON formulation using RP-HPLC followed by SEC-HPLC. As a control, Bar 25 protein was also processed using the same procedures and compared to untreated Bar 25 protein. For the biological characterization, Bar 25 protein, BETASERON, and rhIFN beta-1b isolated from each formulation were evaluated.

TABLE 6

| Test | Assessment |
| --- | --- |
| Sequence and Identity Confirmation* | |
| N terminal sequence analysis | Equivalent to predicted sequence |
| Amino acid analysis | Amino acid content as predicted from sequence |
| Peptide mapping (reduced & non-reduced) | Comparable peptide map |
| Physicochemical Characterization* | |
| Molecular Weight/Mass | |
| MALDI-TOF | Comparable to theoretical molecular weight |
| SDS PAGE (reduced & non-reduced) | Comparable band patterns |
| Product Heterogeniety | |
| IEX LC | Comparable chromatograms |
| RP HPLC | |
| SEC HPLC (native & SDS) | |
| Structural Characterization | |
| UV-Vis absorption spectrum | Comparable absorption profiles |
| Analytical ultracentrifugation | Comparable sedimentation times and predicted molecular weight |
| Far and near UV circular dichroism | Comparable secondary and tertiary structure |
| Fluorescence | Comparable emission spectra |
| Biological Characterization | |
| Bioassay** | Comparable specific activity (MIU/mg) |
| Receptor binding (competition) | Comparable receptor binding |

*Analyses performed on rhIFN beta-1b isolated from BETASERON and Bar 25 protein as well as untreated (stock) Bar 25 protein;
**Bioassay performed by PBL Biomedical Laboratories using A549 cells and EMC viral challenge.

N-terminal sequence and amino acid analyses demonstrated that the rhIFN beta-1b isolated from BETASERON and Bar 25 protein were comparable and matched the predicted sequence. Peptide mapping analyses performed by Lys-C digest and RP-HPLC indicated that the peptide maps were comparable for rhIFN beta-1b isolated from BETASERON and Bar 25 protein as well as the control untreated Bar 25 protein. One peptide containing Asn28 in Bar 25 protein was shifted to an earlier elution time consistent with deamidation. This result was expected because research grade Bar 25 protein was not purified using the last column step, S Sepharose, which is intended to remove deamidated rhIFN beta-1b.

The molecular weight by MALDI TOF analysis was 19877 and 19879 Da for rhIFN beta-1b isolated from BETASERON and Bar 25 protein, respectively. The band pattern for both reduced and non-reduced SDS PAGE gels was comparable for both products.

A comparison of the product heterogeneity for rhIFN beta-1b isolated from BETASERON and Bar 25 protein as well as untreated Bar 25 protein demonstrated comparability with the exception of the deamidated impurity present in rhIFN beta-1b in the research grade Bar 25 protein sample. The SE-HPLC (native) analyses revealed comparable chromatographic profiles with predominantly monomeric rhIFN beta-1b (99.1% and 100% for sample from BETASERON and Bar 25 protein, respectively). Untreated Bar 25 protein (research grade) was 99% monomeric rhIFN beta-1b by native SE-HPLC, indicating that the manufacturing process described above successfully produces drug substance essentially free of protein aggregates.

Structural characterization indicated that the rhIFN beta-1b in BETASERON and Bar 25 protein as well as untreated Bar 25 protein was comparable as measured by spectroscopic absorbance (200-400 nm), analytical ultracentrifugation, far ultraviolet circular dichroism, and fluorescence. Near ultraviolet circular dichroism was not performed due to the low rhIFN beta-1b concentrations of the samples. These results confirmed the comparability of the secondary and tertiary structure of rhIFN beta-1b in both products.

The biological activity of rhIFN beta-1b in BETASERON and Bar 25 protein was 28 MIU/mg and 55 MIU/mg, respectively. The biological activity of untreated Bar 25 protein was 86 MIU/mg.

Overall, these results demonstrate that the rhIFN beta-1b isolated from BETASERON was comparable to rhIFN beta-1b in Bar 25 protein as measured by physicochemical and biological assays.

Sample Preparation

For the physicochemical characterization of BETASERON, rhIFN-beta1b must be isolated from the large excess of HSA. The following protocol was used to prepare HSA-free BETASERON:

Resuspend each vial of BETASERON (lot WA8236A, exp date 10/08) in 0.6 ml DI water. Three vials per purification were used and a total of 20 purification processes were performed (20 vials total) to yield 10 mg purified BETASERON.

Load the interferon beta solution onto a C18 Phenomenex 10.0×250 column 5 uM (SN 000-4053-NO) using a Beckman System Gold HPLC equipped with a 2 ml loop.

Elute the proteins using a gradient from 20-60% B over 60 min at 2 mL/min, collecting two mL fractions. Buffer A was 0.1% TFA in HPLC grade water and buffer B was 0.1% TFA in acetonitrile. HSA elutes at 27 min and BETASERON elutes at 55 min with baseline separation between the two proteins. BETASERON was pooled based on absorbance at 215 nm. The procedure was repeated a total of four times and all runs were pooled together.

Dialyze the pooled fractions overnight against 20 mM sodium acetate pH 4.0 in Snake Skin dialysis tubing (Pierce, 3500 MWCO) at 4° C. with stirring.

Concentrate the protein pool using a 50 ml Amicon stirred cell with a 10 MW cutoff membrane and pressurized at 40 psi. Pools were concentrated to yield 0.2 to 0.8 mg/mL rhIFN-beta1b.

For the N-terminal sequencing (Section 3a1), amino acid analysis (Section 3a2) and structural characterization (Section 4), trace amounts of HSA were removed from the final pool of BETASERON using an anti-HSA affinity resin (Satorius, Vivapure) per manufacturer's protocol. For the other analytical procedures, control samples consisting of BETASERON diluted to the expected HSA levels were used to account for trace levels of HSA in the purified rhIFN-beta1b from BETASERON.

Purified rhIFN-beta1b samples were stored in a −70° C. freezer until analysis.

For comparison purposes, Bar 25 protein was treated using the same RP-HPLC purification procedure. For each purification process cycle, 2 ml of an IMAC pool from refold (lot# 070507) at 333 µg/ml was used as starting material following the above protocol for BETASERON from steps 2 through 7. The IMAC pool was selected because the subsequent purification step for Bar 25 protein (S Sepharose) containing surfactant that would interfere with purification using the above procedure. This purification process was repeated for 20 cycles to yield 10 mg of purified rhIFN-beta1b from Bar 25 protein.

For the bioassay and receptor binding assay, BETASERON prepared according to the product insert, purified rhIFN-beta1b from this procedure applied to BETASERON and Bar 25 protein, and untreated Bar 25 protein was analyzed.

Analytical Characterization Methods

N-terminal Amino Acid Sequence Analysis

Representative samples of rhIFN-beta1b purified from Bar 25 protein and BETASERON were evaluated for primary amino acid sequence by Edman sequencing Amino Acid Sequence Analysis and Extinction Coefficient Representative samples of rhIFN-beta1b purified from Bar 25 protein and BETASERON were hydrolyzed in 6 M hydrochloric acid, and the amino acid composition was determined by ion-exchange chromatography using post-column derivitization with ninhydrin reagent. An extinction coefficient was determined by comparison to absorbance readings at 280 nm.

Peptide Mapping

Protein samples of rhIFN-beta1b purified from Bar 25 protein and BETASERON were digested using with 5% w/w endoproteinase Lys-C in 100 microliters of PBS pH 7.6, 1 mM EDTA for 16 hr at ambient temperature. The peptide mixture was loaded onto a Vydac C18 RP-HPLC column (218TP54). The column was developed with the following gradient where A=water, 0.1% TFA and B=acetonitrile, 0.08% TFA: 0-63% B in 70 min, 63-80% in 10 min. Peptide peaks were detected at 214 nm with a Beckman Gold HPLC.

Disulfide Bridge—Non-Reduced

The above peptide mapping protocol was followed, with the exception that 10 mM DTT was added to digestion mixture prior to RP-HPLC analysis.

MALDI-TOF

Representative samples of rhIFN-beta1b purified from Bar 25 protein and BETASERON were formulated in the same matrix, and the molecular mass was determined by mass spectroscopy using time-of-flight analysis.

SDS PAGE Electrophoresis—Reduced and Non-Reduced Silver

Gel: Novex 10-20% Tris Glycine 1.5 mm 10, 12 or 15 well

Apparatus: XCell SureLock Mini-Cell

Loading Buffer: 5× Sample Buffer (10 mM DTT when reduced), 50 mM Tris pH 6.8, 2% SDS, 0.1% bromophenol blue, 20% glycerol Running Buffer: 1× Tris-Glycine SDS Running Buffer (Novex)

Voltage: 125 V constant

Gels were stained using a GE BioSciences Plus One silver stain kit or the conventional coomassie blue stain.

| Cation Exchange | |
| --- | --- |
| HPLC: | Agilent HP 1100 |
| Column: | Dionex WCX 10 4 × 250 mm P/N 054993 |
| Solvents: | A: 20 mM Sodium Acetate, 0.05% Zwittergent surfactant, pH 5.0 |
| | B: A + 1M NaCl |
| Flow Rate: | 0.8 mL/min |
| Temp: | Ambient |
| Injection target: | 25 µg |
| Absorbance: | 214 nm |
| | Time (min)   % B |
| Gradient: | 0     1 |
| | 5     1 |
| | 45    40 |
| | 46    100 |
| | 48    100 |
| | 48.1  1 |
| | 55    1 |

| Reversed Phase-HPLC (RP-HPLC) Method | |
| --- | --- |
| HPLC: | Agilent HP 1100 |
| Column: | C4 Jupiter 5µ 300 A 250 × 4.6 mm |
| Solvents: | A: Water, 0.1% TFA |
| | B: Acetonitrile, 0.1% TFA |
| Flow Rate: | 1 ml/min |
| Temp: | 30° C. |
| Injection: | 50 µl |
| Absorbance: | 215 nm, 280 nm |
| | Time (min)   % B |
| Gradient: | 0     20 |
| | 21    53 |
| | 45    68 |
| | 50    100 |
| | 60    20 |

| SEC-HPLC (native) | |
| --- | --- |
| HPLC: | Agilent HP 1100 |
| Column: | Toyo G2000 SWXL |
| Solvents: | 10 mM HCl |
| Flow Rate: | 0.5 ml/min |
| Temp: | RT |
| Injection: | 50 µl |
| Absorbance: | 215 nm, 280 nm |
| Gradient: | Isocratic |

UV-Vis rhIFN-beta1b purified from BETASERON and Bar 25 protein were analyzed for absorption spectra from 200 to 400 nm. rhIFN-beta1b from both products were formulated at the same concentration in the same formulation. The system were blanked against the placebo formulation. The resulting spectra were overlaid and compared between the two products directly.

Analytical Ultracentrifugation Profile rhIFN-beta1b purified from BETASERON and Bar 25 protein were formulated at the same protein concentration and in the same formulation. The samples were centrifuged at 55,000 RPM and the sedimentation monitored by absorbance. Data analysis was conducted by SEDFIT, following the method prescribed in Gabrielson et. al.

Far and Near UV Circular Dichroism Spectroscopy rhIFN-beta1b purified from BETASERON and Bar 25 protein were analyzed for secondary (Far UV) and tertiary (Near UV) structure using circular dichroism. The rhIFN-beta1b from both products were formulated at the same concentration in the same formulation. Two scans were averaged and corrected for buffer absorbance. For near UV CD spectroscopy, 0.25 mg/ml protein in a 1 cm quartz cuvette was scanned from 250 nm to 340 nm. For far UV CD spectroscopy, 0.1 mg/ml of protein was scanned from 200 to 260 nm in a quartz cuvette with a pathlength of 0.1 cm. The mean residue molar ellipticity (deg-cm$^2$/dmol) was calculated.

Fluorescence

Intrinsic fluorescence of rhIFN-beta1b purified from BETASERON and Bar 25 protein was monitored. Excitation of the intrinsic tryptophan fluorophores occurs at 295 nm. Center of mass spectral shifts was monitored in the emission wavelength range of 300-400 nm. Fluorescence intensity was determined at the peak of the emission spectra.

Bioassay

A bioassay was performed using the cytopathic effect (CPE) assay. The assay employed human lung carcinoma cells (A549) treated with rhIFN-beta1b and then challenged with encephalomyocarditis (ECM) virus. The CPE assay was performed against the WHO International Standard of IFN-beta, Gb23-902-531 (natural) using A549 cells and EMC viral challenge. Each sample had 3 independent runs and average potency was reported.

Receptor Binding (Competition Assay)

Receptor binding competition assays were performed using purified rhIFN-beta1b from Bar 25 protein and BETASERON, and unprocessed Bar 25 protein and BETASERON. The assay was performed using the recombinant human interferon-alpha/beta R2 receptor Fc (rhIFN-R2 Fc) chimera (R&D Systems, Product 4015-AB). This receptor binds both interferon-alpha and interferon-beta. $^{125}$I-human interferon-alpha ($^{125}$I-IFN-alpha) was used as the competing reagent to avoid potential effects of radiolabeling on the rhIFN-beta1b products. rhIFN-R2 Fc was coated onto ELISA plates and $^{125}$I-IFN-alpha was added at a fixed concentration to each well. After incubation, the 125I-IFN-alpha was competed off with the rhIFN-beta1b sample at different concentrations (serial dilutions). Unlabeled IFN-alpha was used as a control. The amount of $^{125}$I-IFN-alpha remaining bound to rhIFN-R2 Fc after the competition was measured and plotted as a function of the rhIFN-beta1b concentration. The resulting curves for each product and purified rhIFN-beta1b sample were compared.

Overall, these results demonstrate that the monomeric rhIFN beta-1b isolated from BETASERON was comparable to rhIFN beta-1b produced through high pressure refolding (Bar 25 protein) as measured by physicochemical and biological assays. However, it should be noted that only the monomer was comparable between the two products. Aggregates of IFN-beta that are present in BETASERON would have very different secondary structures (largely non-native beta sheet) and lower bioavailability. Earlier examples demonstrate that high pressure refolded IFN-beta leads to a pharmaceutical drug product that has a lower aggregate content that either BETASERON or HSA-free IFN-beta free formulations generated from SDS refolding methods.

EXAMPLE 11

Single dose non-GLP pharmacokinetic studies were conducted in rats, cynomolgus monkeys, and rhesus monkeys to examine the pharmacokinetics and pharmacodynamics of Bar 25 protein relative to the BETASERON product.

Pharmacokinetics of Bar 25 Protein in Rats

To characterize the pharmacokinetics of Bar 25 protein, jugular vein cannulated Sprague Dawley rats (4 males per group) were administered 0.2 mg rhIFN beta-1b/kg Bar 25 protein by subcutaneous (SC) injection. For comparison, one group of rats was also given a subcutaneous administration of BETASERON at the same dose. BETASERON was prepared according to the package insert using the diluent supplied and diluted from 0.25 to 0.10 mg/mL rhIFN beta-1b with buffer (10 mM sodium acetate, pH 4, 9% w/v trehalose). Bar 25 protein was formulated at 0.10 mg/mL rhIFN beta-1b in 10 mM sodium acetate, pH 4, 9% w/v trehalose.

Figure 16:
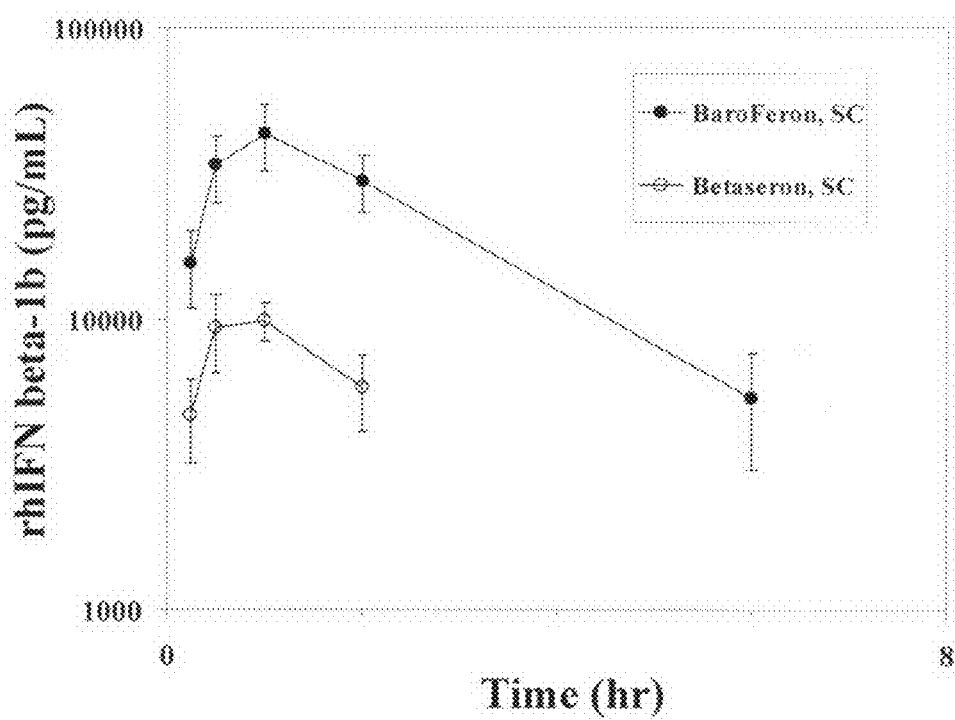
FIG. 16 is a chart showing plasma concentration of IFNs in Sprague Dawley rats.

As expected, animals did not exhibit any clinical observations attributable to treatment because rhIFN beta-1b was not pharmacologically active in rodents due to the species specificity of interferon beta. The absolute bioavailability after SC administration of Bar 25 protein was approximately 1.5%. See FIG. 16. The maximum observed plasma rhIFN beta-1b concentration occurred from 0.98 to 1.01 hours after SC administration of Bar 25 protein. The relative bioavailability of BETASERON compared to Bar 25 protein after SC administration was 28% suggesting that BETASERON was not well absorbed after SC administration. The lower bioavailability of BETASERON compared to Bar 25 protein may be caused by the presence of aggregated rhIFN beta-1b and/or human serum albumin in the BETASERON formulation. $T_{max}$ and $t_{1/2}$ were comparable between subcutaneously delivered Bar 25 protein and BETASERON.

Pharmacokinetics and Pharmacodynamics of Bar 25 Protein in Cynomolgus Monkeys

The pharmacokinetics and pharmacodynamics of Bar 25 protein were assessed in non-naïve cynomolgus monkeys. A dose expected to cause minimal clinical adverse events (0.05 mg rhIFN beta-1b/kg) was selected for this study. Monkeys (n=4/group) were administered bolus SC injections of Bar 25 protein. Bar 25 protein was formulated at 0.25 mg rhIFN beta-1b/mL in 10 mM sodium acetate, pH 4, 9% w/v trehalose. For comparison, one group of monkeys was injected SC with the same rhIFN beta-1b dose of BETASERON. BETASERON was prepared according to the package insert using the diluent provided. Another group of monkeys was dosed IM with AVONEX® provided as a prefilled syringe with 0.06 mg/mL rhIFN beta-1a (same total dose as Bar 25 protein). Due to the low rhIFN beta-1a concentration in AVONEX®, all monkeys in this group required more than one injection. The injections were split over two or more syringes and injected simultaneously at adjacent sites (within 10 cm).

Plasma was collected for rhIFN beta concentrations at various time points rhIFN beta was determined by an ELISA method developed by Prevalere Life Sciences using rhIFN beta-1b (Bar 25 protein). The lower limit of quantitation in the presence of monkey serum was 1000 pg/mL (1 ng/mL). Neopterin, which is expressed by monocytes activated by type I interferons, was chosen as a pharmacodynamic (PD) marker. Neopterin levels were determined with a commercial kit that was qualified by Prevalere for use on monkey plasma samples.

Figure 17:
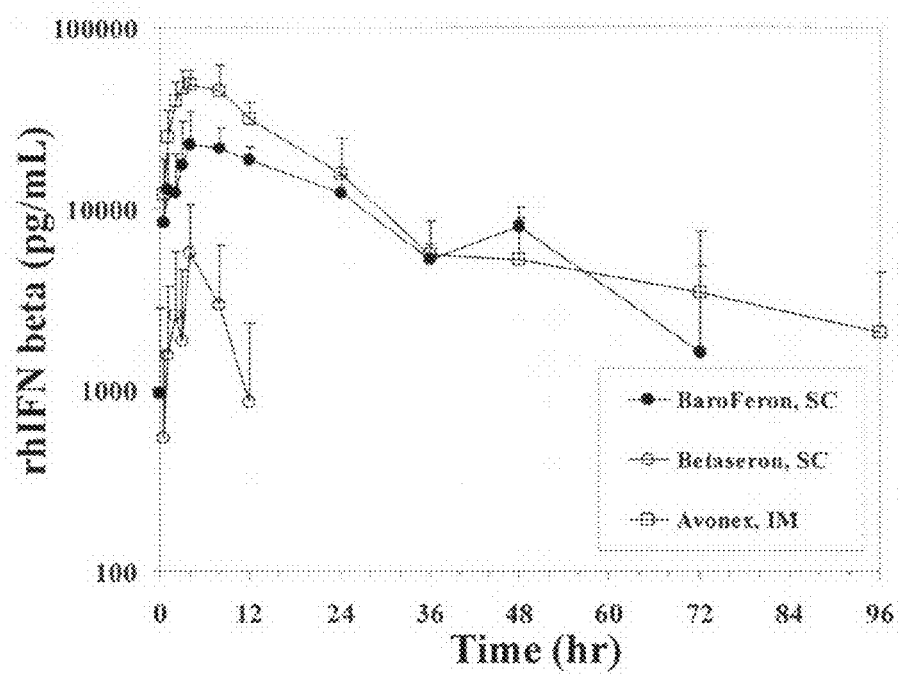
FIG. 17 is a chart showing plasma concentration of IFNs in Cynomolgus monkeys.

For BETASERON, only two monkeys had consistently detectable levels due to the apparent poor absorption of BETASERON after SC administration. Unlike BETASERON, the Bar 25 protein dose was completely absorbed after IM and SC administration as measured by total exposure ($AUC_{0-\infty}$, or $AUC_{0-n}$) compared to IV administration. The relative bioavailability of BETASERON compared to Bar 25 protein both administered SC was approximately 7% ($AUC_{0-\infty}$), while the relative bioavailability of Bar 25 protein compared to AVONEX® both administered IM was approximately 90% ($AUC_{0-\infty}$). See FIG. 17. The lack of rhIFN beta aggregates and/or absence of human serum albumin in Bar 25 protein may yield the greater bioavailability compared to BETASERON.

The pharmacokinetics of Bar 25 protein were also assessed in non-naïve rhesus monkeys. The same dose (0.05 mg rhIFN beta-1b/mg) and assays previously utilized in the cynomolgus monkey study were used in this study. This study was performed due to conflicting reports of the biological response to rhIFN beta in cynomolgus and rhesus monkeys. The terminal half-life of IFN-beta was 22.33±5.38 hr and comparable to that observed in cynomolgus monkeys.

Figure 18:
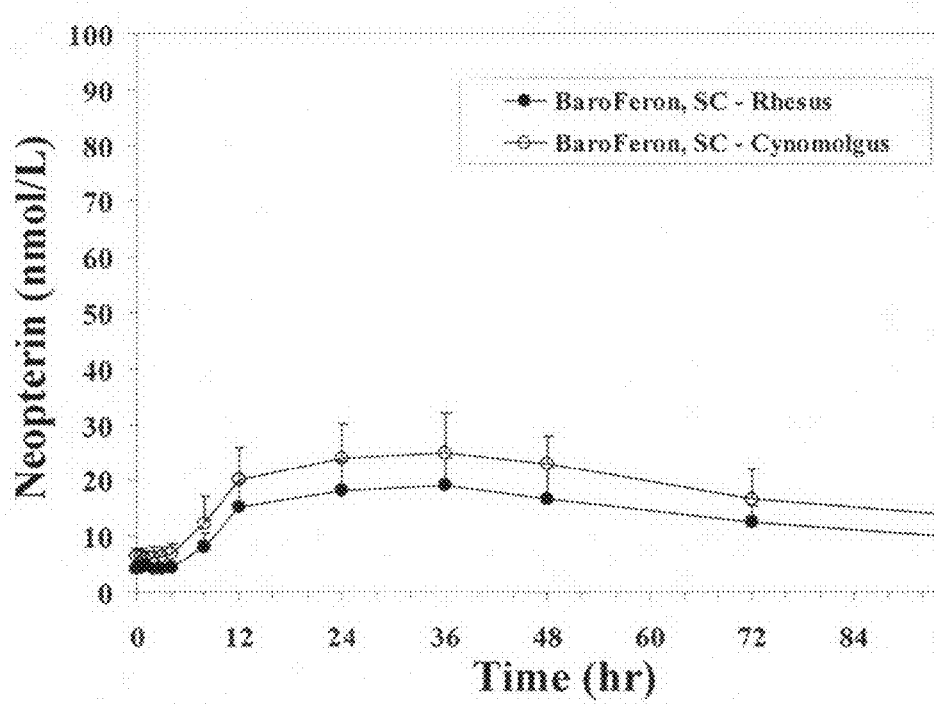
FIG. 18 is a chart showing plasma concentration of IFNs in Cynomolgus monkeys.
Figure 19:
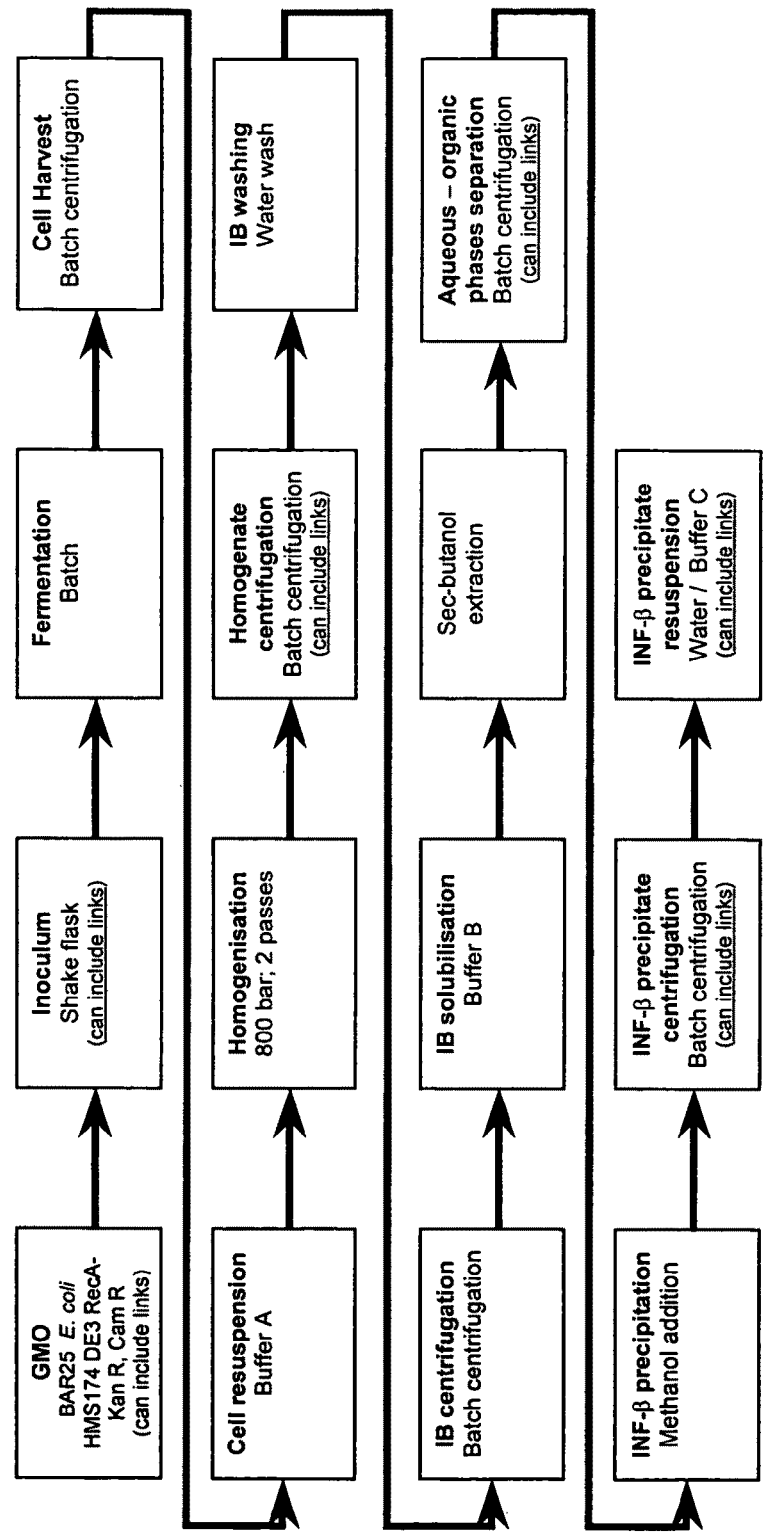
FIG. 19 is a schematic diagram of fermentation and primary recovery processes.
Figure 20:
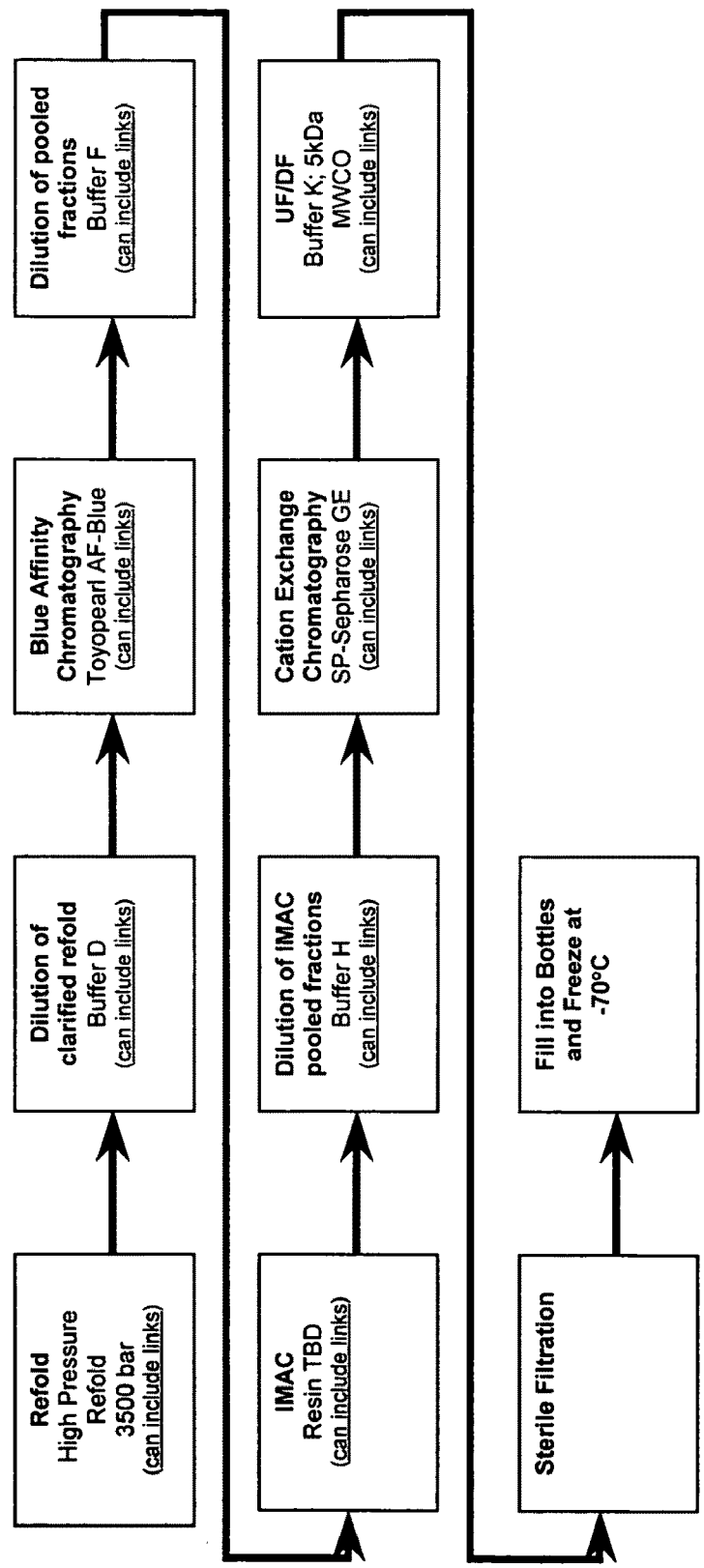
FIG. 20 is a schematic diagram of a secondary recovery process.
Figure 21A:
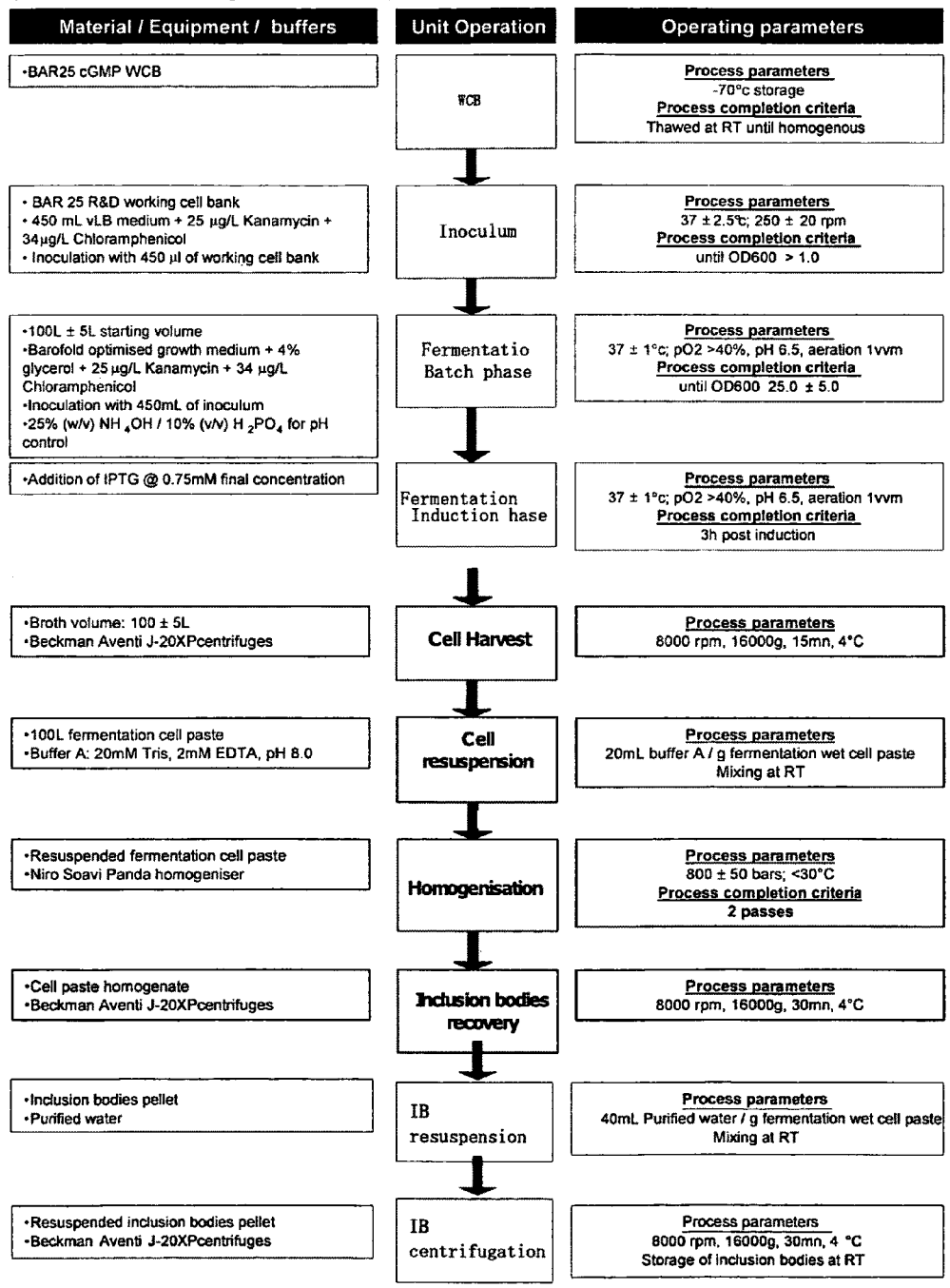
FIG. 21A is a schematic diagram of a fermentation and primary recovery process.
Figure 21B:
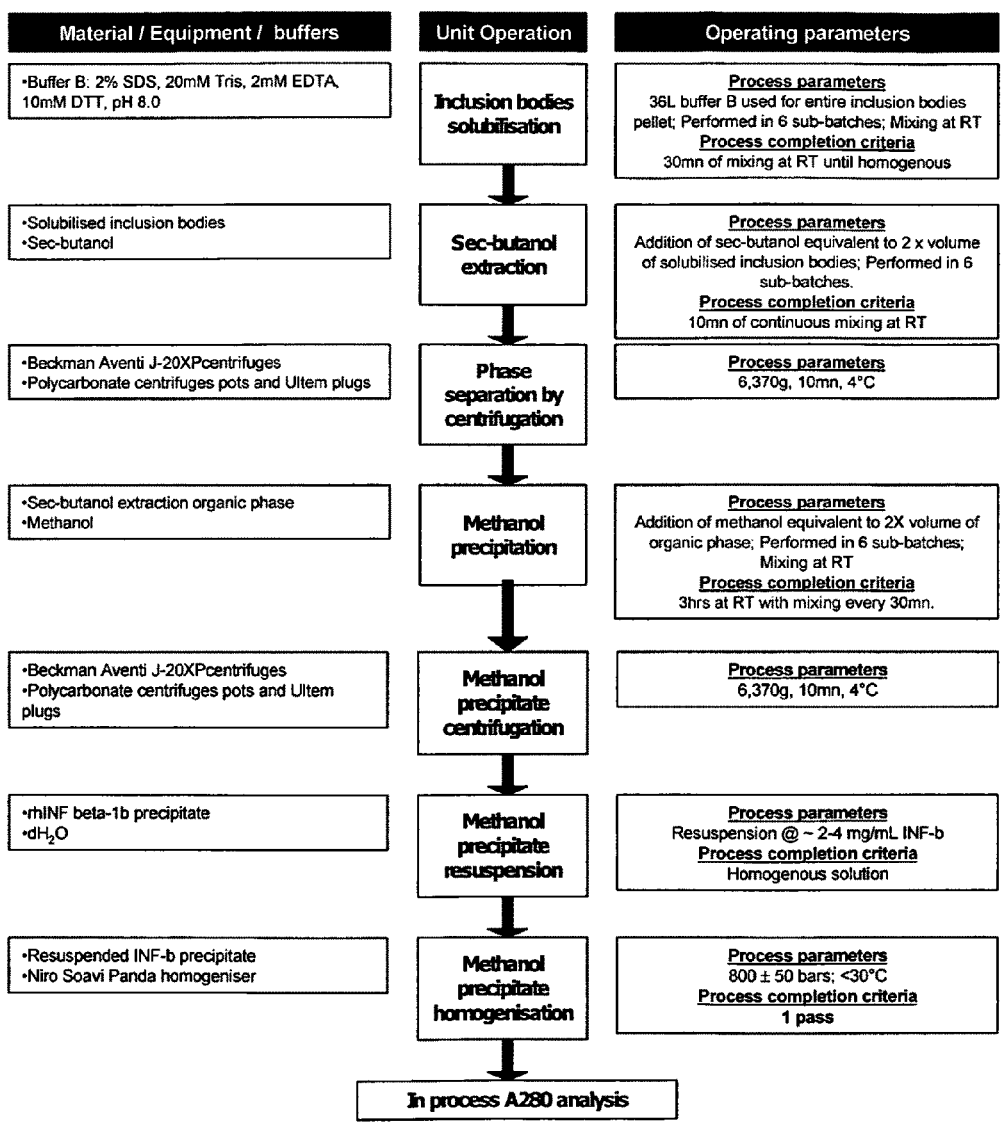
FIG. 21B is a continuation of the schematic diagram of the fermentation and primary recovery process of FIG. 21A.

Plasma Levels of Neopterin in Cynomolgus and Rhesus Monkeys after Administration of rhIFN Beta The pharacodynamic marker, neopterin, was measured in both cynomolgus and rhesus monkeys, as is shown in FIG. 18. Neopterin is a secondary pharmacodynamic marker that requires monocyte activation and subsequent expression of neopterin. Neopterin was expressed after dosing of Bar 25 protein, demonstrating bioavailability of the drug in a similar manner as BETASERON.

Bar 25 protein was well tolerated (i.e., no clinical signs noted) following single IV, IM, and SC doses of 0.2 and 0.05 mg/kg in Sprague Dawley rats and rhesus and cynomolgus monkeys, respectively.

Expected pharmacodynamic responses were achieved following the administration of Bar 25 protein in both cynomolgus and rhesus monkeys, demonstrating bioavailability of the drug in animal models.

rhIFN beta-1b exposure in rats and cynomolgus monkeys was higher following SC administration with Bar 25 protein relative to BETASERON. The increase in exposure could be related to differences in formulation and/or enhanced bioavailability due to reduced aggregation at the site of injection.

EXAMPLE 12

The purpose of this example is to demonstrate the effect of homogenization on refolding after larger-scale butanol extraction and methanol precipitation.

The effect of homogenization of methanol precipitated Bar25 (described as "larger scale homogenization" see Methods) on the refolding of Bar25 was examined. Non-homogenized and homogenized methanol precipitated Bar25 was pressure treated at 3500 bar in a refolding buffer containing 50 mM CAPS (pH 10), 1.3 mM cysteine, 0.3 mM cystine, 0.05% Zwittergent 3-14 surfactant for 7 hours at 25° C. Depressurization was conducted at a rate of 250 bar/five minutes. Homogenization resulted in an improvement of the soluble material present after refolding, with a final percentage of soluble material being 14 and. 28% respectively.

TABLE 7

| Refold sub-batch | Target protein concentration [mg/mL] | Refold time [h] | Volume [mL] | Protein concentration [mg/mL] | | | Amount of protein [mg] | | | Refold yield (%) |
| --- | --- | --- | --- | --- | --- | --- | --- | --- | --- | --- |
| | | | | SDS-PAGE | AU [280 nm] | RP-HPLC | SDS-PAGE | AU [280 nm] | RP-HPLC | |
| Sub-batch 1 | 0.50 | 7.0 | 240.0 | 0.17 | 0.27 | | 40.1 | 64.8 | | |
| Sub-batch 2 | 0.50 | 7.0 | 240.0 | 0.15 | 0.23 | | 36.3 | 55.7 | | |
| Sub-batch 3 | 0.50 | 7.0 | 240.0 | 0.13 | 0.23 | | 32.1 | 54.8 | | |
| Sub-batch 4 | 0.50 | 7.0 | 240.0 | 0.14 | 0.23 | | 33.6 | 56.3 | | |

TABLE 7-continued

| Refold sub-batch | Target protein concentration [mg/mL] | Refold time [h] | Volume [mL] | Protein concentration [mg/mL] | | | Amount of protein [mg] | | | Refold yield (%) |
|---|---|---|---|---|---|---|---|---|---|---|
| | | | | SDS-PAGE | AU [280 nm] | RP-HPLC | SDS-PAGE | AU [280 nm] | RP-HPLC | |
| Sub-batch 5 | 0.50 | 7.0 | 240.0 | 0.15 | 0.22 | | 36.8 | 53.8 | | |
| Sub-batch 6 | 0.50 | 7.0 | 240.0 | | 0.55 | | | 133.2 | | |
| Sub-batch 7 | 0.50 | 7.0 | 240.0 | | 0.58 | | | 139.3 | | |
| Sub-batch 8 | 0.50 | 7.0 | 240.0 | | 0.54 | 0.13 | | 129.8 | 30.2 | 23.3 |
| Sub-batch 9 | 0.50 | 7.0 | 240.0 | | 0.55 | 0.16 | | 131.3 | 37.4 | 28.5 |
| Sub-batch 10 | 0.50 | 7.0 | 240.0 | | 0.51 | 0.14 | | 123.0 | 34.4 | 28.0 |
| Sub-batch 11 | 0.50 | 7.0 | 240.0 | | 0.50 | 0.15 | | 119.1 | 36.1 | 30.3 |
| Sub-batch 12 | 0.50 | 4.0 | 240.0 | | 0.55 | 0.12 | | 131.6 | 29.4 | 22.3 |
| Sub-batch 13 | 0.50 | 4.0 | 240.0 | | 0.55 | 0.19 | | 133.0 | 44.4 | 33.4 |

Key points:
All analysis done on clarified refold (0.2 μm filtered Sartobran 300)
Sub-batches 1 till 5 used non-homogenised INF-β ppt
RP-HPLC quantification value based on integration of refolded INF-β peak and hence does not represent value of total protein in sample
Refold yield determined as percentage of refolded INF-β (RP-HPLC value) to total protein (A280 value) in clarified refold "Larder Scale Methanol Precipitate"

A pellet from inclusion bodies (1 g wet cell weight per 40 ml of buffer) was suspended in 7 L solubilization buffer (2% SDS, 20 mM Tris, pH 8.0, 2 mM EDTA, 10 mM DTT). The mixture was stirred for 30 min at a temperature of 17° C. Next 14 L of sec-butanol was added followed by 10 minutes of mixing to allow extraction of IFN beta into the organic phase. The cloudy solution was centrifuged for 10 min. The top organic layer was carefully removed from the small aqueous layer. A precipitate usually was present at the interface of the two liquids and at the bottom of the bottle. Next approximated 220 L of methanol (2× the volume of the organic layer) was added. The liquids were thoroughly mixed and allowed to sit at 4° C. for 2 hrs. A white fluffy precipitate will form. This precipitate (insoluble IFN beta) was separated from the mixture by centrifugation. The protein ppt should be stored as a suspension in a minimal amount of WFI (endotoxin free) water as it has a tendency to desiccate when frozen as a pellet for extended periods of time. The pellet was resuspended in a sufficient amount of water such that the final mixture was approximately 2-3 mg IFN-beta/mL. The methanol precipitate suspension was stored at −20° C. The final concentration of IFN beta can be determined by dissolving a small aliquot of the suspension in 6 M guanidine and measuring the absorbance at 280 nM. (IFN beta has an O.D. of 1.5 at 1 mg/mL).

Homogenization was conducted by implementing a mechanical homogenizer until the precipitate was suspended to a milky solution.

High pressure refolding was conducted for 7 hours at a scale of 50 ml. All other solution conditions, pressure and temperature conditions, and pressurization and depressurization rates were as has been described.

The amount of soluble material was determined by A280 absorbance on the supernatant after refold clarification.

At larger scale, the methanol precipitation step can lead to aggregates that are less amenable to high pressure treatment. Homogenization of this material results in material that can be refolded to higher yields compared to methanol precipitated material that was not homogenized.

EXAMPLE 13

This example describes an alternative technique to make recombinant human interferon beta-1b (rhIFN beta-1b) according to SEQ ID No. 2. A schematic diagram of fermentation and primary recovery processes as described in this Example is shown in FIG. 19.

As an overview, rhIFN beta-1b was expressed in *E. coli* as insoluble inclusion bodies. The gene sequence was inserted in a plasmid, pET24a+, containing a T7 promoter with a kanamycin resistance gene. The *E. coli* host strain, HMS174 (DE3), expresses the T7 RNA polymerase. In addition, the pRARE2 plasmid was inserted in the strain. pRARE2 carries the chloramphenicol resistance gene and a set of tRNA genes for rare *E. coli* codons present in the rhIFN beta-1b gene. In order for the strain to retain both plasmids, this expression strain requires the use of kanamycin and chloramphenicol in the fermentation media. After fermentation, cells were isolated by centrifugation and lysed by homogenization. The inclusion bodies were recovered by centrifugation. After isolation and washing, insoluble rhIFN beta-1b was solubilized with SDS and DTT, extracted with sec-butanol and precipitated with methanol to yield a precipitate that was enriched in rhIFN beta-1b. The methanol precipitate was homogenized to generate a homogeneous suspension. rhIFN beta-1b was refolded without chaotropes using BaroFold Inc.'s (Boulder, Colo.) proprietary high pressure technology, PreEMT.

A schematic diagram of the secondary recovery processes as described in this Example is shown in FIG. 20. The refolded rhIFN beta-1b was then captured on a blue affinity column. The refolded fraction eluted from the column was further purified by a chelating column (IMAC-copper), and a cation exchange column (S Sepharose). The purified pool collected from the last column step was formulated and filtered (0.22 μm) to yield the bulk drug substance (0.25 mg/mL rhIFN beta-1b, 25 mM sodium acetate, pH 4, 9% w/v trehalose, 0.01-0.05% polysorbate 20).

Cells from a Working Cell Bank derived from the Master Cell Bank were grown in shake flasks as inculum to the 100 L fermentor. During the fermentation process, the optical density of the culture (600 nm; OD600) was monitored and induction with 0.75 mM isopropyl-β-D-thiogalactoside (IPTG) was performed once the OD600 reaches 25±5. After induction, the culture was allowed to continue growth for 3 hr. Upon harvest, the wet cell weight (WCW) was used to determine the volume of cell resuspension buffer prior to homogenization (40 mL buffer per g WCW), as well as the volume of inclusion body solubilization buffer (10 mL buffer per g WCW).

After solubilization, solvent extraction, precipitation, and homogenization, the methanol precipitate concentration was determined and then diluted with refolding buffer to yield 0.5 g/L of rhIFN beta-1b. The refold solution (~8.2 L) was pumped into a bioprocess bag (Hyclone) placed inside the 10

L PreEMT high pressure vessel. The remaining volume was filled with distilled water or WFI. There was no product contact between the surrounding water or the vessel walls because the rhIFN beta-1b solution was sealed within the bioprocess bag. Pressurization parameters (ramp rate, pressure, and hold time) were computer controlled and data logged. After each refold cycle, the final solution was pumped out of the bioprocess bag, filtered (0.20 □m), and analyzed by absorbance at 280 nm, RP HPLC, and SDS PAGE to assess yield and purity.

The clarified refold solution was loaded onto a blue affinity column (4 mg rhIFN beta-1b/mL resin) and step eluted with propylene glycol. The current pooling criteria allow for pooling the single peak eluted from the column during the step gradient and the pool was analyzed by absorbance at 280 nm and RP HPLC. The pooled fractions from the blue affinity column were loaded at 2.5±0.5 mg/mL rhIFN beta-1b onto the IMAC column and eluted with an imidazole gradient. The second elution peak was pooled and analyzed by absorbance at 280 nm and RP HPLC. The IMAC pool was conditioned in phosphate buffer, pH 6.7 containing 50% propylene glycol, 0.005% Sulfobetaine-14, and 0.01% polysorbate 20 (~10 fold dilution), and loaded onto the S Sepharose column. The S Sepharose column was eluted with a salt gradient and the purified rhIFN beta-1b peak was pooled and analyzed by absorbance at 280 nm to determine the rhIFN beta-1b concentration. The pooled solution was adjusted to pH 4 and exchanged into 25 mM sodium acetate, pH 4 using tangential flow filtration. 9% w/v trehalose was obtained by adding a concentrated stock solution of trehalose in 25 mM sodium acetate, pH 4. The polysorbate 20 content of the solution was assayed and adjusted as needed to 0.01% w/v by addition of a concentrated stock solution of polysorbate 20 (1% w/v) in 25 mM sodium acetate, pH 4, 9% w/v trehalose. The resulting solution was diluted with formulation buffer to yield 0.25 mg/mL rhIFN beta-1b, 25 mM sodium acetate, pH 4, 9% w/v trehalose, 0.01% polysorbate 20 (bulk drug substance) and sterile filtered (0.22 μm). The bulk drug substance was stored frozen at −70° C. in polycarbonate bottles.

A current formulation (25 mM sodium acetate, pH 4, 9% w/v trehalose, 0.01% w/w polysorbate 20) stabilizes rhIFN beta-1b during freeze-thaw, agitation, and short-term exposure to elevated temperature (e.g., 40° C.). Low pH and low salt conditions help to maintain the solubility of the protein. Trehalose inhibits freeze-thaw induced protein aggregation, and polysorbate 20 prevents protein aggregation during agitation.

A preferred container used for a drug product incorporating the treated protein was a 3 cc glass vial (USP Type 1 glass) with a 13 mm opening (Table 8). The closure system was a 13 mm Teflon faced grey butyl stopper (or equivalent) covered with a 13 mm flip-off foil crimp top seal.

TABLE 8

Components for Container/Closure System

| Component | Supplier |
| --- | --- |
| 3 ml clear, 13 mm opening, USP Type 1 glass vial | Fisher Scientific/Wheaton |
| Stopper 4416/50 Gray 20 mm | West |
| Aluminum Seal white flip off 20 mm | West |

An illustrative drug formulation was 25 mM sodium acetate, pH 4, 9% w/v trehalose, 0.01-0.05% Polysorbate 20. The drug substance will be filled at 1.2 mL of 0.25 mg/mL rhIFN beta-1b per vial (0.30 mg rhIFN beta-1b per vial).

EXAMPLE 14

IFN-β was produced by small scale fermentation (shake flask) and the same downstream processing steps as in Example 13 except for the last purification step. Instead of the S Sepharose column step, the protein was purified with another blue affinity column. The resulting rhIFN beta-1b was partially deamidated. The initial stability was assessed via changes in the RP HPLC, SEC HPLC (native and SDS), and SDS PAGE during storage. The results from this study demonstrated that rhIFN beta-1b was not prone to aggregation in the drug formulation after 4 weeks at 40° C. as measured by native SEC HPLC and SDS PAGE. No significant change in product heterogeneity as measured by RP HPLC was observed after 4 weeks at the recommended storage condition (2-8° C.).

EXAMPLE 15

To demonstrate the comparability between rhIFN beta-1b in the BETASERON product and IFN-β prepared in accordance with Example 14, an initial analytical comparability assessment (Table 9) was performed. Because BETASERON product contains 15 mg of human serum albumin and 0.30 mg rhIFN beta-1b, rhIFN beta-1b was isolated from the BETASERON formulation using RP HPLC followed by SEC HPLC. As a control, the IFN-β prepared according to Example 14 was also processed using the same procedures and compared to untreated IFN-β prepared according to Example 14. For the biological characterization, IFN-β prepared according to Example 14, BETASERON, and rhIFN beta-1b isolated from each formulation were evaluated.

TABLE 9

Analytical Comparability Tests and Assessments

| Test | Assessment |
| --- | --- |
| Sequence and Identity Confirmation* | |
| N terminal sequence analysis | Equivalent to predicted sequence |
| Amino acid analysis | Amino acid content as predicted from sequence |
| Peptide mapping (reduced & non-reduced) | Comparable peptide map |
| Physicochemical Characterization* | |
| Molecular Weight/Mass | |
| MALDI-TOF | Comparable to theoretical molecular weight |
| SDS PAGE (reduced & non-reduced) | Comparable band patterns |
| Product Heterogeniety | |
| IEX LC | Comparable chromatograms |
| RP HPLC | |
| SEC HPLC (native & SDS) | |
| Structural Characterization | |
| UV-Vis absorption spectrum | Comparable absorption profiles |
| Analytical ultracentrifugation | Comparable sedimentation times and predicted molecular weight |
| Far and near UV circular dichroism | Comparable secondary and tertiary structure |
| Fluorescence | Comparable tertiary structure |

TABLE 9-continued

Analytical Comparability Tests and Assessments

| Test | Assessment |
|---|---|
| Biological Characterization | |
| Bioassay** | Comparable specific activity (MIU/mg) |
| Receptor binding (competition) | Comparable receptor binding |

*Analyses performed on rhIFN beta-1b isolated from BETASERON and IFN-β prepared according to Example 14 as well as untreated (stock) IFN-β prepared according to Example 14;
**Bioassay performed by PBL Biomedical Laboratories using A549 cells and EMC viral challenge.

N-terminal sequence and amino acid analyses demonstrated that the rhIFN beta-1b isolated from BETASERON and IFN-β prepared according to Example 14 were comparable and matched the predicted sequence. Peptide mapping analyses performed by Lys-C digest and RP HPLC indicated that the peptide maps were comparable for rhIFN beta-1b isolated from BETASERON and IFN-β prepared according to Example 14 as well as the control untreated IFN-β prepared according to Example 14. One peptide containing Asn25 in IFN-β prepared according to Example 14 was shifted to an earlier elution time consistent with deamidation. This result was expected because IFN-β prepared according to Example 14 was not purified using the last column step, S Sepharose, which was intended to remove deamidated rhIFN beta-1b.

The molecular weight by MALDI TOF analysis was 19,879 and 19,877 Da for rhIFN beta-1b isolated from BETASERON and IFN-β prepared according to Example 14, respectively. The mass accuracy of the MALDI-TOF instrument was calibrated to +/−2 AMU on the day of analysis. The band pattern for both reduced and non-reduced SDS PAGE gels was comparable for both products.

A comparison of the product heterogeneity for rhIFN beta-1b isolated from BETASERON and IFN-β prepared according to Example 14 as well as untreated IFN-β prepared according to Example 13 demonstrated comparability with the exception of the deamidated impurity present in rhIFN beta-1b in the IFN-β prepared according to Example 14. The SEC HPLC (native and SDS) analyses revealed comparable chromatographic profiles with predominantly monomeric rhIFN beta-1b (99.1% and 100% for sample from BETASERON and IFN-β prepared according to Example 14). Untreated IFN-β prepared according to Example 14 (research grade) was 99.3% monomeric rhIFN beta-1b by native SEC HPLC, indicating that the manufacturing process described above successfully produces drug substance essentially free of protein aggregates.

Structural characterization indicated that the rhIFN beta-1b in BETASERON and IFN-β prepared according to Example 14 as well as untreated IFN-β prepared according to Example 14 was comparable as measured by spectroscopic absorbance (200-400 nm), analytical ultracentrifugation, far ultraviolet circular dichroism, and fluorescence. Near ultraviolet circular dichroism was not performed due to the low rhIFN beta-1b concentrations of the samples. These results confirmed the comparability of the secondary and tertiary structure of rhIFN beta-1b in both products.

The biological activity of rhIFN beta-1b isolated from BETASERON and IFN-β prepared according to Example 14 was 28 MIU/mg and 55 MIU/mg, respectively. The biological activity of untreated IFN-β prepared according to Example 14 was 86 MIU/mg and untreated BETASERON was 62 MIU/mg. The CPE assay was performed against the WHO International Standard of IFN-beta, Gb23-902-531 (natural) using A549 cells and EMC viral challenge. The differences in potency were not considered significant because the research bioassay varies by over 50%. Overall, these results demonstrate that the rhIFN beta-1b isolated from BETASERON was comparable to rhIFN beta-1b in IFN-β prepared according to Example 14 as measured by physicochemical and biological assays.

EXAMPLE 16

This example describes preparation of IFN-beta-1b compositions from the initial expression steps from *E. coli*. to final composition formulation.

C17S IFN-beta-1b was expressed in *E. coli*. This protein has the following amino acid (AA) sequence according to SEQ ID No. 2:

Bar 25 Protein sequence:
(SEQ ID No. 2)
SYNLLGFLQRSSNFQSQKLLWQLNGRLEYCLKDRMNFDIPEEIKQLQQFQ

KEDAALTIYEMLQNIFAIFRQDSSSTGWNETIVENLLANVYHQINHLKTV

LEEKLEKEDFTRGKLMSSLHLKRYYGRILHYLKAKEYSHCAWTIVRVEIL

RNFYFINRLTGYLRN

The C17S IFN-beta-1b protein is encoded by the DNA sequence shown in uppercase according to SEQ ID No. 3:

Bar 25 Gene Sequence
(SEQ ID No. 3)
catATGAGCTACAACTTGCTTGGATTCCTACAAAGAAGCAGCAATTTTCA

GTCTCAGAAG

CTTCTGTGGCAATTGAATGGGAGGCTTGAATACTGCCTCAAGGACAGGAT

GAACTTTGACATCCCTGAGGAGATTAAGCAGCTGCAGCAGTTCCAGAAGG

AGGACGCCGCATTGACCATCTATGAGATGCTCCAGAACATCTTTGCTATT

TTCAGACAAGATTCATCTAGCACTGGCTGGAATGAGACTATTGTTGAGAA

CCTCCTGGCTAATGTCTATCATCAGATAAACCATCTGAAGACAGTCCTGG

AAGAAAAACTGGAGAAAGAAGATTTCACCAGGGGAAAACTCATGAGCAGT

CTGCACCTGAAAAGATATTATGGGAGGATTCTGCATTACCTGAAGGCCAA

GGAGTACAGTCACTGTGCCTGGACCATAGTCAGAGTGGAAATCCTAAGGA

ACTTTTACTTCATTAACAGACTTACAGGTTACCTCCGAAACTAAgaattc

The codon TCT for Ser-17 is underlined, as are recognition sites for NdeI (CATATG), HindIII (AAGCTT), and EcoRI (GAATTC).

Construction of C17S IFN-Beta Gene Sequence

The C17S (the abbreviation "C17S" indicates that the codon for cysteine at position 17 of the protein was changed to the codon for serine at position 17; when referring to the protein, it indicates that serine has been substituted for cysteine at the 17th position) protein sequence for IFN-beta (according to SEQ ID No. 2) was expressed in *E. coli*. as follows.

The gene for Interferon-beta (IFN-β) was isolated by PCR amplification of human genomic DNA (Cat. # 636401, Clontech, Calif.), using primers BARO 1 (5'CACGTGCATAT-GAGCTACAACTTGCTTGGATTC) (SEQ ID No. 4) and BARO 4 (5'CGGAATTCTTAGTTTCGGAGGTAACCTG-TAAG) (SEQ ID No. 5). The resulting fragment was digested with restriction enzymes NdeI (recognition sequence CATATG) and EcoRI (recognition sequence GAATTC), and cloned into similarly digested and calf intestine alkaline phosphatase (CIP)-treated pUC19. Several clones were isolated and sequenced, and one clone with the correct sequence was subjected to PCR-based mutagenesis using forward primer BARO 8 (5'AGCAGCAATTTTCAGTCTCA-GAAGCTTCTGTGGCAATTG) SEQ ID No. 6) and reverse primer BARO 9 (5'CAATTGCCACAGAAGCTTCT-GAGACTGAAAATTGCTGCT) (SEQ ID No. 7) as described in Higuchi R. (PCR Protocols; M.A. Innis et al., eds. 1990, Academic Press), which changed the codon TGT for Cysteine at position 17 (C17) to Serine (TCT, C17S). After mutagenesis, the gene was cloned into pUC19, and sequenced to confirm the presence of the C17S mutation. The final sequence of the IFN-β C17S gene was according to SEQ ID No. 3.

Construction of the Preliminary Expression Plasmid and Expression in recA+ Strains The IFN-β C17S gene was isolated as an NdeI-EcoRI fragment and cloned into similarly digested and CIP-treated pET21a+ (Novagen, WI). The vector pET21a+carries the phage T7 promoter and lac operator for regulated expression, and confers ampicillin resistance. The resulting plasmid was transformed into BL21 (DE3) and Rosetta2 (DE3), two strains that express the T7 RNA polymerase under the control to the lac promoter. The two strains are the same except for that Rosetta2 (DE3) contains the plasmid pRARE2 which expresses tRNAs for the rare *E. coli* codons AUA (Ile), AGG, AGA, CGG (Arg), CUA (Leu), CCC (Pro), and GGA (Gly), and confers chloramphenicol (Cam) resistance. Strain A [IFN-β C17S/pET21a+/BL21 (DE3)] and Strain B [IFN-β C17S/pET21a+/Rosetta (DE3)] were grown at 37° C. in LB medium containing the appropriate antibiotics (Strain A, ampicillin; Strain B, ampicillin+chloramphenicol) to an optical density at 600 nm (OD-600) of 0.5. Expression of IFN-β C17S was induced by addition of 0.75 mM isopropyl-beta-D-thiogalactopyranoside (IPTG). Samples were taken for analysis by SDS-PAGE shortly before induction, and one, two, three and four hours after induction. We found that Strain A expressed no observable IFN-β C17S whereas Stain B expressed ~20% of total cell protein at two and three hours after induction.

Construction of the Final Expression Plasmid

The IFN-β C17S gene was then transferred to pET24a+, a T7 promoter vector that carries the kanamycin resistance gene. This plasmid was termed pBAR12, starting with human genomic DNA. pBar12 was used to transform BL21 (DE3) and Rosetta2 (DE3), and the resulting strains, Strain C and Bar23, were subjected to growth (with LB medium containing the appropriate antibiotics), IPTG induction and expression analysis as described above. We found that Strain C expressed no detectable IFN-β C17S whereas Bar23 expressed between 10% and 15% of total cell protein. We assume that both Strain B (above) and Bar23 express IFN-β C17S because these strains contain pRARE2, which carries tRNA genes for rare *E. coli* codons. Such codons are present in the IFN-β C17S gene.

Development of the Final Expression Strain

Strains BLR (DE3) and HMS 174 (DE3) (Novagen) were transformed with pRARE2 to produce strains D and E. These strains, in addition to containing the pRARE2 plasmid, are recA−. Strains D and E were transformed with pBAR12 to give Bar24 and Bar25, respectively, which were evaluated for IFN-β C17S expression as described above, except that the 4 hour time point after induction was eliminated. These strains produced substantial levels of IFN-β C17S, with the HMS 174-based strain (a K12 strain) expressing approximately twice as much of the protein as the BLR-based (B) strain. This result and the data from additional experiments comparing the two strains using other media (not shown) led us to choose Bar 25 as the final IFN-β strain, which was designated as the Bar 25 protein herein. We then confirmed the sequence of the IFN-β C17S gene in Bar25 using the T7 primer (5'TAATAC-GACTCACTATAGGG) SEQ ID No. 8) and the T7 terminator primer (5'GCTAGTTATTGCTCAGCGG) (SEQ ID No. 9).

The overall manufacture of the Bar 25 protein was performed in three stages: fermentation, primary recovery and secondary recovery. A detailed overview of the process including the operating parameters is provided in FIGS. 21A and 21B and 22A, 22B and 22C. This process yields final formulated bulk drug substance.

Fermentation

The manufacturing process was initiated with thawing of two vials of the working cell bank (WCB) followed by shake flask incubation (one 450 mL flask per WCB vial). The shake flasks were incubated for 9 hr at 37° C. to achieve an $OD_{600}$ (optical density at 600 nm) in excess of 0.5. The purity of the cultures was confirmed prior to use for inoculation of the fermentor. Only one flask was used for inoculation of the fermentor.

The fermentation was conducted in a 100 L fermentor with 4% yeast extract, 0.1 M 2-(N-morpholino)ethanesulfonic acid (MES), pH 6.5, 1% NaCl with 4% glycerol, 25 µg/mL kanamycin, and 34 µg/mL chloramphenicol. The temperature was controlled at 37±1° C. and the airflow rate was controlled to 100±2 L/min. The agitation speed was adjusted between 200 and 700 rpm to maintain the $pO_2$ (partial oxygen pressure) level at 40±5%. The pH was maintained at pH 6.5±0.2. Cell growth was monitored until an $OD_{600}$ of 25±5 was achieved and then rhIFN beta-1b expression was induced with isopropyl β-D-1-thiogalactopyranoside (IPTG) to a final concentration of 0.75 mM. The induction phase was allowed to continue for 3 hrs and then the fermentation was stopped.

The fermentation involved 9.1 hr of cell growth followed by 3 hr of induction. This fermentation resulted in a titer of 2.0 g/L of rhIFN beta-1b upon harvest of the fermentor. Continuous expression was observed as expected during the induction phase resulting in rhIFN beta-1b levels at 50.5% of the total cell protein. The similar fermentation in Example 17 below yielded similar results (2.0 g/L rhIFN beta-1b and 41.4% of total cell protein).

Inclusion Body Isolation

After completion of the fermentation, cells were harvested, centrifuged, resuspended, and homogenized to isolate the inclusion bodies (IB). See Table 10. IBs were recovered by centrifugation and washed prior to further processing.

The fermentation broth for the 100 L fermentation was 96 L and contained 195.4 g of rhIFN beta-1b as measured by quantitative SDS-PAGE (sodium dodecyl sulfate polyacrylamide gel electrophoresis) analysis. After centrifugation and resuspension of the cell paste, 81.4 L of resuspended cell paste containing 183.2 g of rhIFN beta-1b was recovered. Isolation of the IB by homogenization, centrifugation and washing yielded 170.1 g of rhIFN beta-1b for further processing. The recovery of IBs by centrifugation post homogenization was comparable to Example 17 below, manufacture with an IB weight of 179.6 g of rhIFN beta-1b.

TABLE 10

Operating conditions of harvesting, homogenization, IB recovery, solubilization and clarification steps

| Step | Operation | Operating parameters |
|---|---|---|
| Cell paste harvesting | Centrifugation | 8000 rpm (16,000 g) for 15 min |
| Cell paste Resuspension | Addition of buffer A and resuspension of cell paste | 20 mL buffer A per g of fermentation wet cell paste |
| Homogenization | Homogenization of resuspended cell paste using a homogenizer. | 2 passes at 800 bars; Homogenate cooled below 20° C. prior to each pass |
| Homogenate centrifugation | Centrifugation | 8000 rpm (16,000 g) for 30 min |
| IB pellet washing | Resuspension of IB pellet and in purified water | 40 mL purified water per g of fermentation wet cell paste |
| IB pellet centrifugation | Centrifugation | 8000 rpm (16,000 g) for 30 min. Storage of IB at RT. |

Inclusion Body Solubilization and Extraction

After isolation of the IBs, solubilization, solvent extraction and precipitation steps were performed to increase the purity of the rhIFN beta-1b. This stage was performed in 6 sub-batches to minimize solvent volumes. The IB suspension was solubilized in 2% sodium dodecylsulfate (SDS), 20 mM 2-Amino-2-hydroxymethyl-propane-1,3-diol (Tris), 2 mM ethylenediaminetetraacetic acid (EDTA), 10 mM dithiolthreitol (DTT), pH 8.0 (buffer B). The solubilized IBs were then extracted with sec-butanol. Phase separation of the aqueous and organic layers was facilitated by centrifugation. After removal of the aqueous layer, methanol was added to the sec-butanol solution to precipitate the rhIFN beta-1b. The methanol precipitate was concentrated by centrifugation and resuspended in water. The suspension was homogenized to yield fine particulates for the subsequent refolding step.

Approximately 260±5 g of washed inclusion bodies were solubilized in 6.0 L of buffer B for each sub-batch, with the exception of sub-batch 6, where only 192 g of IB available, remained. 12.0 L of sec-butanol was subsequently added to 6.0 L of solubilized IBs with vigorous mixing at room temperature for 10 minutes. The sec-butanol solution was centrifuged for 10 minutes at 5100 rpm, 4° C. with the organic phase containing rhIFN beta-1b. A volume of methanol equal to twice the volume of the organic phase (~37±1 L) was then added with incubation at room temperature for a target of 3 hours with vigorous mixing every 30 minutes. The methanol/sec-butanol organic phase solution was centrifuged for 10 minutes at 5100 rpm, 4° C. The amount of rhIFN beta-1b precipitate pellet (106.5-137.7 g) obtained for each sub-batch was consistent with the amount obtained in Example 17, below. The pellet containing rhIFN beta-1b was resuspended in 6.0 L of purified water and stored at 2°-10° C. until completion of the last solvent extraction sub-batch. SDS-PAGE analysis of the extraction and precipitation process indicated that a significant proportion of the host cell proteins present in the solubilized IB were removed.

Figure 22A:
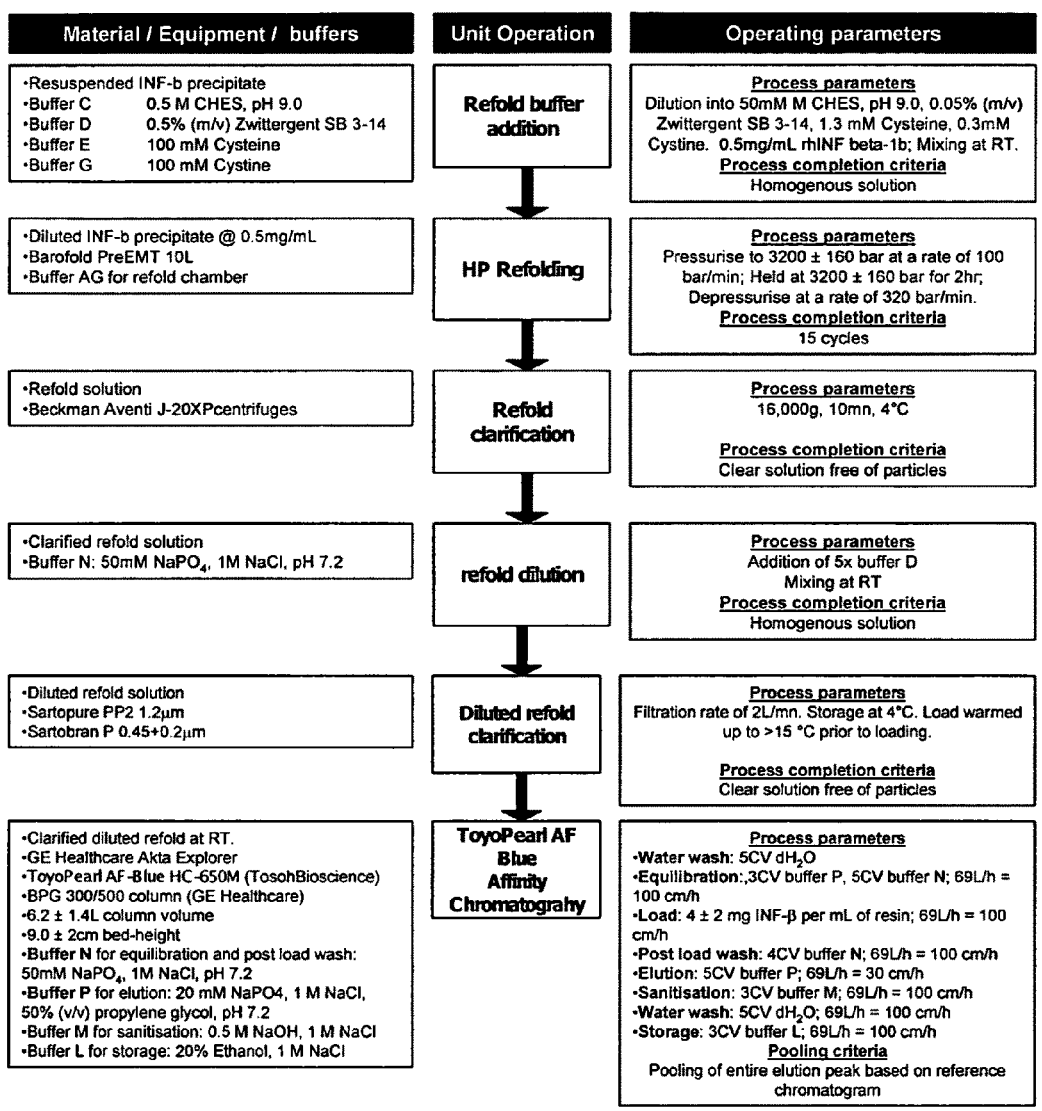
FIG. 22A is a schematic diagram of a secondary recovery process.

High pressure refolding was performed by filling an 8.2 L biocompatible bag (Hyclone Part # SH3B5023.01.02), which was manufactured with the same materials used for cGMP (current good manufacturing practices) storage of biologics, with the protein suspension and refolding buffers (buffers C, D, E and G listed in FIG. 22A; and Table 11). The sealed bag was placed inside the 10 L PreEMT vessel and the remaining space in the vessel was filled with 50 mM 2-(N-Cyclohexylamino)ethane Sulfonic Acid (CHES) buffer, pH 9.0, to remove air from the system. No product contact was made with the buffer or the vessel walls, and dye leak studies have been performed to ensure the bag integrity was maintained during the process. The vessel pressure was ramped up to 3200±160 bar and held for 2 hr. The pressure was then returned to ambient conditions and the solution was removed from the bag. The refolded solution was centrifuged to remove remaining insoluble particulate, diluted, and filtered through a 1.2 μm filter followed by a 0.2 μm filter.

TABLE 11

Operating conditions of high pressure refolding, clarification and dilution

Figure 5:
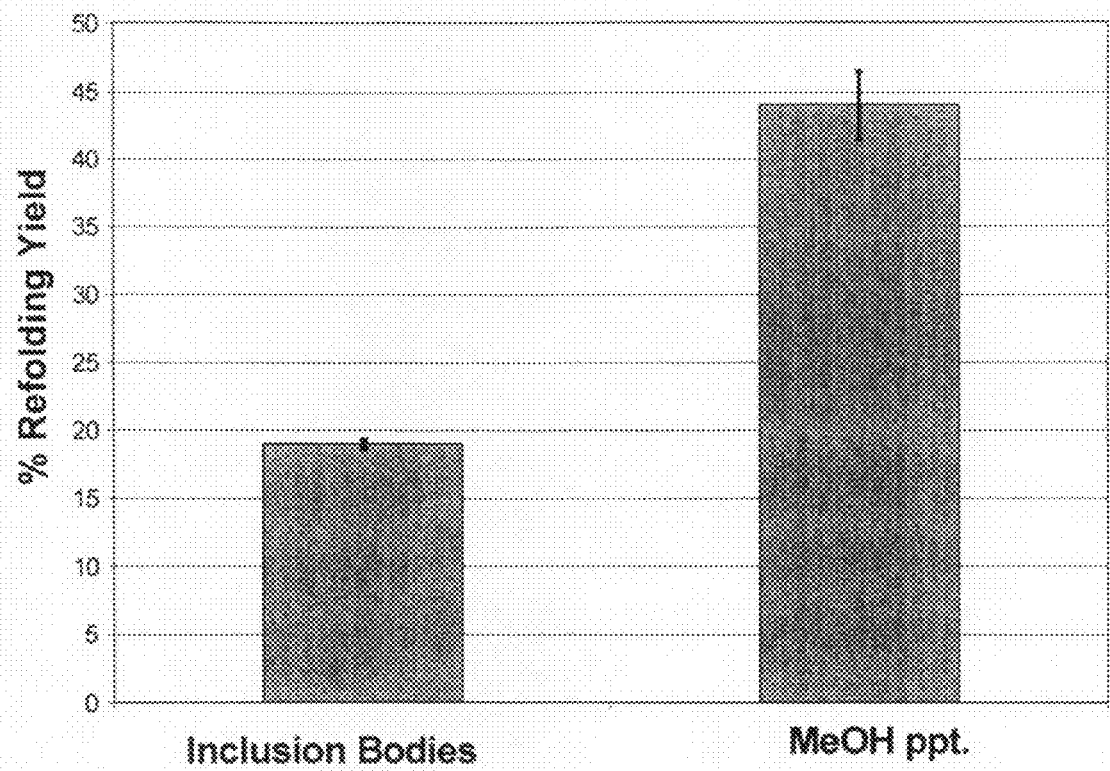
FIG. 5 is a chart showing a comparison of refolding yield of IFN-beta precipitated from butanol extracts using methanol against yields of IFN-beta refolded from inclusion bodies under "best-case" refolding conditions.

| Step | Operation | Operating parameters |
|---|---|---|
| Refold preparation | Addition of buffers C, D, E and G to rhIFN beta-1b precipitate | Refer to FIG. 5 for refold solution composition |
| High pressure refold | Refolding of rhIFN beta-1b under high pressure in preEMT vessel | Hold pressure: 3200 ± 160 bar Hold time: 2 h Pressure ramp up rate: 100 bar/min Pressure ramp down rate: 320 bar/min |
| Clarification | Centrifugation of refold solution | 8000 rpm (16,000 g) for 10 min |
| Dilution | Addition of clarified refold to buffer N | Addition of five consecutive clarified refold sub-batches to 160 L of buffer N. Storage at RT. |
| Filtration | Filtration of diluted refold from Separation Suite to Purification suite | 1.2 μm filter followed by 0.2 μm filter. Storage of filtered diluted refold at <10° C. and equilibration to >15° C. prior to blue affinity chromatography. |

High Pressure Refolding

High pressure refolding was performed in 15 sub-batches. Post refold cycle, the solution was centrifuged for 10 minutes at 8000 rpm, 4° C. The supernatant was added to 160 L of buffer N (FIG. 22) in preparation of loading onto the blue affinity column. Refold sub-batches 1-5, 6-10 and 11-15 were conditioned to generate blue affinity loads 1, 2 and 3 respectively, as described below. A total of approximately 600 L of diluted refold (i.e. blue affinity load) was generated and subsequently filtered in an ISO7 cGMP area. The conditioned blue affinity load was stored at 2-8° C. with equilibration to 15°-25° C. prior to blue affinity chromatography commencement.

Blue Affinity Chromatography Step

The Toyopearl AF-blue HC 650M affinity chromatography stage was performed using a 6 mm Bioprocess Rig in combination with Unicorn software (GE Healthcare Biosciences). The column was packed, checked for Height Equivalent to the Theoretical Plates (HETP), sanitized and washed with water. The column was equilibrated with buffer P followed by buffer N (FIG. 22). 4±2 mg rhIFN beta-1b per mL of resin was loaded onto the column followed by a wash with buffer N and a step elution with buffer P. Fractions were collected across the elution peak, analyzed, and pooled prior to further processing.

Approximately 600 L of conditioned blue affinity load (Temperature>15° C., and average pH of 7.5 and conductivity of 57.9 mS/cm) was loaded on the column. The product eluted as a single peak. Fractions 3 through 12 were collected across the peak and pooled. SDS-PAGE analysis indicated that no detectable amount of rhIFN beta-1b was present in the column flow through and post load wash and that rhIFN beta-1b eluted in fractions 3 to 12. The pooled fractions yielded a 10 L solution of 0.40 mg/mL rhIFN beta-1b. The pooled fractions were filtered using a 1.2 μm filter. An overall yield of 4.0 grams was determined by $A_{280}$ quantification of the pooled fractions. (UV spectroscopy at 280 nm using the absorbency value of 1.493 as the extinction coefficient for a 0.1% (1 mg/mL) solution) The filtered, pooled fractions were diluted with 4× volume of buffer T (FIG. 22B) and stored at 2°-10° C. prior to the Immobilized Metal Affinity Chromatography (IMAC) step.

The IMAC stage was performed using a 6 mm Bioprocess Rig in combination with Unicorn software (GE Healthcare Biosciences). The IMAC column was packed with GE Healthcare Biosciences IMAC Sepharose Fast Flow resin, checked for HETP, and washed with water. The column was charged with 10 mM copper sulfate, washed with water, and equilibrated with buffer T (FIG. 22B). 2.5±1.5 mg rhIFN beta-1b per mL of resin was loaded onto the column and an uncharged IMAC trap column was placed in-line to capture copper leached from the IMAC capture column. The rhIFN beta-1b was eluted with a gradient from 10 to 75% buffer U containing 50 mM imidazole (90 to 25% buffer T). rhIFN beta-1b has unique properties that causes it to bind to the IMAC column. An imidazole gradient enables separation of deamidated and non-deamidated rhIFN beta-1b. Fractions were collected across the elution peak. The extent of deamidation decreases across the gradient. The initial peak fractions were analyzed by analytical cation exchange chromatography (CIEX HPLC). The fractions containing >55% non-deamidated rhIFN beta-1b as measured by the CIEX HPLC were pooled for further processing.

Approximately 50.0 L of conditioned blue affinity pooled fractions 3 to 12 (pH of 7.1 and conductivity of 17.0 mS/cm) were loaded onto the IMAC column. The IMAC performed as expected with a sharp absorbance peak followed by the rhIFN beta-1b peak observed early in the elution gradient. SDS-PAGE analysis indicated that no detectable amount of rhIFN beta-1b was eluted during post elution wash and sanitization steps. The main peak eluted over approximately 8 column volumes and fractions were collected across the peak for CIEX HPLC and protein content (absorbance at 280 nm; A280) analyses. As shown in Table 12, initial fractions up through and including fraction 8 did not meet the in-process criteria for >55% non-deamidated rhIFN beta-1b. The fractions 9 through 23 were pooled yielding 2.4 grams rhIFN beta-1b as determined by A280, which corresponded to a 60% recovery of the total protein measured by A280 analysis of the Toyopearl AF-Blue affinity pooled fractions. The pooled fractions (15 L) were diluted 10 fold with buffer W, resulting in 150 L of diluted pooled fractions, and stored at 2-10° C. prior to the next process step, cation exchange chromatography.

TABLE 12

CIEX-HPLC analysis of IMAC elution fractions

| Elution fraction number | CIEX-HPLC main peak purity (%)* |
|---|---|
| Fraction 6 | 43.3 |
| Fraction 7 | 44.6 |
| Fraction 8 | 50.8 |
| Fraction 9 | 59.0 |
| Fraction 10 | 62.8 |
| Fraction 11 | 66.5 |
| Fraction 12 | 69.1 |
| Fraction 13 | 71.1 |
| Fraction 14 | 72.6 |
| Fraction 15 | 74.5 |

*Pooling criteria for IMAC: fractions that describe the start of the main peak were to be sampled and tested by CIEX-HPLC analysis. Fractions at the front of the main peak with purity below 55% were excluded.

CIEX (SP-Sepharose) Column Step

Figure 22B:
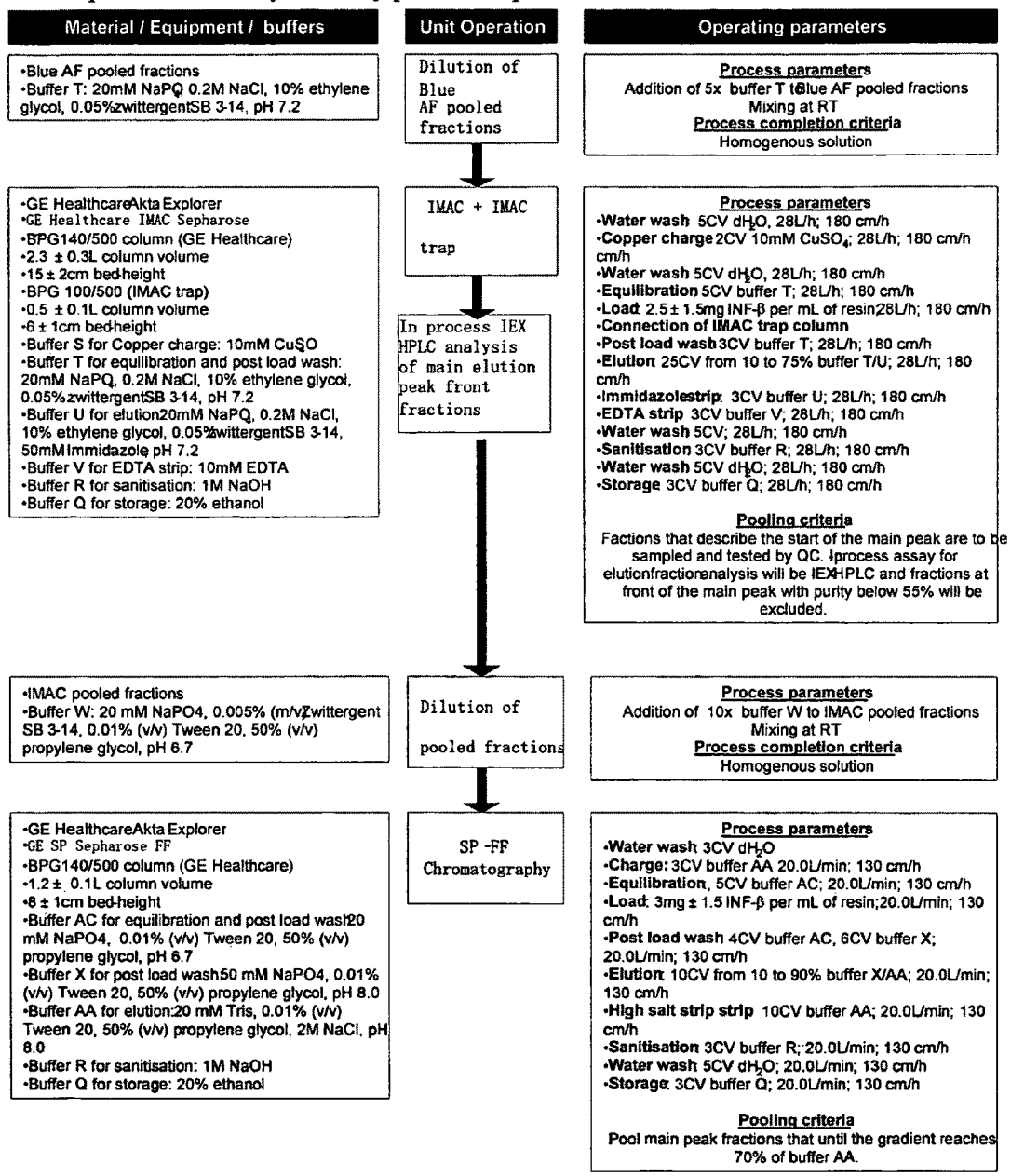
FIG. 22B is a continuation of the schematic diagram of the secondary recovery process of FIG. 22A.

The cation exchange chromatography step was performed using a 6 mm Bioprocess Rig in combination with Unicorn software (GE Healthcare Biosciences). The primary purpose of this step was the replacement of the surfactant, Zwittergent 3-14 (n-tetradecyl-N,N-dimethyl-3-ammonio-1-propanesulfonate), with 0.01% polysorbate 20 (Tween 20), which was desirable in the final formulation to inhibit protein aggregation. The column was packed (GE Healthcare Biosciences SP (Sulfopropyl)-Sepharose Fast Flow resin), checked for HETP, sanitized and washed with purified water. The column was charged with the elution buffer (buffer AA; FIG. 22B) containing 2 M NaCl. Equilibration of the column was performed with buffer AC (no NaCl) and a protein load of 3±1.5 mg of rhIFN beta-1b per mL of resin was applied to the column. After loading, the column was washed with buffer X (pH 8.0) and then eluted with a gradient from 10 to 90% buffer AA. Main peak fractions were collected until the gradient reached 70% buffer AA and fractions were pooled prior to further processing. The pooling criteria were selected to minimize exposure of the protein to high salt concentrations that may cause aggregation.

Approximately 150.0 L of conditioned IMAC pooled fractions 3 to 12 (pH of 6.6 and conductivity of 1.0 mS/cm) was loaded onto the column. The CIEX chromatography performed as expected with a sharp absorbance peak eluting at the beginning of the sodium chloride gradient. SDS-PAGE analysis indicated that no detectable amount of rhIFN beta-1b was present in the column flow through and post load wash and that rhIFN beta-1b eluted in fractions 2 through 10. No detectable rhIFN beta-1b was present in the post load wash and column sanitization samples. An increase in pH from 6.5 to 8.0 occurred during the second post load washing step, as a result of the application of buffer X (50 mM NaPO4, 0.01% (v/v) Tween 20, 50% (v/v) propylene glycol, pH 8.0) onto the column. The pH increase was associated with a small increase in absorbance. The elution gradient reached 70% of buffer AA after 0.4 L was collected in elution fraction 10, and subsequent fractions were not included in the pool. A 65% recovery of the total protein as measured by A280 analyses of the IMAC pooled fractions and CIEX pooled fractions was obtained.

The CIEX pooled fractions (pH of 7.5 and conductivity of 10.4 mS/cm) were subsequently diluted with buffer AD to reduce the salt concentration and then buffer AE to reduce the pH. rhIFN beta-1b was more stable at low pH (3-4) and low salt (<100 mM) than at high pH (6-8) and high salt. SEC-HPLC analysis of the pooled fractions pre and post dilution indicated an absence of rhIFN beta-1b aggregate in all samples. An overall yield of 1.65 grams was determined by A280 quantification of the diluted CIEX pooled fractions, which compared favorably to the yield of 1.72 g and 1.67 g determined by RP-HPLC and SEC-HPLC respectively. The diluted CIEX pooled fractions were stored at 20-10° C. prior to diafiltration.

In Example 17 below, the diluted CIEX pooled fractions were held for approximately 2.5 days at <10° C. prior to further processing. After this storage, the rhIFN beta-1b was observed to contain about 4 weight percent protein aggregates. Development studies determined that a maximum hold time of 8 hr prior to diafiltration is desirable to reduce the risk of undue aggregation of the rhIFN beta-1b. Accordingly, the diluted material of this example was stored at 2-10° C. for less than 8 hr prior to the next step, diafiltration. The dilution buffers SD and AE were also cooled in this example to <10° C. prior to dilution of the CIEX pooled fractions to minimize potential aggregation during storage.

Figure 22C:
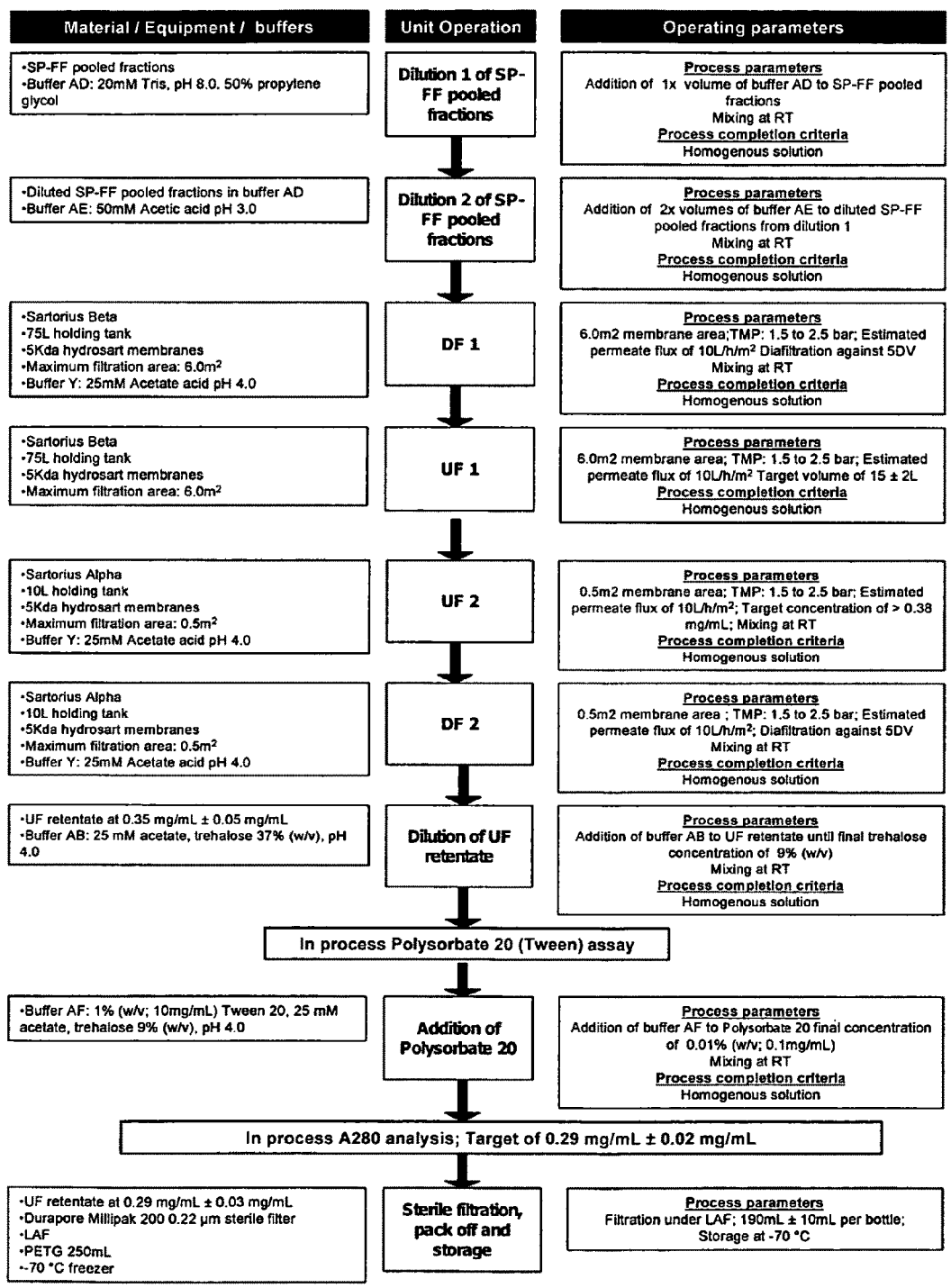
FIG. 22C is a continuation of the schematic diagram of the secondary recovery process of FIG. 22B.
Figure 23:
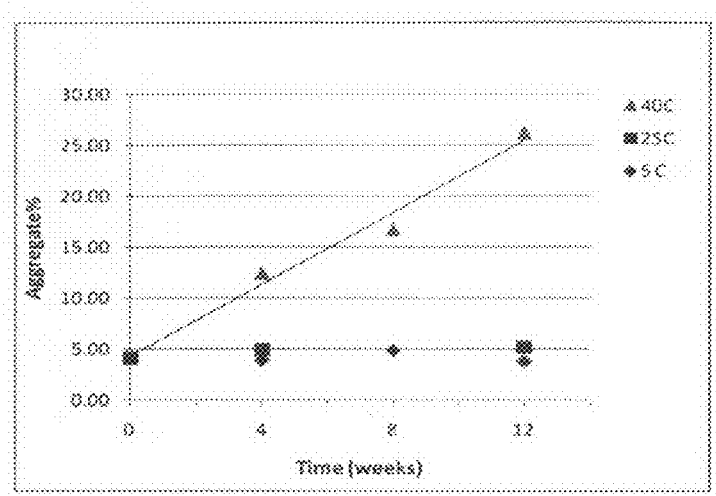
FIG. 23 is a chart showing the rate of aggregation of an IFN sample as a function of time.
Figure 24:
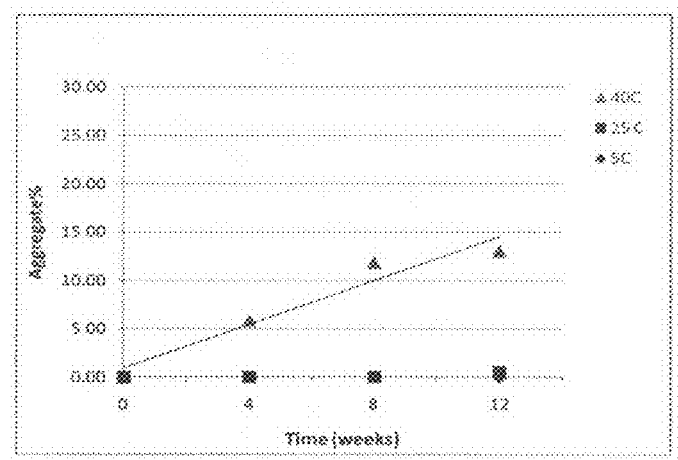
FIG. 24 is a chart showing the rate of aggregation of another IFN sample as a function of time.

The diluted CIEX pooled fractions were diafiltered (DF) with 5 diavolumes of buffer Y (25 mM sodium acetate, pH 4.0) and then concentrated by ultrafiltration (UF) to achieve a target concentration of greater than 0.38 mg/mL rhIFN beta-1b (FIG. 22C). The concentrated solution was further diafiltered with 5 diavolumes of buffer Y. The resulting solution was concentrated by ultrafiltration to a target of 0.35±0.05 mg/mL. A concentrated stock solution containing 37% w/v trehalose (buffer AB) was added to yield a final trehalose concentration of 9% w/v. The solution was analyzed for Tween 20 content and the appropriate amount of a concentrated Tween 20 (1% w/v) stock solution (buffer AF) was added to yield a final Tween 20 concentration of 0.01% w/v. The unfiltered bulk drug substance composition has a target rhIFN beta-1b concentration of 0.29±0.03 mg/mL in a formulation of 25 mM sodium acetate, pH 4.0, 9% w/v trehalose, 0.01% Tween 20. Sterile filtration was performed through two 0.22 μm filter cartridges in series in a laminar air flow (LAF) environment. The filtered bulk drug substance was filled at 190±10 mL into 250 mL Polyethylene Terephthalate Glycol (PETG) bottles under LAF and frozen at −70° C.

The diluted CIEX pooled fractions were diafiltered against buffer Y and concentrated prior to formulation by addition of buffers AE and AF. Throughout the UF/DF steps, there was negligible transmission of rhIFN beta-1b through the 5 kDa cut-off membranes, as assessed by the consistency in rhIFN beta-1b yield throughout the process (approximately 1.6 to 1.7 g) and low absorbance of UF/DF permeate (typically <0.01 absorbance units). After the second diafiltration, the protein solution was concentrated to 0.39 mg/mL rhIFN beta-1b. The concentration decreased to 0.36 mg/mL rhIFN beta-1b after addition of the UF/DF flush and was 0.28 mg/mL rhIFN beta-1b following addition of buffer AB to a trehalose final concentration of 9% w/v. In-process Tween 20 analysis reported a concentration of 0.04% w/v. This value was identical to the concentration of 0.04% w/v measured at the same stage for Example 18. Subsequently, 33 mL of buffer AF was added to the bulk drug substance.

Within a laminar flow cabinet, the bulk drug substance was filtered through two 0.22 μm sterile filters assembled in series and subsequently dispensed into sterile 250 mL PETG bottles. Approximately 6.3 L of bulk drug substance was dispensed which corresponded to 1.47 g of rhIFN beta-1b based on a rhIFN beta-1b concentration of 0.23 mg/mL post filtration.

EXAMPLE 17

The procedure of Example 16 was used to prepare rhIFN beta-1b except that a holding time was incorporated into the procedure prior to the diafiltration. Specifically, after the SP-Sepharose column chromatography and subsequent dilution, the diluted, pooled fractions were held for about 2.5 days at less than about 10° C. prior to diafiltration processing. With this holding time, the resultant rhIFN beta-1b would have an aggregate content of about 4 weight percent. In contrast, as reported in Example 16, when this holding time is minimized or avoided, the resultant product is essentially aggregate free, having an aggregate content of less than about 0.5 weight percent.

EXAMPLE 18

Fermentation

Fermentation of *E. coli* for the production of IFN-beta-1b was conducted in a 100 L fermentor, operating at 37° C., using growth media containing 4% yeast extract, 0.1M MES (pH 6.5), 1% NaCl and 4% glycerol. The fermentation was conducted for 9 hours until an $OD_{600}$ of 20.5 was obtained. At this time, the fermentation was induced using IPG and fermented for an additional four hours. 2 g/L expression of IFN-beta-1b in the form of inclusion bodies was obtained. The cells were centrifuged using a Beckman Aventi centrifuge operated at 16,000×g. Inclusion bodies were obtained by cell lysis using a Niro Soavi Pony, operated at 800 bar and passed two times and pelleted via centrifugation as described above.

Inclusion Body Extraction into Butanol 20 mls of solubilization buffer (2% SDS, 20 mM Tris, pH 8.0, 2 mM EDTA, 10 mM DTT) per gram of inclusion bodies was used to solubilize the resulting inclusion bodies obtained. This ratio resulted in sub-batches of 260+/−5 g of inclusion bodies added to 6 L of solubilization buffer. The mixture was stirred for 30 min at room temperature. 12 L of sec-butanol were added to 6 L of solubilized inclusion bodies and vigorously mixed for ten minutes. The methanol/sec-butanol organic phase solution was centrifuged for 10 minutes at 5100 rpm, 4° C. The pellet containing rhIFN beta-1b was re-suspended in 6.0 L of purified water using a hand held ultraturrax and stored at less than 10° C. until completion of the last solvent extraction sub-batch. SDS-PAGE analysis of the extraction and precipitation process indicated that a significant proportion of the host cell proteins present in the solubilized IB were removed High Pressure Refolding The rhIFN beta-1b material was subjected to high pressure refolding using procedures similar to those of Example 17 under refolding conditions of 3200 bar, 50 mM CHES (pH 9.0), 1.3 mM cysteine, 0.3 mM cystine, 0.05% Zwittergent 3-14 surfactant for 2 hours at 25° C. Depressurization was conducted at a rate of 320 bar minute. After refolding, the samples were centrifuged prior to purification.

Blue-Sepharose Purification

Toyopearl AF-Blue HC-650M blue affinity resin was used for purification of IFN-beta. For this column, "Equilibration buffer" containing 50 mM sodium phosphate pH 7.2 and 1 M NaCl was used, with an "Elution buffer" containing 20 mM sodium phosphate pH 7.2, 1 M NaCl, 50% propylene glycol.

The column was equilibrated by washing (at room temperature) a 50 mL Toyo blue column (Part # 19689) with 3 column volumes (CV) of distilled water, followed by 3 CVs of elution buffer, and 3 CVs of equilibration buffer. The volume of the column is a function of the scale of the process. The column was loaded by diluting the clarified refold 5× in equilibration buffer and loaded onto the column at a flowrate of 5 ml/min. The column was washed after loading with 3 CV of equilibration buffer. 3-5 mg IFN-beta were loaded per mL resin. For column elution, the column was washed with 1 CV of elution buffer at rate of 5 ml/min, followed by 3 CVs of 25% elution buffer (with the remainder equilibration buffer), followed by 6 CVs of 100% elution buffer. Fractions containing purified rhIFN beta-1b were pooled and stored at 4° C.

Cu-IMAC Purification

A copper IMAC column (Ge Healthcare Biosciences IMAC Sepharose Fast Flow) was used to remove endotoxin, and *E. coli* contaminant proteins. An "Equilibration Buffer" containing 20 mM sodium phosphate pH 7.2, 0.2 M NaCl, 10% Propylene Glycol, and 0.05% Zwittergent SB 3-14 surfactant. An 'Elution buffer" containing the equilibration buffer with the addition of 50 mM imidizole was also used. Two columns (5 ml and 1 ml) were used in series to minimize copper contamination.

For column loading, the blue pool (column #1) was diluted 5× in equilibration buffer and loaded onto the columns at a flowrate of 1 ml/min. The column was washed after loading with 2 CVs of equilibration buffer and 2-3 mg IFN beta was loaded per mL of resin. For column elution, at a flow rate of 1 mL/min, the column was washed with 1 CV of equilibration buffer, followed by 25 CV linear gradient from 0-60% Elution buffer, with the remainder being equilibration buffer, followed by 3 CVs of 100% elution buffer. Fractions containing purified IFN beta and no visible ECPs or aggregates (based on SDS-PAGE and sizing) were pooled and stored at −20° C.

S-Sepharose Purification

A GE Healthcare Biosciences SP-Sepharose Fast Flow was used to further purify IFN-beta and remove Zwittergent 3-14 surfactant from the process. An "Equilibration Buffer A" containing 20 mM sodium phosphate (pH 6.7), 50% propylene glycol, and 0.01 or 0.05% Tween-20 was used as well as "Equilibration Buffer B" which contains the same reagents at a pH of 8.0. An 'Elution buffer" containing 20 mM Tris (pH 8.0), 50% propylene glycol, 0.01% or 0.05% Tween 20, 2M NaCl, pH 8.0 was generated.

The column was then equilibrated with 3 CVs of equilibration buffer A. For column loading, the Cu pool (column #2) was diluted 10× into dilution buffer and loaded onto the columns at a flowrate of 1 ml/min. The column was washed after loading with 4 CVs of Equilibration buffer A, followed by 6 CVs of Equilibration buffer B. For column elution, at a flow rate of 1 mL/min, the column was washed with a step elution of Elution buffer.

Tangential Flow Filtration (TFF) into Formulation Buffer

The SP-FF pool was diluted prior to TFF using a two-step method. First, the pool was added to an equal volume of cold 20 mM Tris pH 8.0, 50% Propylene Glycol and mixed gently by inversion. It was then quickly added to 2 volumes of cold 50 mM Sodium Acetate pH 4.0 (6×total dilution of starting material) and mixed gently by inversion. Buffer exchange of the diluted S-FF pool was performed by TFF after stored at 5° C. for 16 hours using 6 dia-volumes of 25 mM Sodium Acetate pH 4. Trehalose was added to 9% and the rhIFN-beta-1b was sterilized filtered using a 0.22 μM PVDF sterile filter. Tween-20 was added to a final concentration of 0.01%. The resultant preparation comprising the rhIFN-beta-1b was stored in plastic PETG bottles at −70° C. This rhIFN-beta-1b shall be referred to herein as Sample 19A and had an aggregate content of about 4 weight percent. It is believed that aggregation resulted during the course of the 16 hour holding time between the dilution following S-Sepharose purification and the diafiltration.

This example describes a purification scheme by which Sample 19A was purified to yield a substantially aggregate free rhIFN beta-1b that is substantially 100% monomeric with essentially no aggregates (less than about 0.5 weight percent aggregate content). The resultant aggregate free rhIFN beta-1b produced in this example as described below is referred to herein as Sample 19B.

The Sample 19A material to be purified in this example was formulated in 25 mM sodium acetate, ph 4, 9% trehalose, and 0.01% by weight polysorbate 20. As an overview, a purification process for removing the aggregate content of Sample 19A includes two chromatography column steps: a 5 mL HiTrap IMAC-HP (High Performance) column charged with 2.5 column volumes of 10 mM $CuSO_4$ and a 5 ml HiTrap SP-FF column.

Sample 19A was diluted five fold with the equilibration buffer A (50 mM sodium phosphate pH 7.2, 0.05% Zwittergent 3-14 surfactant, 10% Ethylene Glycol, 0.2M NaCl) and loaded onto the pre-charged, pre-equilibrated IMAC-HP column. A 1 mL-uncharged IMAC-HP column was attached to the column outlet. The protein was eluted with buffer B (20 mM sodium phosphate pH 7.2, 0.05% Zwittergent SB 3-14 surfactant, 10% Ethylene Glycol, 0.2M NaCl, 50 mM Imidazole) using a 0-75% B gradient over 25 column volumes. The elution took place with a non-charged 1 mL IMAC trap column attached in place during elution to trap any copper leached from the IMAC-HP column. Fractions containing rhIFN beta-1b were pooled.

The pooled fractions from the IMAC-HP column elution were further purified using a 5 mL HiTrap SP-FF for removal of Zwittergent SB 3-14 surfactant and imidazole. The protein pool was diluted ten fold with the equilibration buffer (20 mM $NaPO_4$ pH 6.7, 0.01% Tween-20, 50% Propylene Glycol, 0.005% Zwittergent SB 3-14 surfactant) and then loaded onto the column. The column was washed with 5 column volumes of the equilibration buffer prior to elution using a 0-100% buffer B (20 mM sodium phosphate, pH 8.0, 0.01% Tween-20, 50% Propylene Glycol, 2M NaCl) gradient over 15 column volumes. A majority of the fractions containing rhIFN beta-1b were pooled. Later eluting fractions that contained high sodium chloride levels were excluded.

The SP-FF pool was diluted prior to tangential flow filtration (TFF) using a two-step method. First, the pooled fractions were added to an equal volume of cold 20 mM Tris pH 8.0, 50% Propylene Glycol and mixed gently by inversion. Then, the diluted pool was quickly added to 2 volumes of cold 50 mM Sodium Acetate pH 4.0 (6×total dilution of starting material) and mixed gently by inversion.

Buffer exchange of the diluted S-FF pool was performed by TFF using 6 diavolumes of 25 mM Sodium Acetate pH 4. Trehalose was added to 9% w/v prior to filter-sterilization of the protein pool. Tween-20 was added to a final concentration of 0.01% v/v.

Prior to being loaded into vials, rhIFN beta-1b was diluted to 0.12 mg/ml using formulation buffer (25 mM Sodium Acetate, pH 4.0, 9% Trehalose, 0.01% Tween-20) and filter-sterilized using a 0.22 μm Polyvinylidene Fluoride (PVDF) filter, prior to filling of vials. Vials were filled aseptically in a laminar flow hood.

The FIGS. 23-28 summarize results from various HPLC assays. More specifically, the data shown in FIGS. 23 and 24 indicate that both Samples were stable (no significant increase of aggregates) for up to 12 weeks at both 5° C. and 25° C. Aggregation was observed in the samples that were stored at 40° C. No significant fragmentation was detected after 12 weeks. The rate of aggregate formation for the Sample 19A material was greater than that aggregate-free Sample 19B material. This suggests that the presence of aggregates initially may act to promote the formation of aggregates.

Figure 25:
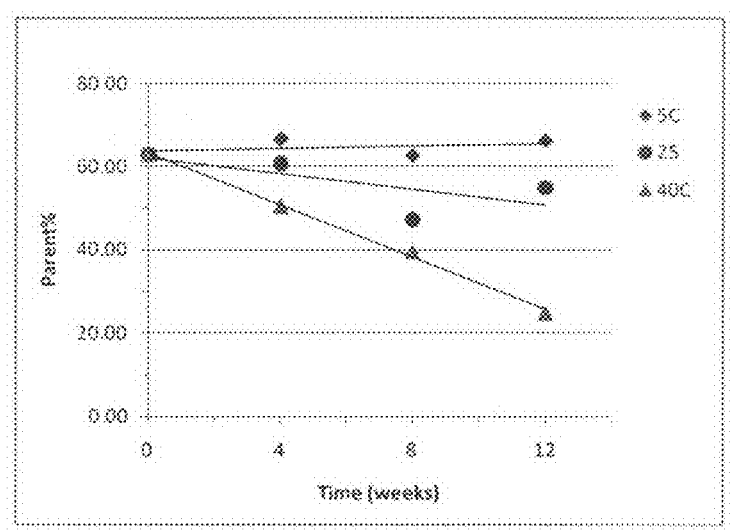
FIG. 25 is a chart showing the rate of degradation of an IFN sample as a function of time.
Figure 26:
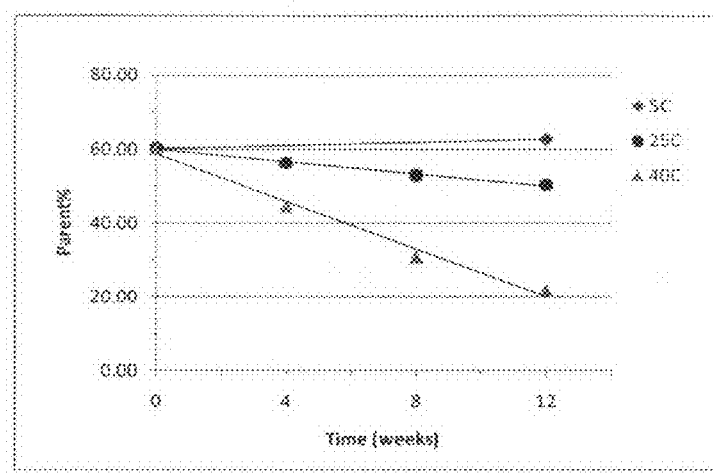
FIG. 26 is a chart showing the rate of degradation of an IFN sample as a function of time.

The data from IEX-HPLC analysis as shown in FIGS. 25 and 26 indicate that the Sample 19A material and Sample 19B material were stable at 5° C., but acidic species formed over time at 25° C. and 40° C.

Figure 27:
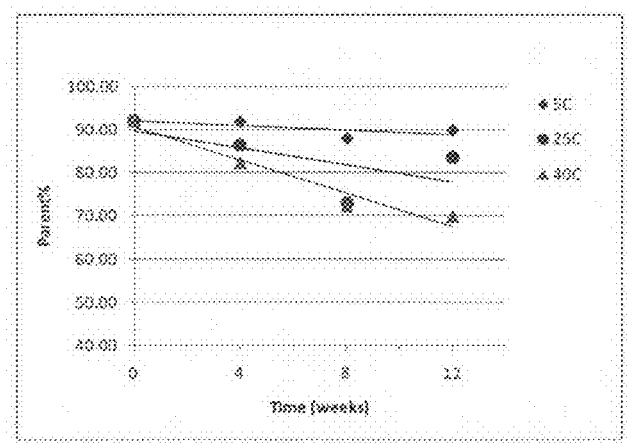
FIG. 27 is a chart showing the rate of degradation of an IFN sample as a function of time.
Figure 28:
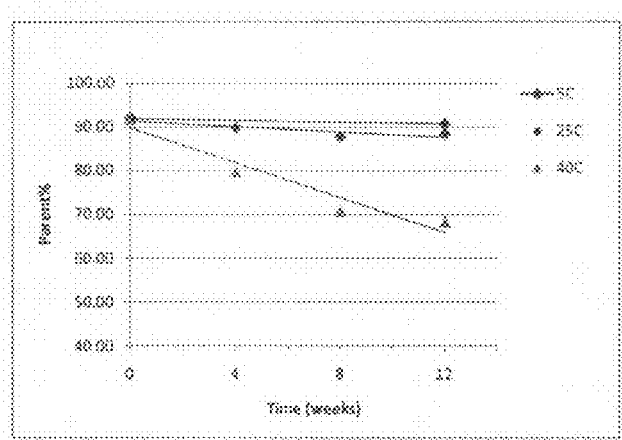
FIG. 28 is a chart showing the rate of degradation of an IFN sample as a function of time.

RP-HPLC analysis of the samples as shown in FIGS. 27 and 28 indicates that both materials were stable at 5° C.

EXAMPLE 19

The purified rhIFN beta-1b of Sample 19B with no detectable aggregates was used in this transgenic study.

Transgenic mice, immune tolerant for the human protein they express, are recognized as effective models for determining the immunogenicity of biopharmaceuticals for human use (Schellekens, H. Bioequivalence and the immunogenicity of biopharmaceuticals. *Nature Reviews Drug Discovery*, 2002 June: 1: 457-462). Mice, transgenic for human interferon beta-1a (hIFNβ), were used in order to quantify the relative differences in the ability of different formulations of hIFNβ to break immune tolerance and illicit an anti-IFNβ IgG antibody response. Different clinical formulations of recombinant human interferon beta have been tested using this model. These published experiments demonstrate a correlation between human interferon beta formulations that induce immune responses in patients and break tolerance in the transgenic mice (Hermeling, S., Jiskoot, W., Crommelin, D., Bornaes, C., Schellekens, H. Development of a transgenic mouse model immune tolerant for human interferon Beta. *Pharm Res.* 2005 June; 22(6):847-51. Epub 2005 Jun. 8.).

This mouse model, immune tolerant for the hIFNβ protein, was constructed using a DNA fragment encoding hIFNβ that was placed behind the mouse interferon beta promoter that was then microinjected into fertilized ova of C57B1/6 mice. Offspring that carried the human interferon beta gene in their chromosomal DNA, are immune tolerant for recombinant human interferon beta (rhIFNβ), and those that produce hIFNβ after induction with polyICLC were used for further breeding (Hermeling, S., Jiskoot, W., Crommelin, D., Bornaes, C., Schellekens, H. Development of a transgenic mouse model immune tolerant for human interferon Beta. *Pharm Res.* 2005 June; 22(6):847-51. Epub 2005 Jun. 8.).

The sera used to generate a positive control reference sera was derived from wild-type BALB/c mice that had been previously immunized with IFN beta. Sera samples from mice that made high, medium and low anti-IFN beta antibody responses were pooled to make a representative sera pool and this was used to quantify the responses in the transgenic mice (the standard pool was used to work up the immunoassays and prepared in advance of receiving the sera so that the assay parameters were set prior to analyzing the sera). All transgenic animal experiments were reviewed and approved by the Institutional Ethical Committee at Utrecht University, and carried out at the Transgenic Facility, Utrecht University, Utrecht, The Netherlands. The mice were at least 7 weeks of age at the beginning of the study, food and water were available ad libitum.

Three groups of five hIFNβ transgenic mice were injected intraperitoneally (i.p.) with 5 mcg of the different rhIFNβ preparations: formulated BETASERON® (IFNβ-1b, Berlex Laboratories), formulated Avonex® (IFNβ-1a, Biogen), and research grade, Sample 19B rhIFNβ-1b that contains less than or equal to 0.5% by weight protein aggregates (25 mM Sodium Acetate, pH 4.0, 9% Trehalose, 0.01% Tween20, rhIFNβ-1b 0.11 mg) on days 3-7, 10-14 and 17-21. Blood was collected from the vena saphena of these mice on days 0, 10, 20 and 26. One mouse died during the first week of dosing so the Sample 19B group only had four mice. The blood samples were incubated on ice for two hours, the sera collected, and stored at −20° C. for later analysis using an immunoassay for the determination of mouse IgG antibodies specific to human interferon β.

Human Interferon β Direct ELISA Assay:

The indirect ELISA assay followed the procedure described by Hermeling et al., with minor modifications (Hermeling, S., Jiskoot, W., Crommelin, D., Bornaes, C., Schellekens, H. Development of a transgenic mouse model immune tolerant for human interferon Beta. *Pharm Res.* 2005 June; 22(6):847-51. Epub 2005 Jun. 8; Hermeling, S., Schellekens, H., Maas C., Gebbink, M. F. B. G., Crommelin, D. J. A., Jiskoot, W. Antibody response to aggregated human interferon alpha2b in wild-type and transgenic immune tolerant mice depends on type and level of aggregation. *Journal of Pharmaceutical Sciences.* 2005 May:95(5):1084-1096.) Briefly, Microlon 96-well high-binding immunoassay plates (Greiner) were coated overnight at 4° C. with 100 μL/well (2 ug/mL) rhIFN-β-1b (BaroFold, Inc., Boulder, Colo.) in phosphate buffered saline (PBS, CellGro). The following morning the coating solution was removed and the wells washed three times with PBS containing 0.1% Tween 20 (PBS-T), 300 μL per well, per wash step. The un-adsorbed sites were then blocked for one hour at room temperature with gentle shaking with a 2% BSA (bovine serum albumin, Sigma) in PBS solution (300 μL per well). The blocking solution was then removed from all wells, the wells were washed three times in PBS-T, and excess liquid removed by gently tapping inverted assay plates on paper towels. Prior to analysis, the standard anti-sera and sera samples were diluted in assay diluent (2% BSA in PBS). The standard pooled antiserum was diluted to: 1/100, 1/200, 1/400, 1/800, 1/1,600, 1/3,200, 1/6,400, 1/12, 800, 1/25,600, 1/30,000, 1/51,200, 1/102,400, 1/204,800 and 1/500,000. Sera samples from the test mice were all diluted to 1/100. The diluted sera samples (tested in triplicate) were added to the blocked, antigen-coated assay plates (100 μL/well), the plates sealed and incubated with gentle shaking for one hour at room temperature. The liquid was removed from the wells and each well washed five times with PBS-T (300 μL/well/wash). Excess liquid was removed from the assay plates and bound mouse IgG was detected by adding 100 μL/well of goat anti-mouse IgG:peroxidase antibody (Sigma, A8924) diluted 1/5,000 in assay diluent. The assay plates were then sealed and incubated, with gentle shaking, for one hour at room temperature. The liquid was removed from the wells and each well washed five times with PBS-T (300 μL/well/wash). Excess liquid was removed from the assay plates and the color developed by adding 100 μL/well TMB (3,3', 5,5' tetramethyl benzidine) peroxidase substrate solution (KPL). After a 10 minute incubation at room temperature, the reaction was stopped by the addition of 100 μL/well of 1N HCl. Absorbances (450 nM (detection)-595 nM (background)) were recorded using a $V_{Max}$ (Molecular Devices) plate reader. Serum samples were defined positive if the absorbance of the 1/100 dilution minus the background (diluent control sample) was three times higher than the average absorbance value of the pretreatment sera minus the background. Arbitrary units of antibody binding were also calculated for individual sera samples. This determination was made by interpolating the relative binding of test sera samples from the positive standard sera curve by plotting the absorbance values of the positive control sera against the log dilution and fitting the data using a 4-parameter logistic curve-fitting program.

Figure 29:
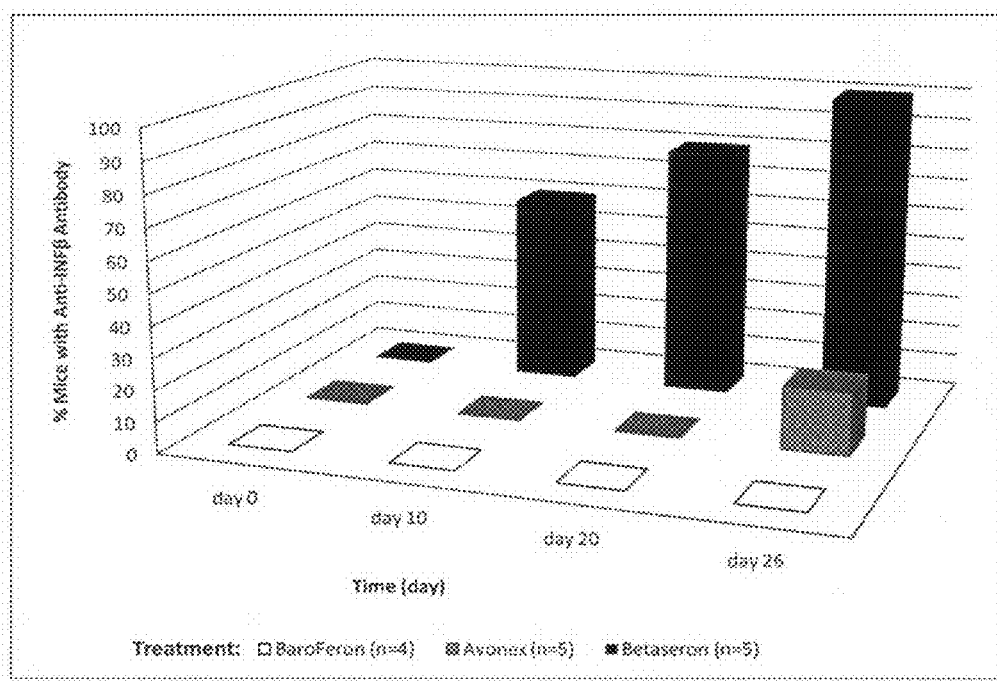
FIG. 29 is a chart showing responses in mice as a function of time.

The transgenic mice did not develop antibodies against the Sample 19B rhIFNIβ1-b preparation indicating that in this model system this hIFNβ1-b preparation was not immunogenic and did not break immune tolerance. Only a single animal treated with the Avonex®, rhIFNβ1-a preparation, broke tolerance and produced anti-hIFNβ1 IgG antibodies. However, when the data were analyzed using an ANOVA (Analysis of Variance), the response to the AVONEX® drug was not significantly different from the results seen with the Sample 19B preparation. In contrast, all five animals treated with the BETASERON rhIFNβ-b formulation had a significant immune response with the production of anti-IFNβ IgG antibodies. This result, when analyzed using ANOVA, indicates that the difference between the responses seen with the BETASERON versus the Sample 19B and AVONEX® groups is highly significant. The chart of FIG. 29 shows the IgG anti-hIFNβ responses in transgenic mice following administration of different formulations of rhIFNβ. The values represent the percent of mice in each group (n=5 mice per group for AVONEX® and BETASERON groups and n=4 for the Sample 19B (BaroFeron) group) that had sera samples that, when tested in the direct ELISA, gave an absorbance of the 1/100 dilution minus the background that was three times higher than the average absorbance value of the pretreatment sera minus the background.

Figure 30:
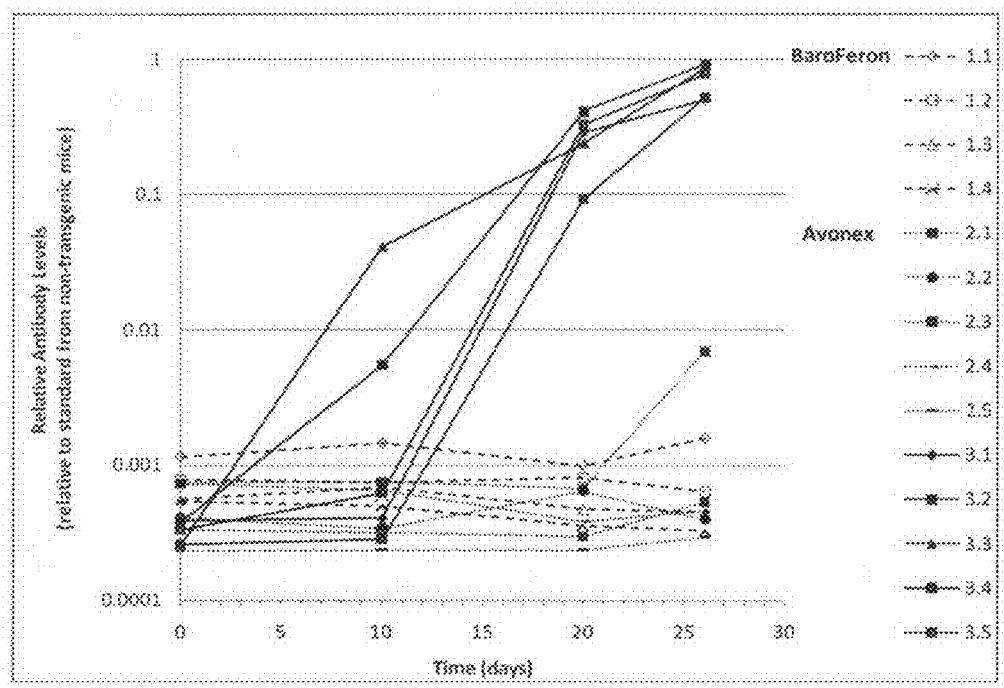
FIG. 30 is a graph showing responses in mice as a function of time.

FIG. 30 shows the IgG anti-hIFNβ responses in individual transgenic mice following administration of different preparations of rhIFNβ. A value of 1 would be equivalent to the IgG antibody levels seen in this standard sera preparation, a value between 0.0001 and of 0.001 would be equivalent to the values seen in the pre-treatment sera samples from the wild-type and transgenic mice. Again, Baroferon material in the Figure designates the Sample 19B material.

The following publications are incorporated herein by reference in their respective entireties for all purposes:

Hermeling, S., Jiskoot, W., Crommelin, D., Bornaes, C., Schellekens, H. Development of a transgenic mouse model immune tolerant for human interferon Beta. *Pharm Res.* 2005 June; 22(6):847-51. Epub 2005 Jun. 8.

Hermeling, S., Schellekens, H., Maas C., Gebbink, M. F. B. G., Crommelin, D. J. A., Jiskoot, W. Antibody response to aggregated human interferon alpha2b in wild-type and transgenic immune tolerant mice depends on type and level of aggregation. *Journal of Pharmaceutical Sciences.* 2005 May:95(5):1084-1096.

Schellekens, H. Bioequivalence and the immunogenicity of biopharmaceuticals. *Nature Reviews Drug Discovery,* 2002 June: 1: 457-462

EXAMPLE 20

The pharmacokinetics (PK) and pharmacodynamics (PD) of rhIFN beta-1b of Example 18 containing about 4 weight percent aggregates were characterized using a mechanistic PK/PD model based on receptor-mediated disposition.

The data were obtained from a good laboratory practices (GLP) study with 12 male cynomolgus monkeys to determine the exposure of interferon-β1b (IFN-β1b) and neopterin concentrations following subcutaneous injection of rhIFN-β1b or control once on days 1, 3, 5, 7, 9, 11 and 13. There were four study groups of three monkeys each. One group was a control group receiving a buffered placebo of the same volume as the highest dose. The three other study groups, each of three monkeys, received separate doses of 0.01, 0.06 or, 0.28 mg/kg of the protein, respectively. Plasma samples were collected from each animal prior to dosing, and then at 2, 4, 6, 8, 12, 24, and 48 hours after dose administration on Day 1 and Day 13.

An integrated PK/PD model including the known and suspected mechanism of action and biodistribution of rhIFN-β1b was used as previously developed and successfully tested for rhIFN-β1a in Mager, D. E., Neuteboom, B., Efthymiopoulos, C., Munafo, A., and Jusko, W. J., 2003. Receptor-mediated pharmacokinetics and pharmacodynamics of interferon-beta1a in monkeys. J Pharmacol Exp Ther 306, 262-70 (hereinafter the Mager et al article). As an overview of this model, drug from the SC (subcutaneous) site of injection ($A_{SC}$) is absorbed ($k_a$) into the plasma ($A_p$, $V_c/F$) where it binds ($k_{on}$) to the free cell-surface receptors ($R_f$) to form the drug-receptor complex (DR), which either dissociates ($k_{off}=K_D k_{on}$) or gets internalized ($k_{int}$). Distribution ($k_{pt}$, $k_{tp}$) to a non-specific tissue site ($A_T$) and drug elimination ($k_{loss}$) from the plasma are also included. The internalized activated drug-receptor (DR*) complex stimulates the zero-order production rate ($k_0$) of the precursor (P). The precursor is converted ($k_p$) into neopterin (N) which is subsequently eliminated ($k_{out}$). The model is defined by the following differential equations:

$$\frac{dA_{SC}}{dt} = -k_a A_{SC} \tag{1}$$

$$\frac{dA_P}{dt} = k_a A_{SC} + k_{tp} A_T + K_D k_{on} DR - \left(\frac{k_{on}}{V_C/F}\right) A_P \cdot R_f - (k_{pt} + k_{loss}) A_P \tag{2}$$

$$\frac{dA_T}{dt} = k_{pt} A_P - k_{tp} A_T \tag{3}$$

$$\frac{dDR}{dt} = \left(\frac{k_{on}}{V_C/F}\right) A_P \cdot R_f - (K_D k_{on} + k_{int}) DR \tag{4}$$

where $R_f$ is defined in terms of the maximum cell-surface receptor density ($R_{max}$) as:

$$R_f = R_{max} - DR \tag{5}$$

$$\frac{dDR^*}{dt} = k_{int} DR - k_r DR^* \tag{6}$$

$$\frac{dP}{dt} = k_0 \left(1 + \frac{S_{max} DR^*}{SC_{50} + DR^*}\right) - k_p P \tag{7}$$

$$\frac{dN}{dt} = k_p P - k_{out} N \tag{8}$$

The initial conditions for equations (1) and (8), were set to the dose administered and the baseline neopterin concentration ($N^0$), which was measured prior to dosing. The initial condition for equation (7) was set to the baseline concentration of the precursor ($P^0$) and was calculated using the following equation, $$P^0 = \frac{k_{out}}{k_p} N^0 \tag{9}$$

Based on the steady state conditions, the parameter $k_0$ was calculated as:

$$k_0 = k_p P^0 \tag{10}$$

The integrated PK/PD model according to the Mager et al article and involving equations 1-10 listed above was fitted simultaneously to the highest dose (0.28 mg/kg) PK data and all the PD data for three different dose levels on day 1 for single subcutaneous administration. There were no PK observations above the quantitation limit of the assay (160 pg/ml) for the lower two doses (0.01 and 0.06 mg/kg) on Day 1 in that the plasma levels for these two lower doses was too low to be detected by the PK assay. A naïve pooled approach was employed for data analysis. Only two parameters (Vc/F and $S_{max}$) were estimated while the rest were fixed to the values obtained from a previous analysis of characterizing the PK and PD data of IFN-β1b after intravenous, subcutaneous or intramuscular administration of 0.05 mg/kg of the protein. The parameter values used as fixed parameters in our current analysis are shown in the following Table 13:

TABLE 13

Fixed parameters of the integrated PK/PD model.

| Parameter (units) | Value |
|---|---|
| $k_{pt}$ (hr$^{-1}$) | 0.590 |
| $k_{tp}$ (hr$^{-1}$) | 0.0327 |
| $k_{on}$ (nM$^{-1}$hr$^{-1}$) | 0.174 |
| $k_{int}$ (hr$^{-1}$) | 0.0383 |
| $k_{loss}$ (hr$^{-1}$) | 0.629 |
| $k_a$ (hr$^{-1}$) | 0.0423 |
| $R_{max}$ (nmole/kg) | 0.305 |
| $K_D$ (nM) | 0.9 |
| $k_r$ (hr$^{-1}$) | 0.558 |
| $k_p$ (hr$^{-1}$) | 0.216 |
| $k_{out}$ (hr$^{-1}$) | 0.198 |
| $SC_{50}$ (nmole/kg) | 0.013 |

The parameters Vc/F and $S_{max}$ were estimated by the maximum likelihood method using the ADAPT 5 (beta-version) computer program (D'Argenio, D. Z., and Schumitzky, A., ADAPT II User's Guide, Biomedical Simulation Resource, Los Angeles, Calif. 1997). The variance model was specified for PK and PD outcomes using the following equation:

$$VAR_i = \sigma_1^2 Y_i^{\sigma_2} \quad (11)$$

where $VAR_i$ is the variance of the $i^{th}$ data point, $\sigma_1$ and $\sigma_2$ are the variance parameters, and $Y_i$ is the model predicted concentration or response. $\sigma_2$ was fixed to 2 for both PK and PD variance models. Separate variance parameter $\sigma_1$ was used for PK and PD measures. The estimated values are shown in the following Table 14:

TABLE 14

Estimated parameters of the integrated PK/PD model.

| Parameter (units) | Value |
|---|---|
| $V_c/F$ (L/kg) | 0.418 |
| $S_{max}$ | 8.59 |

Figure 31:
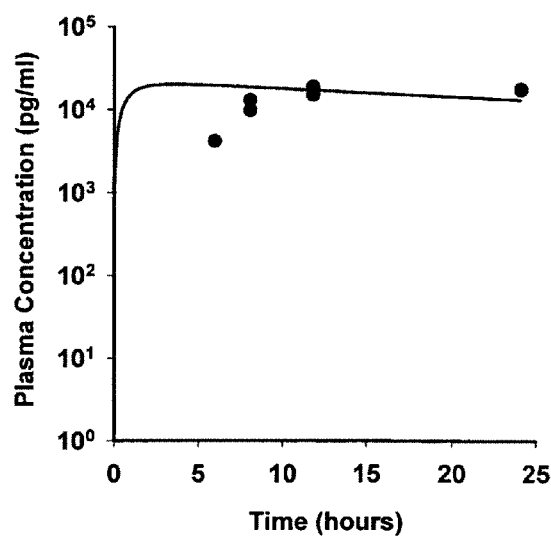
FIG. 31 is a chart showing plasma concentration as a function of time.
Figure 32:
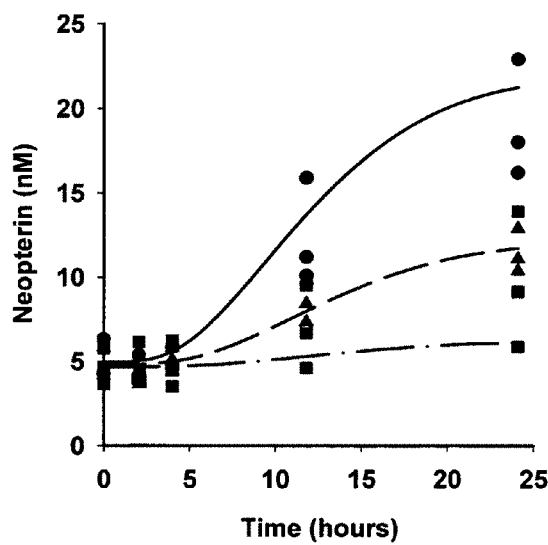
FIG. 32 is a chart showing neopterin concentration as a function of time.

Pharmacokinetics/Pharmacodynamics—Single dose. The plasma concentration-time profiles of rhIFN-β1b and the fitted curve for single subcutaneous (SC) administration of 0.28 mg/kg in monkeys after simultaneous fitting of the PK/PD data is shown in FIG. 31. The neopterin concentration-time profiles and the fitted curves for single SC administration of three dose levels (0.01, 0.06, and 0.28 mg/kg) in monkeys are shown in FIG. 32. The parameters $V_c/F$ and $S_{max}$ were estimated as 0.418 L/kg and 8.59 respectively per Table 14. Reasonable fits were obtained by co-modeling the PK and PD even in the absence of plasma concentration data for the lower two doses.

Figure 33:
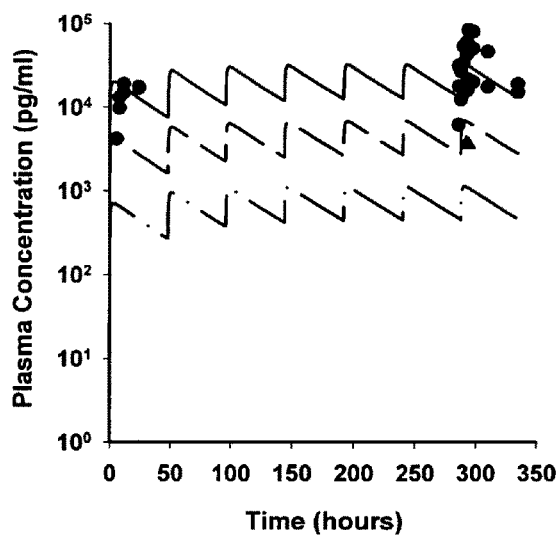
FIG. 33 is a chart showing plasma concentration as a function of time.
Figure 34:
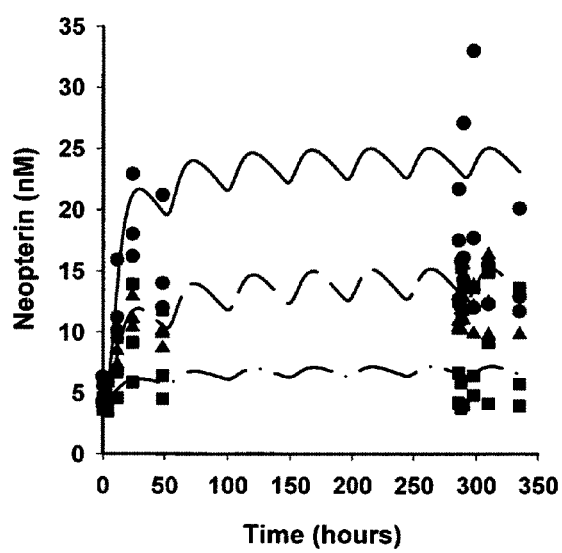
FIG. 34 is a chart showing neopterin concentration as a function of time.

Pharmacokinetics/Pharmacodynamics—Multiple dosing. The experimental PK and PD data obtained during repeated SC administration of rhIFN-β1b and multiple dosing simulation using the integrated model and the parameters specified in Tables 13 and 14 are shown in FIGS. 33 and 34 respectively. The integrated PK/PD model captured the plasma IFN-β1b concentrations for the highest dose and the neopterin concentrations for all the three doses on day 13 reasonably well. The simulated PK profile also captures the PK observation reported for the 0.06 mg/kg dose on day 13. These simulations suggest that the plasma rhIFN-β1b concentrations for 0.01 and 0.06 mg/kg might be above the quantitation limit of the assay.

References

Arakawa, T. and K. Tsumoto (2003). "The effects of arginine on refolding of aggregated proteins: not facilitate refolding, but suppress aggregation." *Biochemical and Biophysical Research Communications* 304(1): 148-152.

Lee, S. H., J. F. Carpenter, et al. (2006). "Effects of solutes on solubilization and refolding of proteins from inclusion bodies with high hydrostatic pressure." *Protein Science* 15(2): 304-313.

Randolph, T. W., J. F. Carpenter, et al. (1999). High pressure refolding of protein aggregates and inclusion bodies-U.S. Pat. Nos. 7,064,192 and 6,489,450.

Seefeldt, M. B. (2005). *High pressure refolding of protein aggregates: Efficacy and thermodynamics*. Department of Chemical and Biological Engineering. Boulder, Colo., University of Colorado—Boulder: 220.

Seefeldt, M. B., C. Crouch, et al. (2006). "Specific volume and adiabiatic compressibility measurements of native and aggregated recombinant human interleukin 1-receptor antagonist: Density differences enable pressure-modulated refolding." *Journal of Biotechnology and Bioengineering* In Press.

Seefeldt, M. B., J. Ouyang, et al. (2004). "High-pressure refolding of bikunin: Efficacy and thermodynamics." *Protein Science* 13(10): 2639-2650.

Shaked. Z., T. Stewart, et al. (1993). *Formulation Processes for Pharmaceutical Compositions of Recombinant Beta-Interferon*. U. P. Office, Schering Aktiengesellschaft.

St. John. R. J. J. F. Carpenter, et al. (2002). "High-pressure refolding of disulfide-cross-linked lysozyme aggregates: Thermodynamics and optimization." *Biotechnology Progress* 18(3): 565-571.

Tsumoto, K., M. Umetsu, et al. (2004). "Role of arginine in protein refolding, solubilization, and purification." *Biotechnology Progress* 20(5): 1301-1308.

Unless otherwise indicated, all parts and percentages are by weight and all molecular weights are weight average molecular weights. The foregoing detailed description has been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of preparing a composition comprising nonglycosylated interferon, comprising the steps of:
   a) solubilizing the aggregated interferon;
   b) precipitating the solubilized interferon;
   c) incorporating the precipitated interferon into a refolding admixture comprising 0.05 weight percent to 5.0 weight percent of a zwitterionic surfactant and having an absence of a chaotrope or denaturing surfactant; and
   d) applying greater than 3000 bars of pressure to the refolding admixture incorporating the interferon effective to refold at least a portion of the interferon to form a composition comprising nonglycosylated interferon,
   wherein the resulting composition comprises less than about 5 weight percent of protein aggregation.

2. A method of preparing a composition comprising nonglycosylated interferon, comprising the steps of:
   a) solubilizing the aggregated interferon;
   b) precipitating the solubilized interferon;
   c) incorporating the precipitated interferon into a refolding admixture comprising a zwitterionic surfactant and a disulfide shuffling reagent wherein the zwitterionic surfactant is provided in an amount between 0.05% to 5.0% of the refolding admixture and wherein the refolding admixture has an absence of a chaotrope or denaturing surfactant; and,
   d) applying greater than 3000 bars of pressure to the refolding admixture incorporating the interferon effective to refold at least a portion of the interferon;
   wherein the resulting composition comprises less than about 5 weight percent of protein aggregation.

3. A method of preparing a composition comprising nonglycosylated interferon to minimize the presence of inclusion bodies and aggregated nonglycosylated interferon, comprising the steps of:
   a) solubilizing the aggregated interferon in an aqueous medium;
   b) extracting the solubilized interferon into an organic solvent;
   c) precipitating the solubilized interferon;
   d) incorporating the precipitated interferon into a refolding admixture comprising 0.05 weight percent to 5.0 weight percent of a zwitterionic surfactant and having an absence of a chaotrope or denaturing surfactant; and,
   e) applying greater than 3000 bars of pressure to the refolding admixture incorporating the interferon effective to refold at least a portion of the interferon; wherein the resulting composition comprises less than about 5 weight percent of protein aggregation.

4. The method of claim 3, wherein the solubilized interferon is precipitated from the organic solvent by addition of a solvent selected from methanol, ethanol, isopropanol, and acetonitrile thereto.

5. The method of claim 3, wherein the refolding admixture further comprises a disulfide shuffling reagent.

6. The method of claim 3, wherein the yield of nonglycosylated interferon is at least about 30%.

7. The method of claim 3, wherein the yield of nonglycosylated interferon is at least about 40%.

* * * * *

UNITED STATES PATENT AND TRADEMARK OFFICE
CERTIFICATE OF CORRECTION

PATENT NO. : 8,273,561 B2  
APPLICATION NO. : 12/287262  
DATED : September 25, 2012  
INVENTOR(S) : Jeffrey L. Cleland et al.

Page 1 of 1

It is certified that error appears in the above-identified patent and that said Letters Patent is hereby corrected as shown below:

In the Claims

At column 77, claim 1, line 22, please delete "solubilizing the aggregated interferon" and replace it with --solubilizing aggregated interferon--.

At column 77, claim 2, line 36, please delete "solubilizing the aggregated interferon" and replace it with --solubilizing aggregated interferon--.

Signed and Sealed this
Eighth Day of July, 2014

Michelle K. Lee
*Deputy Director of the United States Patent and Trademark Office*

SEQUENCE LISTING

```
<160> NUMBER OF SEQ ID NOS: 9

<210> SEQ ID NO 1
<211> LENGTH: 166
<212> TYPE: PRT
<213> ORGANISM: Homo sapiens
```

<400> SEQUENCE: 1

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
                100                 105                 110

Arg Gly Lys Leu Met Ser Ser Leu His Leu Lys Arg Tyr Tyr Gly Arg
            115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 2
<211> LENGTH: 165
<212> TYPE: PRT
<213> ORGANISM: Artificial
<220> FEATURE:
<223> OTHER INFORMATION: Variant of SEQ ID NO.:1

<400> SEQUENCE: 2

Ser Tyr Asn Leu Leu Gly Phe Leu Gln Arg Ser Ser Asn Phe Gln Ser
1               5                   10                  15

Gln Lys Leu Leu Trp Gln Leu Asn Gly Arg Leu Glu Tyr Cys Leu Lys
                20                  25                  30

Asp Arg Met Asn Phe Asp Ile Pro Glu Glu Ile Lys Gln Leu Gln Gln
            35                  40                  45

Phe Gln Lys Glu Asp Ala Ala Leu Thr Ile Tyr Glu Met Leu Gln Asn
    50                  55                  60

Ile Phe Ala Ile Phe Arg Gln Asp Ser Ser Ser Thr Gly Trp Asn Glu
65                  70                  75                  80

Thr Ile Val Glu Asn Leu Leu Ala Asn Val Tyr His Gln Ile Asn His
                85                  90                  95

Leu Lys Thr Val Leu Glu Glu Lys Leu Glu Lys Glu Asp Phe Thr Arg
                100                 105                 110

Gly Lys Leu Met Ser Ser Leu His Leu Lys Arg Tyr Tyr Gly Arg Ile
            115                 120                 125

Leu His Tyr Leu Lys Ala Lys Glu Tyr Ser His Cys Ala Trp Thr Ile
    130                 135                 140

Val Arg Val Glu Ile Leu Arg Asn Phe Tyr Phe Ile Asn Arg Leu Thr
145                 150                 155                 160

Gly Tyr Leu Arg Asn
                165

<210> SEQ ID NO 3

```
<211> LENGTH: 510
<212> TYPE: DNA
<213> ORGANISM: Artificial
<220> FEATURE:
<223> OTHER INFORMATION: Recombinant DNA sequence coding for SEQ ID
      NO.:2

<400> SEQUENCE: 3
catatgagct acaacttgct tggattccta caaagaagca gcaatttca gtctcagaag      60 cttctgtggc aattgaatgg gaggcttgaa tactgcctca aggacaggat gaactttgac    120
atccctgagg agattaagca gctgcagcag ttccagaagg aggacgccgc attgaccatc    180
tatgagatgc tccagaacat ctttgctatt ttcagacaag attcatctag cactggctgg    240
aatgagacta ttgttgagaa cctcctggct aatgtctatc atcagataaa ccatctgaag    300
acagtcctgg aagaaaaact ggagaaagaa gatttcacca ggggaaaact catgagcagt    360
ctgcacctga aaagatatta tgggaggatt ctgcattacc tgaaggccaa ggagtacagt    420
cactgtgcct ggaccatagt cagagtggaa atcctaagga actttactt cattaacaga    480 cttacaggtt acctccgaaa ctaagaattc                                      510

<210> SEQ ID NO 4
<211> LENGTH: 33
<212> TYPE: DNA
<213> ORGANISM: Artificial
<220> FEATURE:
<223> OTHER INFORMATION: INF-beta primer oligonucleotide

<400> SEQUENCE: 4
cacgtgcata tgagctacaa cttgcttgga ttc                                  33

<210> SEQ ID NO 5
<211> LENGTH: 32
<212> TYPE: DNA
<213> ORGANISM: Artificial
<220> FEATURE:
<223> OTHER INFORMATION: INF-beta primer oligonucleotide

<400> SEQUENCE: 5
cggaattctt agtttcggag gtaacctgta ag                                   32

<210> SEQ ID NO 6
<211> LENGTH: 39
<212> TYPE: DNA
<213> ORGANISM: Artificial
<220> FEATURE:
<223> OTHER INFORMATION: INF-beta variant oligonucleotide

<400> SEQUENCE: 6
agcagcaatt ttcagtctca gaagcttctg tggcaattg                            39

<210> SEQ ID NO 7
<211> LENGTH: 39
<212> TYPE: DNA
<213> ORGANISM: Artificial
<220> FEATURE:
<223> OTHER INFORMATION: INF-beta variant oligonucleotide

<400> SEQUENCE: 7
caattgccac agaagcttct gagactgaaa attgctgct                            39

<210> SEQ ID NO 8
<211> LENGTH: 20
<212> TYPE: DNA
<213> ORGANISM: Artificial
```

-continued

```
<220> FEATURE:
<223> OTHER INFORMATION: T7 primer

<400> SEQUENCE: 8
taatacgact cactataggg                                              20

<210> SEQ ID NO 9
<211> LENGTH: 19
<212> TYPE: DNA
<213> ORGANISM: Artificial
<220> FEATURE:
<223> OTHER INFORMATION: T7 primer

<400> SEQUENCE: 9
gctagttatt gctcagcgg                                               19
```